United States Patent
Dotto et al.

(10) Patent No.: US 10,188,747 B2
(45) Date of Patent: Jan. 29, 2019

(54) METHODS AND COMPOSITIONS FOR THE TREATMENT OF CANCER

(71) Applicant: THE GENERAL HOSPITAL CORPORATION, Boston, MA (US)

(72) Inventors: Gian Paolo Dotto, Boston, MA (US); Yang Sui Brooks, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 2 days.

(21) Appl. No.: 15/114,462

(22) PCT Filed: Feb. 12, 2015

(86) PCT No.: PCT/US2015/015638
§ 371 (c)(1),
(2) Date: Jul. 27, 2016

(87) PCT Pub. No.: WO2015/130477
PCT Pub. Date: Sep. 3, 2015

(65) Prior Publication Data
US 2016/0339119 A1 Nov. 24, 2016

Related U.S. Application Data

(60) Provisional application No. 61/939,918, filed on Feb. 14, 2014.

(51) Int. Cl.
| | | |
|---|---|---|
| *A61K 48/00* | (2006.01) | |
| *A61K 31/277* | (2006.01) | |
| *A61K 31/565* | (2006.01) | |
| *A61K 31/275* | (2006.01) | |
| *A61K 31/15* | (2006.01) | |
| *A61K 31/353* | (2006.01) | |
| *A61K 31/357* | (2006.01) | |
| *A61K 31/423* | (2006.01) | |
| *A61K 9/00* | (2006.01) | |

(52) U.S. Cl.
CPC .......... *A61K 48/00* (2013.01); *A61K 9/0014* (2013.01); *A61K 9/0053* (2013.01); *A61K 31/15* (2013.01); *A61K 31/275* (2013.01); *A61K 31/277* (2013.01); *A61K 31/353* (2013.01); *A61K 31/357* (2013.01); *A61K 31/423* (2013.01); *A61K 31/565* (2013.01)

(58) Field of Classification Search
None
See application file for complete search history.

(56) References Cited

U.S. PATENT DOCUMENTS

| | | |
|---|---|---|
| 2007/0292405 A1 | 12/2007 | Seckl et al. |
| 2009/0036415 A1 | 2/2009 | Rubin et al. |
| 2013/0281525 A1* | 10/2013 | Sherr .................... A61K 31/35 514/456 |

OTHER PUBLICATIONS

Estrogen receptor beta in breast cancer, by Haldosen et al. ("Haldosen") (Molecular and Cellular Endocrinology vol. 382, Issue 1, Jan. 25, 2014, pp. 665-672).*
"Estrogen receptor-beta agonist diarylpropionitrile counteracts the estrogenic activity of estrogen receptor-alpha agonist propylpyrazole-triol in the mammary gland of ovariectomized Sprague Dawley rats," to Song et al. ("Song") (The Journal of Steroid Biochemistry and Molecular Biology vol. 130, Issues 1-2, May 2012).*
"Regulation of submaxillary gland androgen-regulated protein 3A via estrogen receptor 2 in radioresistant head and neck squamous cell carcinoma cells," by Grunow et al. ("Grunow") (J. Exp. Clin. Cancer Res. Feb. 6, 2017;36(1):25).*
"Roles of NOTCH1 as a Therapeutic Target and a Biomarker for Lung Cancer: Controversies and Perspectives," by Guo et al. ("Guo") (vol. 2015 (2015), Article ID 520590, 8 pages).*
"Squamous Cell Carcinoma of the Lung: Molecular Subtypes and Therapeutic Opportunities," by Moreno et al. ("Moreno") Clin Cancer Res; 18(9); 2443-51.*
Bender et al., "Roles of 17β-Estradiol Involve Regulation of Reelin Expression and Synaptogenesis in the Dentate Gyrus", Cerebral Cortex 20(12):2985-2995 (2010).
Brooks et al., "Multifactorial ERβ and NOTCH1 control of squamous differentiation and cancer", J. Clin. Invest. 124 (5):2260-2276 (2014).
Chae et al., "Genetic Polymorphisms of Estrogen Receptors α and β and the Risk of Developing Prostate Cancer", PLoS One 4(8):e6523 (2009).
Hao et al., "Notch-1 activates estrogen receptor-α-dependent transcription via IKKα in breast cancer cells", Oncogene 29(2):201-213 (2010).

* cited by examiner

*Primary Examiner* — Nancy J Leith
(74) *Attorney, Agent, or Firm* — Nixon Peabody LLP

(57) ABSTRACT

The technology described herein is directed to agonists of, e.g. Esr2, Dlx5, and/or Egr3, for the inhibition of cancer cells (e.g. squamous carcinoma cancer cells) and the treatment of cancer.

2 Claims, 36 Drawing Sheets
Specification includes a Sequence Listing.

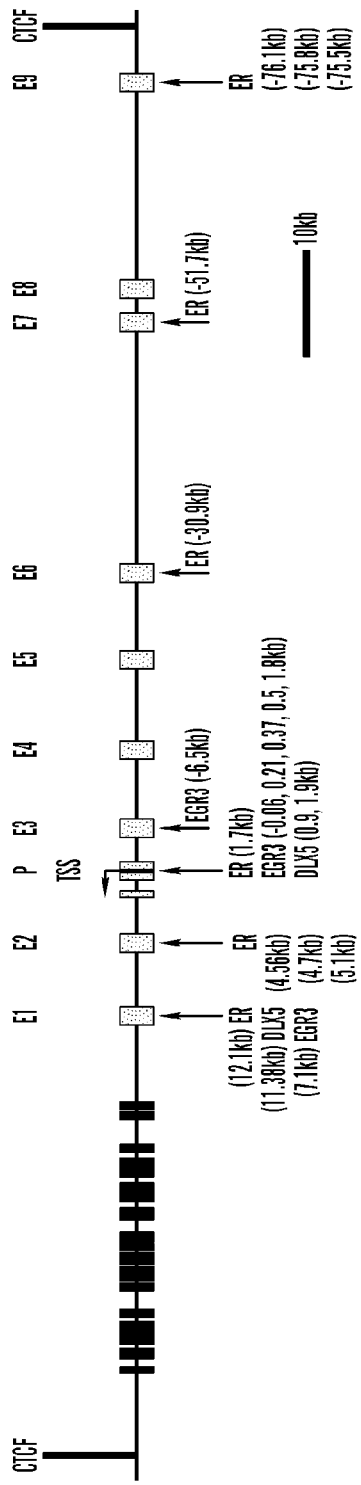
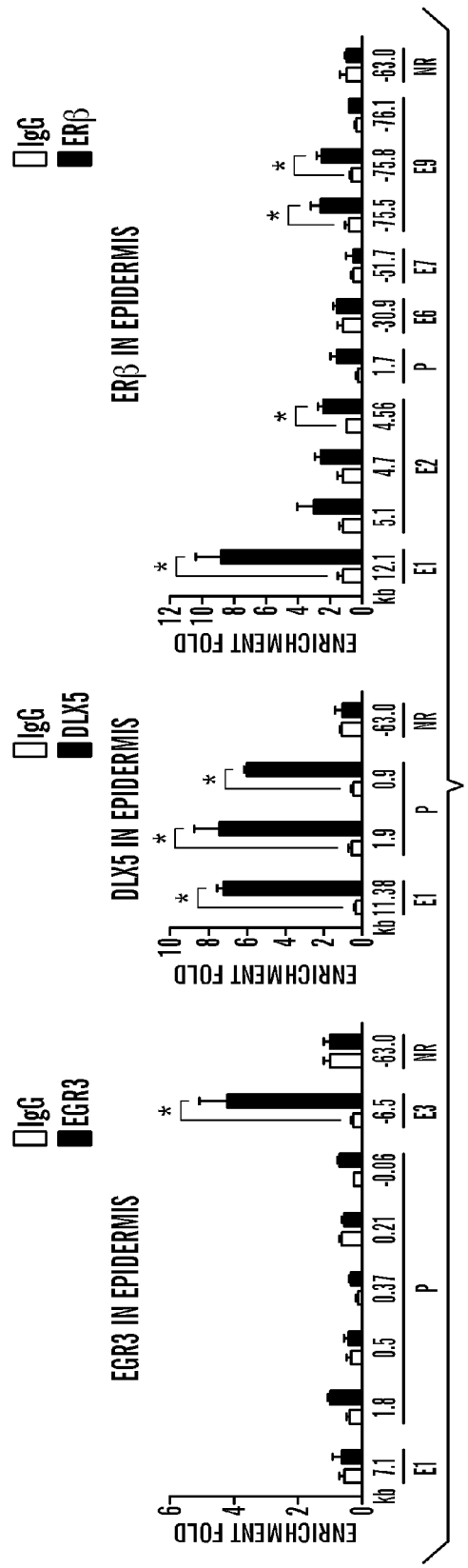
FIG. 2A
FIG. 2B

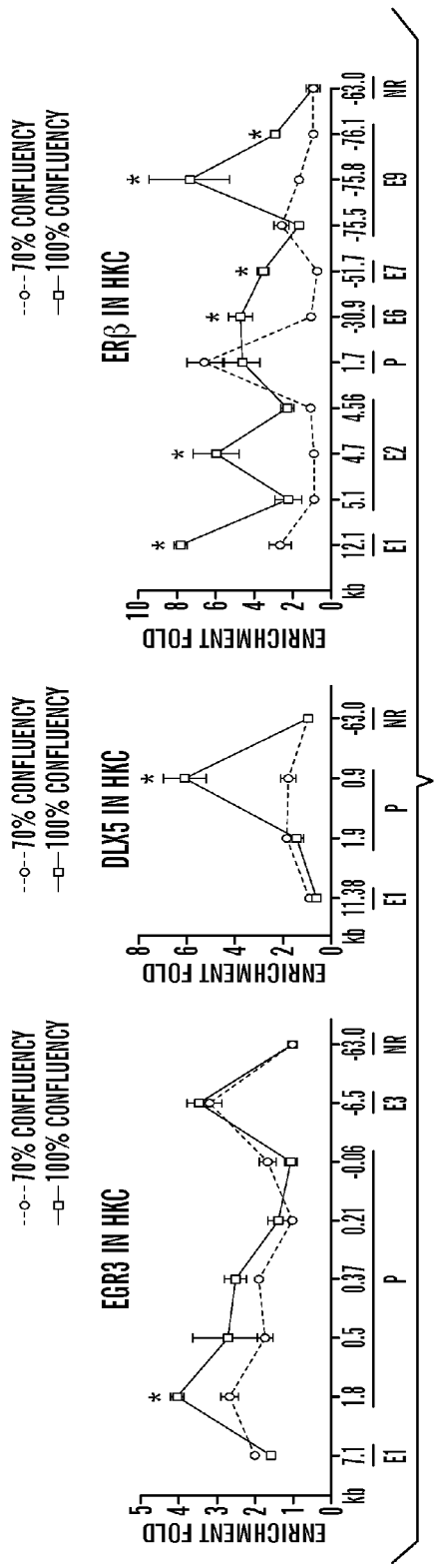
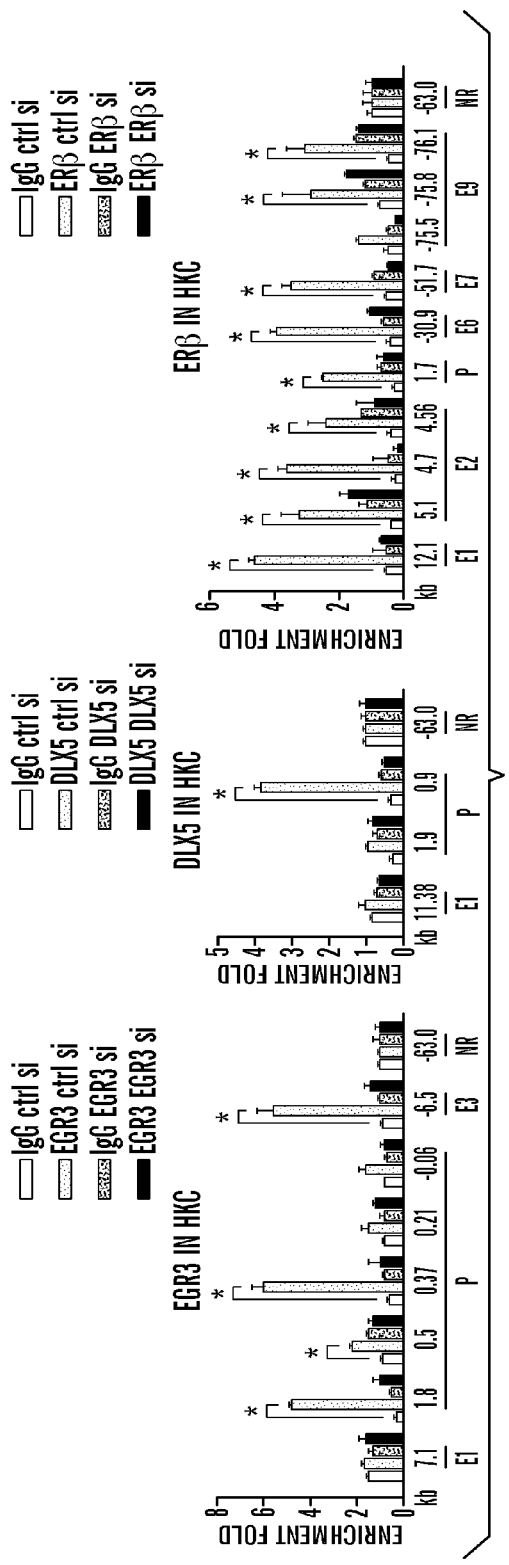
FIG. 2C
FIG. 2D

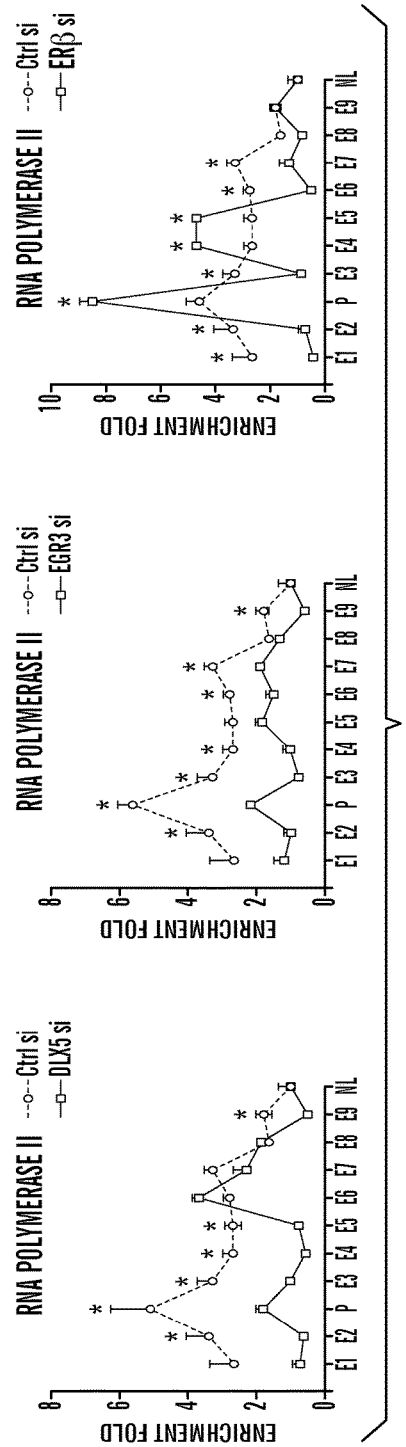
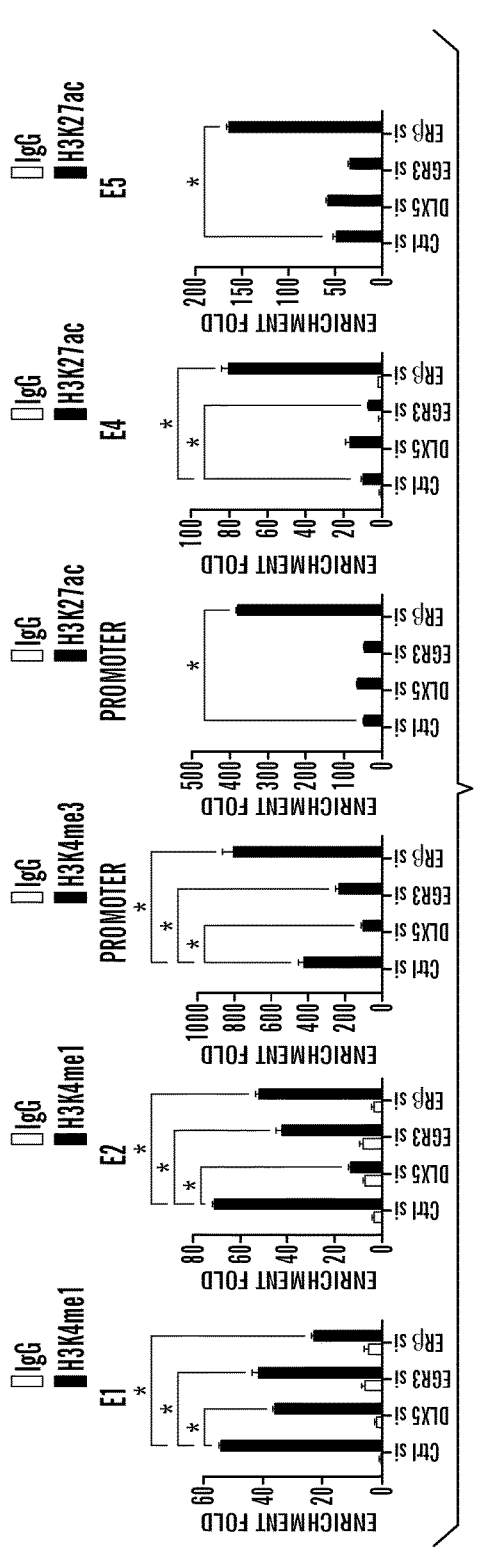
FIG. 3B
FIG. 3C

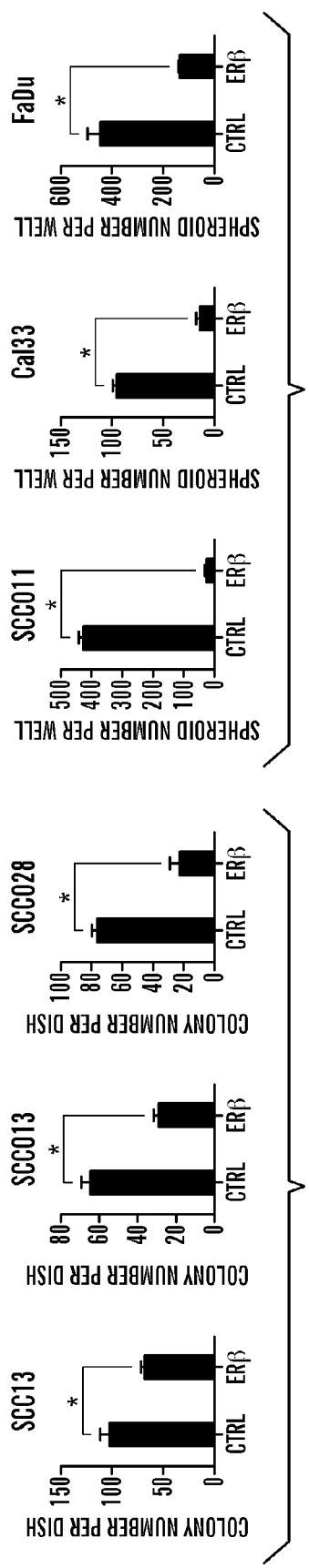
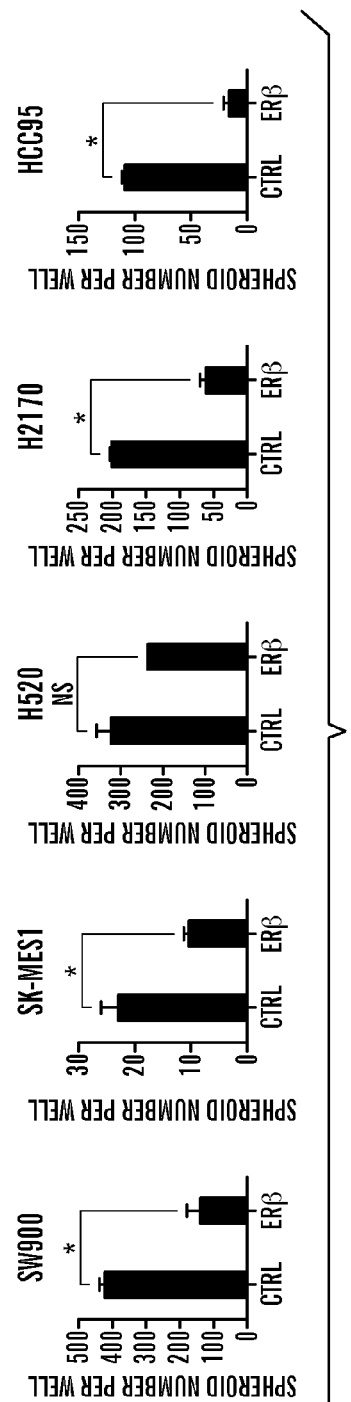
FIG. 8B
FIG. 8C
FIG. 8D

SEQUENCE LISTING

<160> NUMBER OF SEQ ID NOS: 133

<210> SEQ ID NO 1
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gattccggat ccgccaccat ggactacaag gacgacgatg acaaggatat aaaaaactca    60
cca                                                                 63

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctgctgcgg ccgcctactg agactgtggg ttctg                            35

<210> SEQ ID NO 3
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caccatggac tacaaggacg acgatgacaa gacaggagtg tttgacaga              49

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctaatagagt gtcccggagg c                                            21

<210> SEQ ID NO 5
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caccatggac tacaaggacg acgatgacaa gaccggcaaa ctcgccgag              49

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgaggcgcag gtggtgacca c                                            21

<210> SEQ ID NO 7
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caccaccatg gactacaagg acgacgatga caaggatata aaaaactcac ca          52

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctactgagac tgtgggttct g                                            21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
agauccaccu caagcaaaat t                                            21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
cagagaaggu uucagaagat t                                            21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
ccuuaccugu aaacagagat t                                            21

<210> SEQ ID NO 12
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gattccggat ccgccaccat ggactacaag gacgacgatg acaaggat               48

<210> SEQ ID NO 13
<211> LENGTH: 49
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 13
caccatggac tacaaggacg acgatgacaa gacaggagtg tttgacaga                    49

<210> SEQ ID NO 14
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caccaccatg gactacaagg acgacgatga caaggatata aaaaactcac ca                52

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttgggaggag cagatttttg                                                    20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttgtctccag ggaaatcgtg                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tcatttggag tgttggtgga                                                    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtttccagtg cctgtgtcct                                                    20

<210> SEQ ID NO 19
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 19
ggaggttctg cgatgagtgt                                                   20

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
caaaagttgc acagaagtca ta                                                22

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agtttctggc cccttgga                                                     18

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agaaccgcag gatgaaaatg                                                   20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gaagcaggac attggagaca                                                   20

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gaagaaggag gtgcccaag                                                    19

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
gatggctaca gagaatgtaa tgga                                        24

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcaacagaaa gtcgtcaaca ag                                          22

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
catccctctc accacctttc                                             20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgccctcaga aatcaacaga                                             20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
accagcctct gtgtttgtcc                                             20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgagcgatga caggagtgtt                                             20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cctatcgcaa ctccatcacc                                         20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtgtaagccc tcacctccac                                         20

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcaagaactc tccaacatcc t                                       21

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tgcacaagaa gagccacaag                                         20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cagctagtgc tcaccctcct                                         20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aaggaacgga tatggtttca                                         20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 37
ggccctcaga tcgtctcata                                               20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gttccagcgt gaggtttgtt                                               20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gaaaagcatg ggcaactcac a                                             21

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gcaatgttgc cagtgtctgt                                               20

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ggggcattta cccagcttt                                                19

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gccgacaccc aatacctg                                                 18

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
```

```
agctccacac gcagcataa                                              19

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gctgctggta tttcctcctc                                             20

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ctgccctcgc aaagcaac                                               18

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccgcagagcc cacactcc                                               18

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
agataaatgg cccggagaag                                             20

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cacaccggcc tcctaactc                                              19

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
```
cgccaaagtt tccaaagg                                                      18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agaggcgctg ctgagtgt                                                      18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gtcgagggca ggacactt                                                      18

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cctcacacac caccaagaga                                                    20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gccctcttca gtaccccttg                                                    20

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cccagagacc aaccatcct                                                     19

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tcacacttcc cgccattc                                                      18

```
<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tgaggtgagg gcaggagtag                                                    20

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cactaggagc agggcgagt                                                     19

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
accccgtgga gacctgct                                                      18

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gctgtgaaca accacgtctc                                                    20

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gcagcagatg gtgaaggag                                                     19

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tcctgactgg gtctctctcc                                                    20
```

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
gcctcctgtg ctacctgtg                                              19

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
tgaaaactgc actggcacac                                             20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
atcttaccgg ggctgagaaa                                             20

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
gctgcactct ctcttccctt t                                           21

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
actttcccct tcgctgtctc                                             20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
gcgcctcagt cttctctcct                                             20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
agggcaggag tagcgagaag    20

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
caggggatgt cggtgtgt    18

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
ttgacagcat cttggcatc    19

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
gctgtgaaca accacgtctc    20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
tcccaccagc gtacactaaa    20

<210> SEQ ID NO 73
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
ataaaaaact caccagctgc tgcggccgcc tactgagact gtgggttctg    50

<210> SEQ ID NO 74

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ctaatagagt gtcccggagg c                                                  21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ctactgagac tgtgggttct g                                                  21

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cactggcatg acacacaaca                                                    20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ggcagtggca gatgtaggag                                                    20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ctcgcacacc atgatcactt                                                    20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cgatacactt tgccccattc                                                    20

<210> SEQ ID NO 80
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gctgccacag tagttcaggt                                               20

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tgctgcattt cttggtcac                                                19

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cttcgtagat tgtgctgata gaga                                          24

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gggtgagaga agggagaagg                                               20

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ggctcctcgg atactcaaaa c                                             21

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tctgagctgt tgttcgtagt gt                                            22

<210> SEQ ID NO 86
<211> LENGTH: 20
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 86
agttggaagg ggagtcgaag                                        20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
ggctatactt gggcatggaa                                        20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
cgccaccttg taactccatc                                        20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
tgaaaccatc caccaacaca                                        20

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
tgacgtttcc tctgcacttc t                                      21

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 91
ctgagacgga tggtgcatag                                        20

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
cctctgcttc tcttgaatct tctt                                           24

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
tggggtcctg ttcactcct                                                 19

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gcgtcacacc attgctattc                                                20

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
gcgcaagaca agttcaagg                                                 19

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
acacctccat ccaacagctc                                                20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ccacagtctc tccatctcct                                                20

<210> SEQ ID NO 98
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 98
caccctcacc ccattaaaga                                                 20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
taaggctggg acaaatcgac                                                 20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
tgtcgatctg aagcaggatg                                                 20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gccttgacct tttcagcaag                                                 20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
tcgtgttgtt ccttctgctc                                                 20

<210> SEQ ID NO 103
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
tctcagcccc ggtaagatg                                                  19

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 104
cgcaggggac agaacact                                                18

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gtgccagtgc agttttcatc                                              20

<210> SEQ ID NO 106
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cggtgagacc tgcctgaa                                                18

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
tttggtttcc tgttgcttct c                                            21

<210> SEQ ID NO 108
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gagttaggag gccggtgtg                                               19

<210> SEQ ID NO 109
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ccagcatgga gagggaaaa                                               19

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 110
ccagccgggg aagagagg                                                 18

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
aggccaagag aaaaggcaag                                               20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gtaggaggct ggagcttttg                                               20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
cgctttagct ttggacaacc                                               20

<210> SEQ ID NO 114
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
cggaggatgg ttggtctct                                                19

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
tggtgcaaaa tgccttcc                                                 18

<210> SEQ ID NO 116
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 116
ccccagcaac ccatgatac                                                  19

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
tgaggagtgg atgagggtgt                                                 20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
agatgcagat ggcctcagtt                                                 20

<210> SEQ ID NO 119
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
ctgttcagag gcgggaaa                                                   18

<210> SEQ ID NO 120
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
tgagggcaag actccacac                                                  19

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
tcctggggta gagaggaggt                                                 20

<210> SEQ ID NO 122
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122

-continued ttggcatttg tccctcaac                                          19

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
ctctgaaggg cttgaattgg                                         20

<210> SEQ ID NO 124
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
gcgtctagct tgccttcct                                          19

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gtctctgggg aatcgagtga                                         20

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
aacgctcaga cttttcttgc t                                       21

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
aatcagctca cagtcccaca                                         20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128

```
<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
gaggagtgga tgagggtgtg                                                   20

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
acagtgaaga ctgaaaccag gag                                               23

<210> SEQ ID NO 131
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
tccagacatg acctgcatc                                                    19

<210> SEQ ID NO 132
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
gagggcaaga ctccacacc                                                    19

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
tccctggtgt ctgagtgtga                                                   20
```

METHODS AND COMPOSITIONS FOR THE TREATMENT OF CANCER

CROSS-REFERENCE TO RELATED APPLICATIONS

This application is a 35 U.S.C. § 371 National Phase Entry Application of International Application No. PCT/US2015/015638 filed Feb. 12, 2015, which designates the U.S. and claims benefit under 35 U.S.C. § 119(e) of U.S. Provisional Application No. 61/939,918 filed Feb. 14, 2014, the contents of which are incorporated herein by reference in their entirety.

GOVERNMENT SUPPORT

This invention was made with federal funding under Grant Nos. F32 AR059471 and AR39190 awarded by the National Institutes of Health. The U.S. government has certain rights in the invention.

SEQUENCE LISTING

The instant application contains a Sequence Listing which has been submitted electronically in ASCII format and is hereby incorporated by reference in its entirety. Said ASCII copy, created on Feb. 6, 2015, is named 030258-080831-PCT_SL.txt and is 30,769 bytes in size

TECHNICAL FIELD

The technology described herein relates to regulation of Notch1 activity and/or levels, e.g. to inhibit cancer cell proliferation or for the treatment of cancer.

BACKGROUND

Squamous cell carcinomas (SCCs) are the most common form of human solid tumors and major cause of cancer lethality. Squamous cell carcinomas are notoriously resistant to conventional and targeted drug treatments.

Notch signaling plays a pivotal role in diverse developmental, physiological and pathological processes. Among the four known Notch receptors, Notch1 plays the most significant role in squamous cell differentiation. Recent whole genome sequencing studies identified recurrent loss-of-function mutations of the Notch1 gene in head and neck, cutaneous and lung SCCs, consistent with the tumor suppressing function that Notch1 activation can play in this tumor type. Control of Notch1 activity has been highly studied at the level of receptor processing and activation, while surprisingly little is known on direct transcription control of the Notch1 gene.

SUMMARY

As described herein, the inventors have discovered that NOTCH1 is positively regulated by a number of genes provided in Table 1, e.g. Esr2, Dlx5, and Egr3. Agonists of these genes are demonstrated herein to increase the level and/or activity of NOTCH1, thereby inhibiting cell growth and survival in squamous cell carcinomas.

In one aspect, described herein is a method of inhibiting the growth and/or proliferation of a cancer cell, the method comprising contacting the cell with an agonist of a gene selected from Table 1. In some embodiments, the level and/or activity of NOTCH1 is increased.

In one aspect, described herein is a method comprising administering an agonist of a gene selected from Table 1. In some embodiments, the agonist is a nucleic acid encoding the gene. In some embodiments, the gene is selected from the group consisting of: Esr2; Dlx5; and Egr3. In some embodiments, the agonist of Esr2 is selected from the group consisting of: 17β-estradiol (E2); 2,3-bis(4-Hydroxyphenyl)-propionitrile (DPN); LY50037; liquiritigenin; MF101 (MENERBA); WAY20070; YA-202196; WAY-214156; ERB041; FERb033; (S)-Equol; diarylpropionitrile; AC74131; silybinin; genistein; AC-186; KB9520; ERB-79; GTx-822; silymarin; EVIENDEP™; and epigallocatechin gallate (EGCG). In some embodiments, the cancer is a carcinoma. In some embodiments, the cancer is squamous cell carcinoma. In some embodiments, the squamous cell carcinoma is located in the skin, head, neck, or lung. In some embodiments, the agonist is administered topically. In some embodiments, the agonist is administered orally.

BRIEF DESCRIPTION OF THE DRAWINGS

FIGS. 1A-1B depict heat maps in which two different HKC strains were reverse transfected with siRNAs against the indicated set of transcription factor genes, with siRNAs against NOTCH1 and p53 (top 2 lines) as control for effectiveness of the assay. Three different siRNAs per gene were tested (si1-si3), each in triplicate wells. One week after transfection, HKCs were analyzed by RT-qPCR for levels of NOTCH1 and HEY1 expression, with 36134 for normalization. Results are expressed as heat map of $\log_2$ ratios relative to cells transfected with scrambled siRNA control. Arrows indicate genes selected for further validation. FIG. 1C depicts the validation of the above results for the indicated set of genes by reverse transfection of a third independent strain of HKCs, utilizing the same conditions as before. RT-qPCR analysis was used to assess siRNA KD efficiency of each gene and impact on levels of NOTCH1 primary and mature transcripts and other NOTCH pathway components. FIGS. 1D and 1E depct RT-qPCR (FIG. 1D) and immunoblot analysis (FIG. 1E) of expression of the indicated genes in HKCs under proliferative conditions (70% confluence [cf]) and at various time (days [D]) of differentiation induced by high cell density. FL, full length; NEXT, NOTCH extracellular truncation, ICD, intracellular domain. mRNA levels were normalized for 36β4 and presented as fold-changes relative to cells under proliferative conditions. P<0.007; *P<0.001. Similar results were obtained with analysis of an independent strain of HKCs (data not shown).

FIGS. 2A-2D demonstrate binding of endogenous EGR3, DLX5, and ERβ to NOTCH1 gene locus in human epidermis and HKCs. FIG. 2A depicts a schematic representation of NOTCH1 gene locus. CTCF: insulator elements. Black bars, exons; gray boxes, predicted enhancer (E1-E9) and promoter (p) regions; black arrows, predicted binding regions of DLX5, EGR3, and/or ERα/β (nucleotide locations in brackets). FIG. 2B depicts graphs of ChIP assays of EGR3, DLX5, and ERβ binding to the corresponding predicted sites of the NOTCH1 locus in intact human epidermis. All ChIP samples were examined in parallel by PCR amplification of a negative control region (NR) located between enhancers 8 and 9 of the NOTCH1 locus and devoid of predicted EGR3-, DLX5-, and ERβ-binding sites. Results are expressed as fold of enrichment for each indicated binding site relative to the negative control region.

Statistical significance was determined by unpaired Student's t test (*P<0.05). FIG. 2C depicts graphs of ChIP assays of EGR3, DLX5, and ERβ binding to the NOTCH1 locus in HKCs under growing (70% confluence) versus differentiating (100% confluence) conditions. ChIP assays were performed and data analyzed as in B (*P<0.05). Enrichment folds in the immunoprecipitates with nonimmune IgGs were in all cases less than 1. FIG. 2D depicts ChIP assays of endogenous EGR3, DLX5, and ERβ binding to the NOTCH1 locus in differentiating HKCs (100% confluence) with or without individual KD of the 3 genes. Results were analyzed as in B (*P<0.05). Results similar to those in FIGS. 2B-2D were obtained with HKCs of independent origin; see also FIGS. 12A-12C.

FIGS. 3A-3C demonstrate the essential role of EGR3, DLX5, and ERβ in RNA PolII recruitment to the NOTCH1 locus and/or pause release. FIG. 3A depicts graphs of ChIP analysis of HKCs under growing versus differentiating conditions for levels of PolII occupancy of the NOTCH1 locus and associated levels of active histone marks of active promoter (H3K4me3, H3K27ac) and/or enhancer (H3K4me1, H3K27ac) regions. All ChIP samples were examined in parallel by PCR amplification of a negative control locus (NL) in chromosome 4, devoid of active chromatin marks and utilized for similar normalization purposes in previous studies with a number of cell types. Enrichment folds were calculated and plotted as in FIGS. 2B-2D (*P<0.05). Enrichment folds in the immunoprecipitates with nonimmune IgG were in all cases less than 1. Similar patterns of PolII binding were obtained with HKCs of independent origin; see also FIG. 13B. FIG. 3B depicts graphs of HKCs transfected with siRNA against EGR3, DLX5, or ERβ versus siRNA controls were processed 96 hours later (at 100% confluency) for ChIP assays of levels of PolII occupancy of the NOTCH1 locus. For ease of representation, levels of PolII binding in cells with KD of the individual genes are separately shown, utilizing PolII levels in control cells as the same point of reference (*P<0.05). FIG. 3C depicts graphs of HKC samples utilized in FIG. 3B were analyzed in parallel by ChIP assays for levels of active histone marks at the NOTCH1 promoter and enhancer 1, 2, 4, and 5 regions (*P<0.05). Results similar to those in FIG. 3A-3C were obtained with HKCs of independent origin; see also FIG. 13D.

FIG. 4A depicts results of HKCs infected with shRNAs silencing lentiviruses versus control were analyzed 96 hours later by immunoblotting. Gene KD efficiency was assessed by parallel blots of those for NOTCH1 and Keratin 1 expression. Similar results were observed at the NOTCH1 mRNA level and in another experiment with HKCs of independent origin (FIGS. 14A-14C). FIG. 4B depicts graphs of HKCs infected with lentiviruses as in FIG. 4A superinfected with retrovirus expressing NOTCH1 intracellular domain fused to the human estrogen receptor (rNert), or vector control (Neo). 24 hours later, cultures were treated with OH-tamoxifen (OH-TAM) for 48 hours for nuclear NOTCH1 intracellular domain translocation. Expression of Keratin genes was determined by RT-qPCR (*P<0.02). Results similar to those were obtained with a second HKC (FIG. 14C). FIG. 4C depicts results of HKCs infected with lentiviruses as in FIG. 4A grown in duplicate dermal equivalent gels at air-liquid interface for 12 days. The experiment was performed twice. Immunoblot analysis of full-length NOTCH1 expression in reconstituted epidermis with signal quantification (numbers) by densitometric scanning and γ-tubulin normalization.

FIG. 5A demonstrates that HKCs under sparse conditions were infected with retroviruses expressing EGR3, DLX5, or ERβ versus empty vector controls as indicated, followed 72 hours later (at approximately 80% confluence) by immunoblot analysis for levels of these proteins as well as the full-length NOTCH1 protein (NOTCH1 FL) and the intracellular activated form (NOTCH1 ICD). HKCs under differentiating conditions (100% confluence for 3 days: 100% cf+3D) were analyzed in parallel as point of reference. Similar results were observed at the RNA level and in other experiments with HKCs of independent origin (FIGS. 15A-15B). FIG. 5B depicts graphs of HKCs with or without infection with EGR3-, DLX5-, and ERβ-expressing retroviruses as in the previous panel were treated with DAPT (10 μM) or DMSO control at 24 hours after infection followed, 48 hours later, by RT-qPCR analysis of involucrin gene expression, with 36β4 for normalization. As an alternative, HKCs stably infected with a shRNA lentivirus against NOTCH1 or empty vector control were superinfected with the EGR3, DLX5, and ERβ expressing retroviruses, followed 72 hours later by RT-qPCR analysis of the same genes. FIG. 5C depicts graphs of HKCs with or without infection with EGR3-, DLX5-, and ERβ-expressing retroviruses as in FIG. 5A were analyzed, 72 hours after infection, by RT-qPCR of the indicated genes. *P<0.001.

FIG. 6A depicts quantitation of immunohistochemical analysis of EGR3, DLX5, and ERβ expression in tissue arrays of in situ and invasive skin SCCs versus normal skin (n=31, 226, 10, respectively). Quantification of percentage of positive nuclei (DLX5) or immunoreactivity (EGR3 and ERβ) as indicated. Error bars represent mean±SEM. Statistical analysis was performed using 1-way ANOVA. *P<0.05; P<0.01; *P<0.001; ****P<0.0001. Original magnification, ×14.4. FIG. 6B depicts the results of Skin (SCC12 and SCC13) and H/N SCC cell lines (Cal27, Cal33, FaDu, SCCO11, SCCO13, SCCO22, and SCCO28) were analyzed with HKCs under growing conditions by immunoblotting. FIG. 6C depicts results of indicated lung SCC cell lines analyzed in parallel with HBECs for NOTCH1, EGR3, DLX5, and ERβ expression by immunoblotting.

FIG. 7A depicts expression profiles of ERβ-controlled genes in clinically occurring SCCs versus normal tissues. Microarray analysis of gene expression in HKCs plus/minus ERβ-KD identified genes under ERβ control (>1.5-fold change). Expression profiles of these genes were examined in clinically occurring SCCs, utilizing our own and published data sets. Dark/light columns on the right refer to the set of down- and upmodulated genes in HKCs with ERβ silencing that were found to be concordantly (dark colors) versus discordantly (light colors) regulated in clinically occurring SCCs in parallel with a differential gene family distribution. FIG. 7B depicts a graph of numbers of genes with mutations frequencies of 10% or more in lung and H/N SCCs from patients of one or both sexes (Fisher's exact test <0.05). Overlapping circles show numbers of genes with similar mutation frequency distribution in lung and H/N SCCs. FIG.

7C depicts expression profiles of genes differentially expressed in female versus male H/N patients. Gene families with statistically significant enrichment are indicated on the left. Genes with a role in squamous differentiation are zoomed in. Log 2 expression values, median centered and divided by SD, are represented.

Figure 8A:
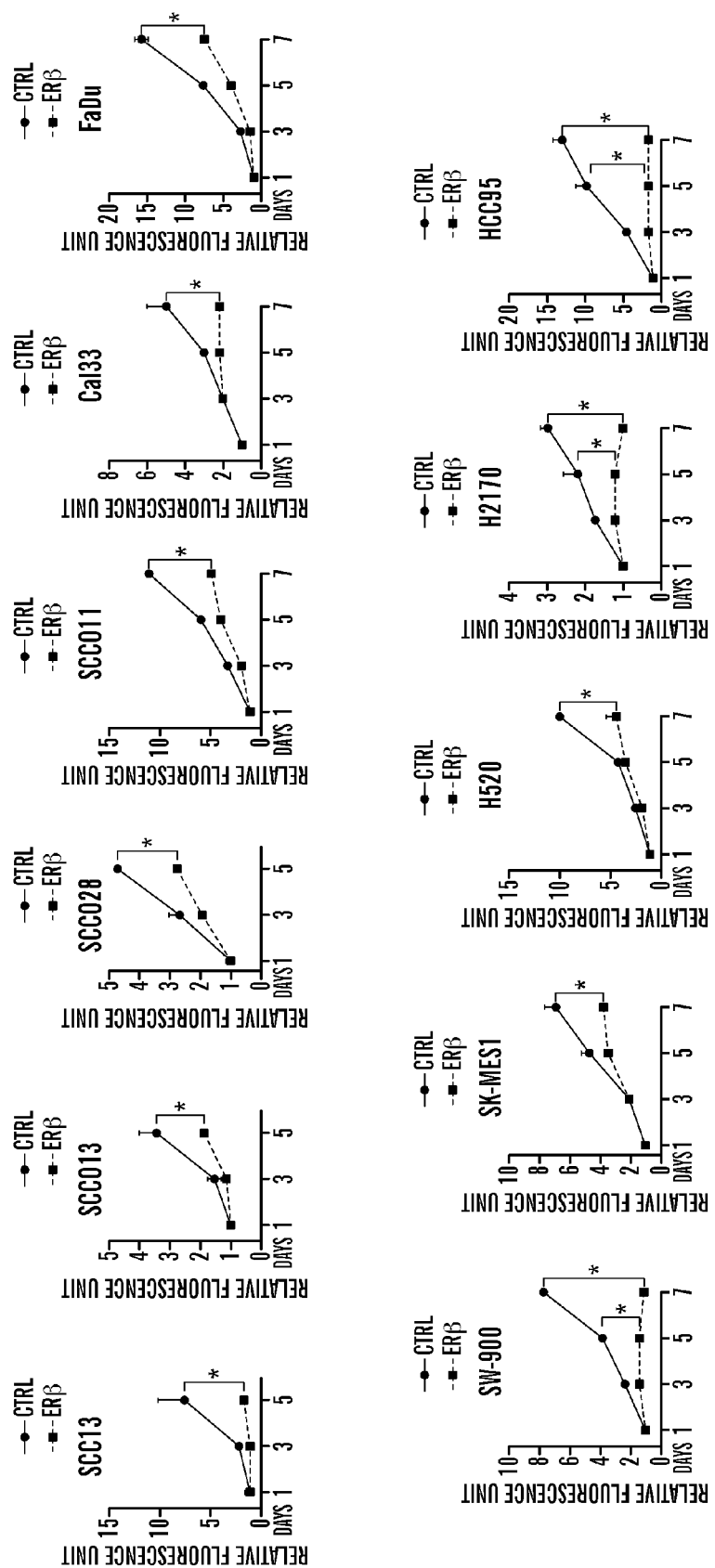
Figure 8E:
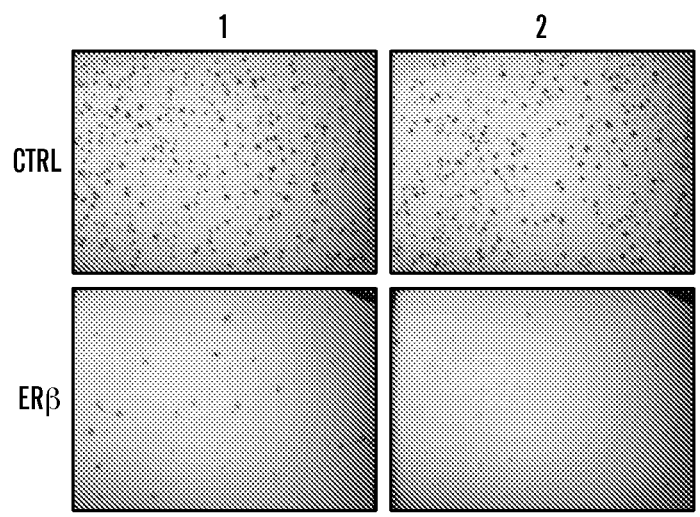

FIGS. 8A-8E demonstrate that elevated ERβ expression suppresses proliferation of skin, lung, and oral SCC cells. FIG. 8A depicts the results of Alamar blue cell density assays. Cell lines derived from skin (SCC13), H/N (Cal33, FaDu, SCCO11, SCCO13, SCCO28), and lung (H520, H2170, HCC95, SK-MES1, SW900) SCCs were infected with either an ERβ-expressing lentivirus (SCC13, SCCO13, and SCCO28) or retrovirus (all other cell lines) versus corresponding empty vector controls, followed, 48 hours later, by G418 selection. Stably infected cells were plated in 96-well plates (2000 cells/well). Alamar blue fluorescence intensity assays were performed in triplicate every 2 days as indicated. Data are presented as mean fold change of fluorescence intensity±SD over day 1. *P<0.05. FIG. 8B depicts the results of clonogenicity assays. Skin (SCC13) and H/N (SCCO13 and SCCO28) SCC cells infected with an ERβ-expressing lentivirus versus empty vector were plated at limited density on triplicate dishes (103 cells/60 mm dish), and colony formation was measured by crystal violet staining 10 days later. *P<0.05. FIGS. 8C-8D depict spheroid assays. Skin and H/N (FIG. 8C) and lung (FIG. 8D) SCC cells were infected with an ERβ-expressing retrovirus or lentivirus versus empty vector as in FIG. 8A. Stably infected cells were plated in duplicate in Matrigel suspension in 8-well chambers (2000 cells/well). Spheroid numbers were quantified 10 days later by digital acquisition of the whole well images and ImageJ™ software analysis. *P<0.05. FIG. 8E depicts representative images of spheroids formed by SCC011 cells infected with control versus ERβ-expressing retroviruses. Original magnification, ×2.5. Photographs of spheroids formed by other SCC cells are shown in FIG. 16B.

Figure 9A:
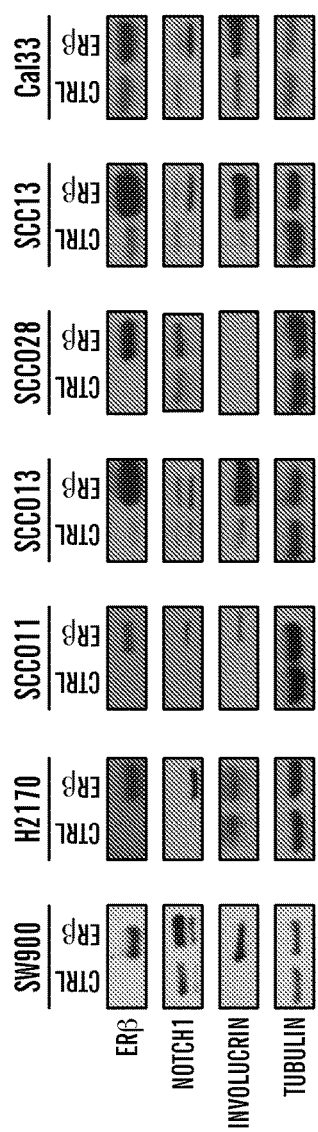
Figure 9B:
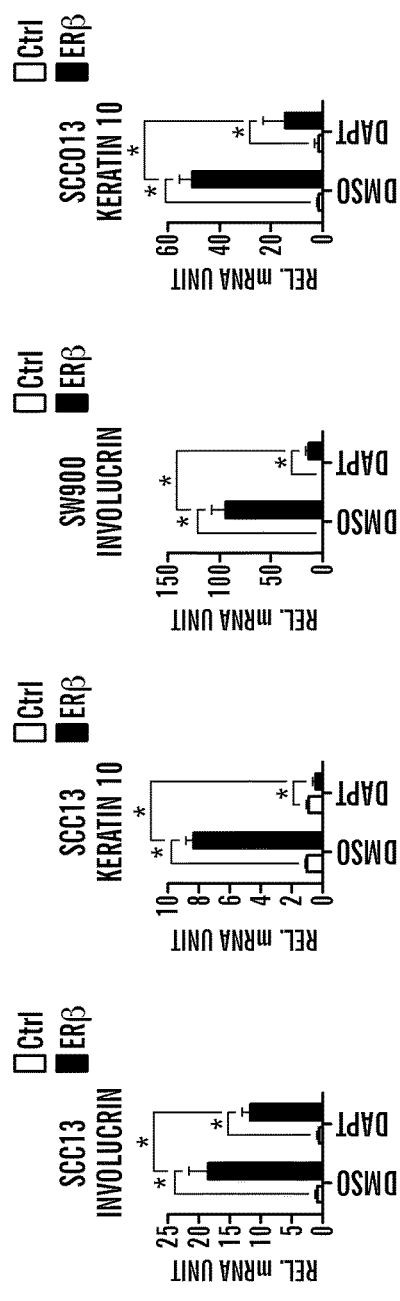

FIGS. 9A-9B demonstrate that elevated ERβ expression induces NOTCH1 expression and differentiation. FIG. 9A depicts results of SCC cell lines infected with ERβ-expressing viral vectors versus controls as in FIGS. 8A-8E were analyzed for expression of the indicated proteins by immunoblotting. FIG. 9B depicts graphs of SCC13 (skin), SW900 (lung), and SCCO13 (oral) SCC cells infected with ERβ-expressing and control viral vectors were treated 24 hours after infection with DAPT (10 μM) or DMSO control followed, 72 hours later, by RT-qPCR analysis of involucrin and keratin 10 differentiation marker expression. *P<0.05.

Figure 10A:
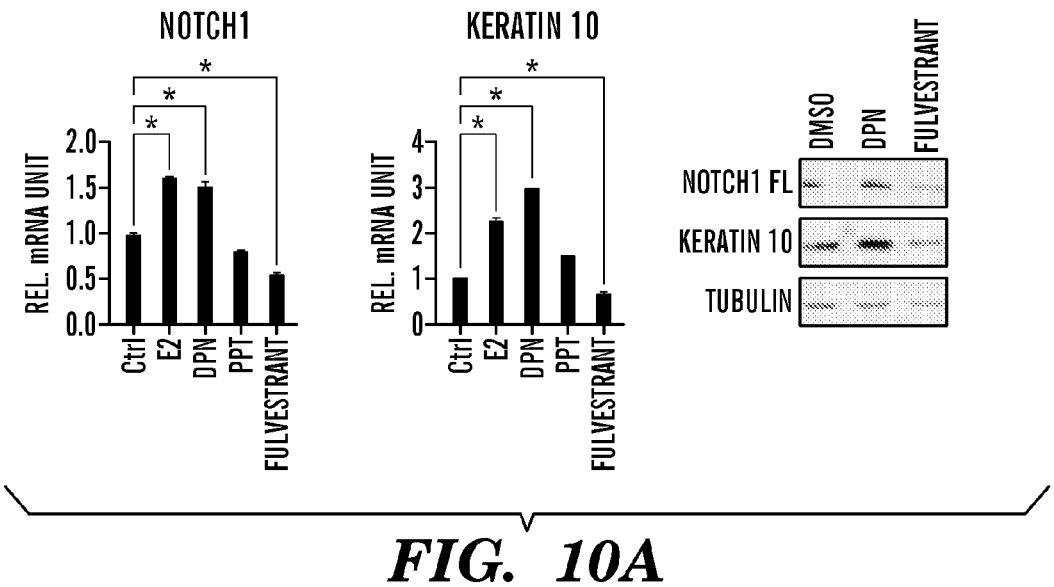
Figure 10B:
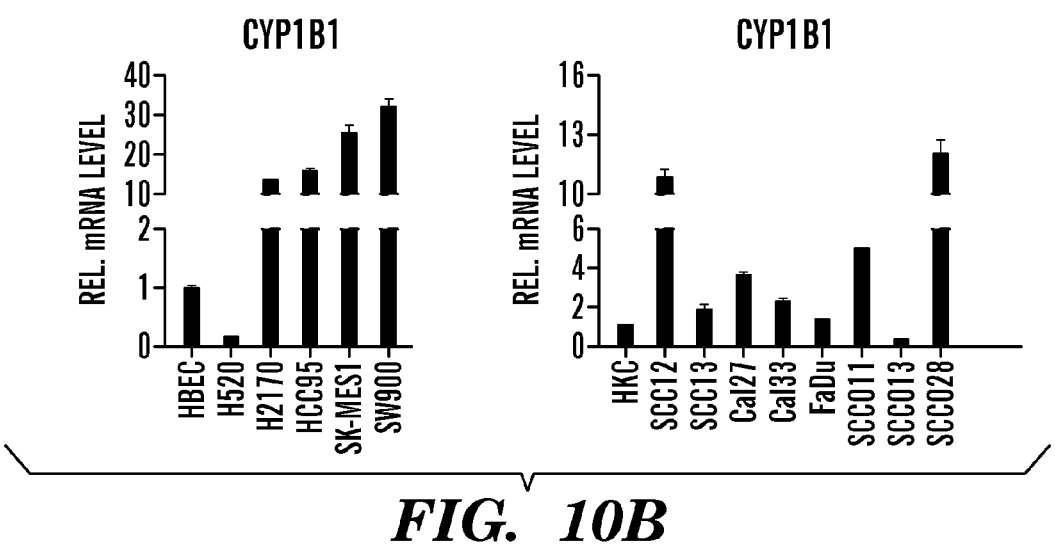
Figure 10C:
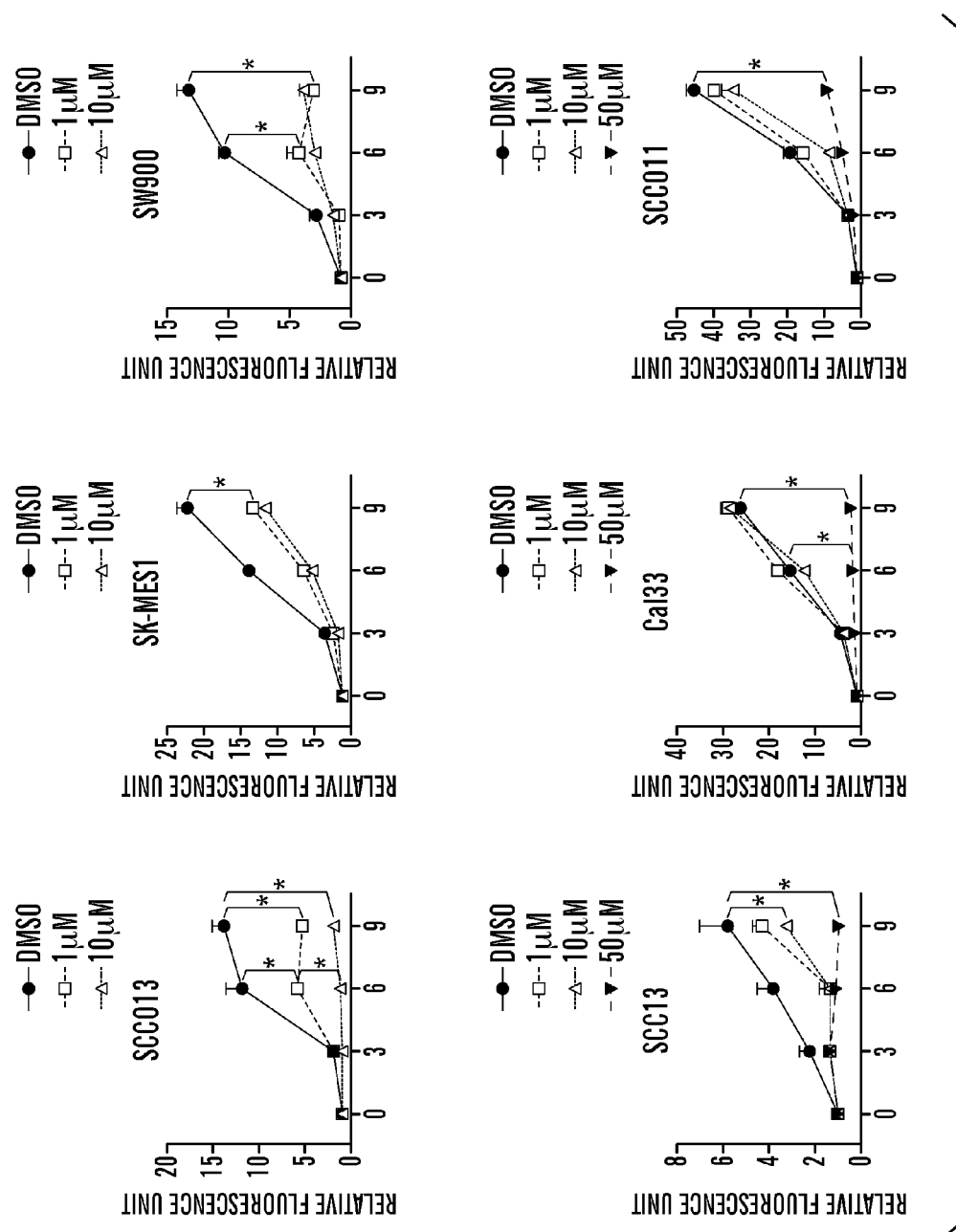
Figure 10D:
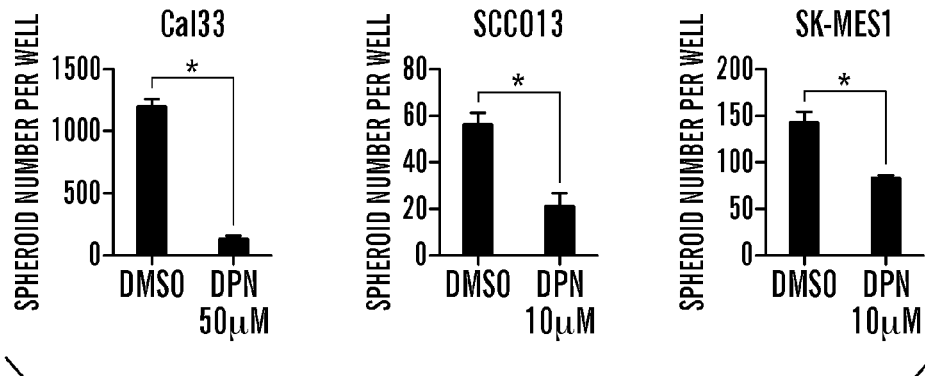
Figure 10E:
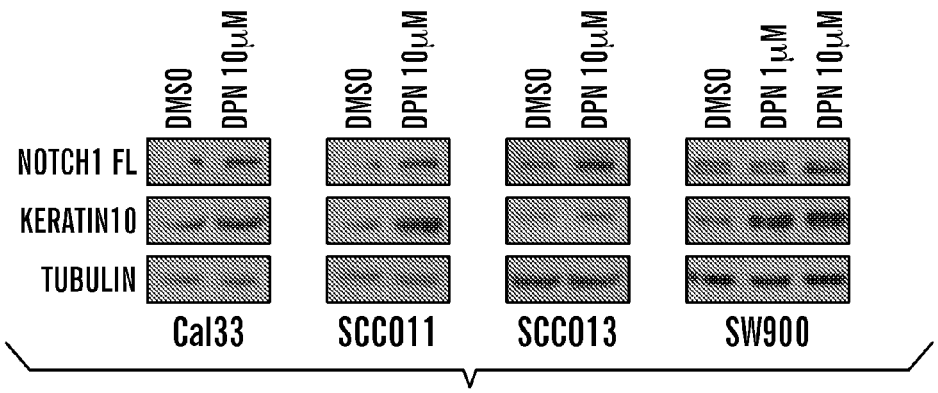
Figure 17A:
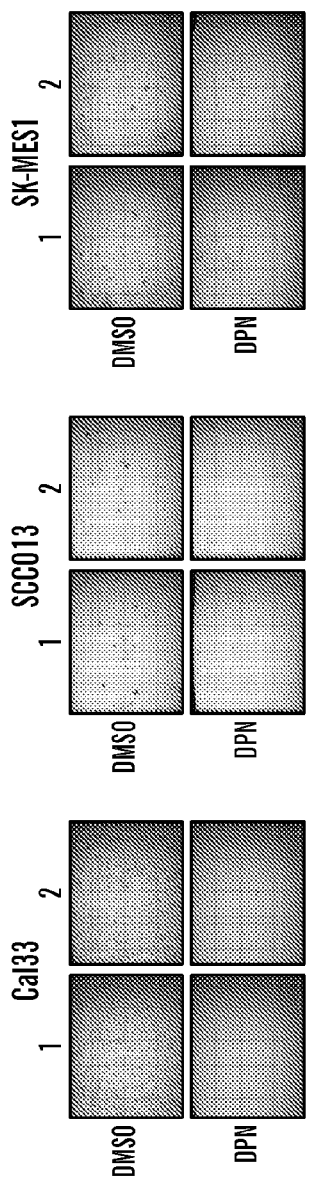
Figure 17B:
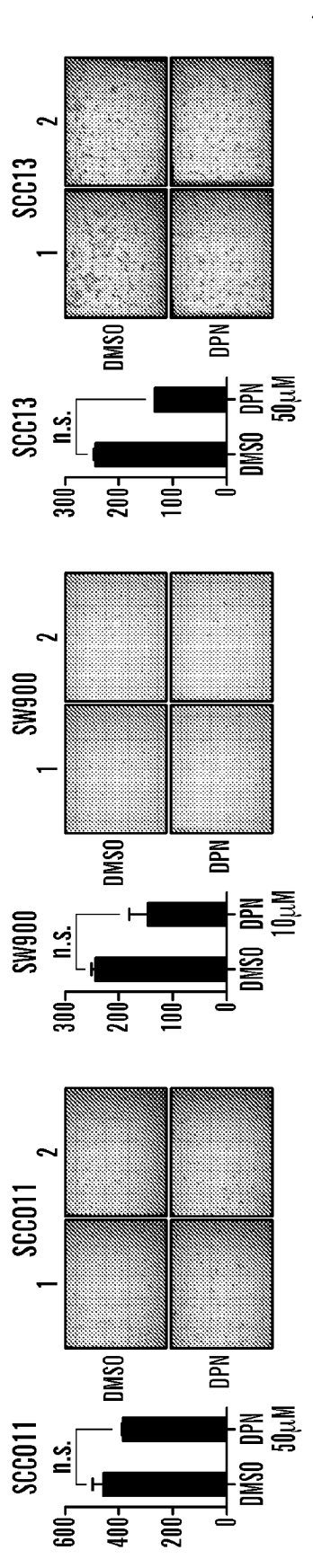

FIGS. 10A-10E demonstrate that ERβ agonists induce NOTCH1 and differentiation marker expression in HKCs and SCC cells with concomitantly attenuated proliferation. FIG. 10A depicts graphs of differentiating HKCs (100% confluence) treated with 10 nM estradiol (E2), 100 nM ERβ-specific agonist (DPN), 100 nM ERα-specific agonist (PPT), 10 nM estrogen receptor panantagonist (fulvestrant) or DMSO control followed, 72 hours later, by RT-qPCR (*P<0.05) and immunoblot analysis of the indicated genes/ proteins. FIG. 10B depicts graphs of expression of CYP1B1 determined by RT-qPCR in lung and keratinocyte-derived SCC cell lines in parallel with HBECs and HKCs, respectively. FIG. 10C depicts graphs of Alamar blue density assays of SCC cells performed in triplicate wells and treated with DPN or DMSO (refreshed every other day). Data are presented as mean fold change of fluorescence intensity±SD (*P<0.05). FIG. 10D depicts graphs of indicated SCC cells plated in duplicate on Matrigel precoated chambers with spheroid number quantification 10 days later by ImageJ™ analysis of whole-cell images. Data are duplicates±SD (*P<0.05). Photographs and spheroid quantification of other SCC cells are shown in FIGS. 17A-17B. FIG. 10E depicts graphs of indicated SCC cells treated with the ERβ-specific agonist DPN at the indicated doses for 10 days.

Figure 11:
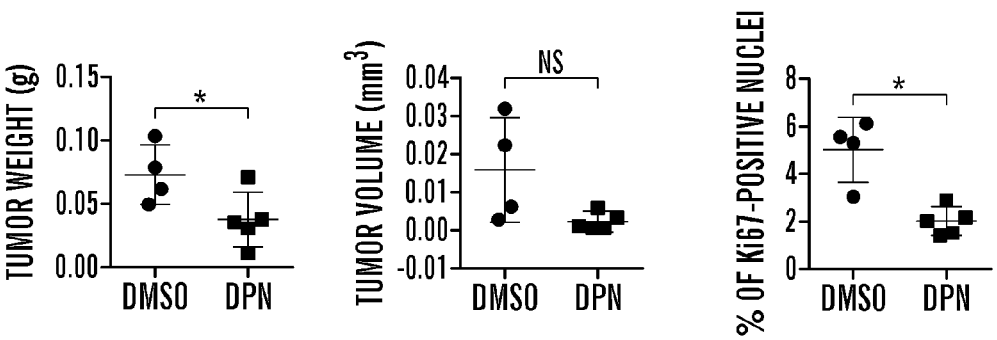

FIG. 11 demonstrates that ERβ agonist treatment delays SCC tumor growth and promotes differentiation. SCC013 cells were injected intradermally in the left supra-scapular region of NOD/SCID mice (1×106 cells per injection). Forty-eight hours after injection, DPN was injected intraperitoneally into a cohort of mice (n=5) at a dose of 20 mg/kg every day in parallel with another cohort of mice (n=4) injected with DMSO vehicle alone. Animals were sacrificed 10 days later. Tumor weight and volume were measured, followed by determination of Ki67-labeling index by immunofluorescence analysis of histological section. *P<0.05.

Figure 12A:
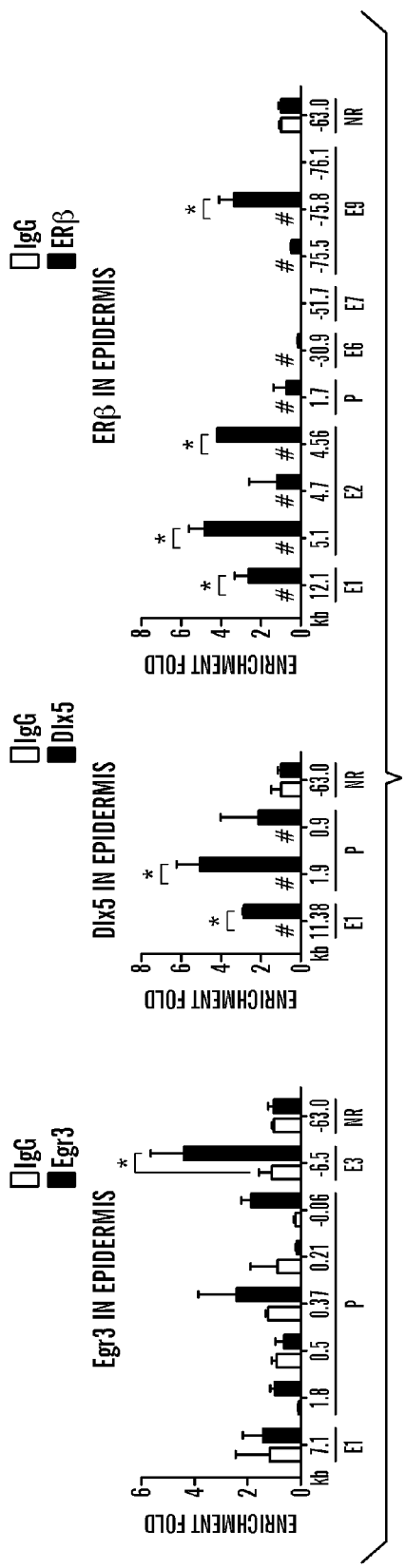
Figure 12B:
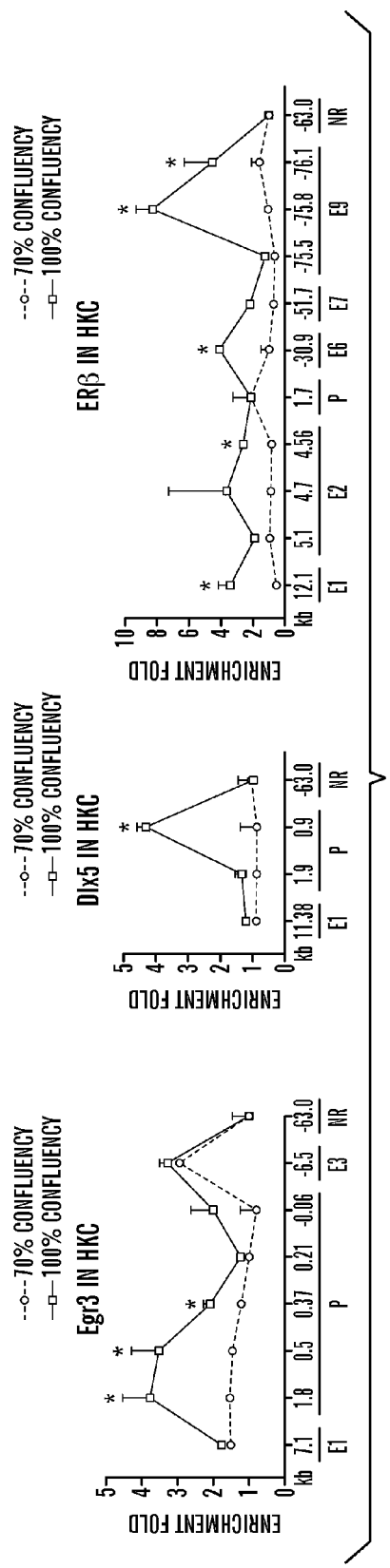
Figure 12C:
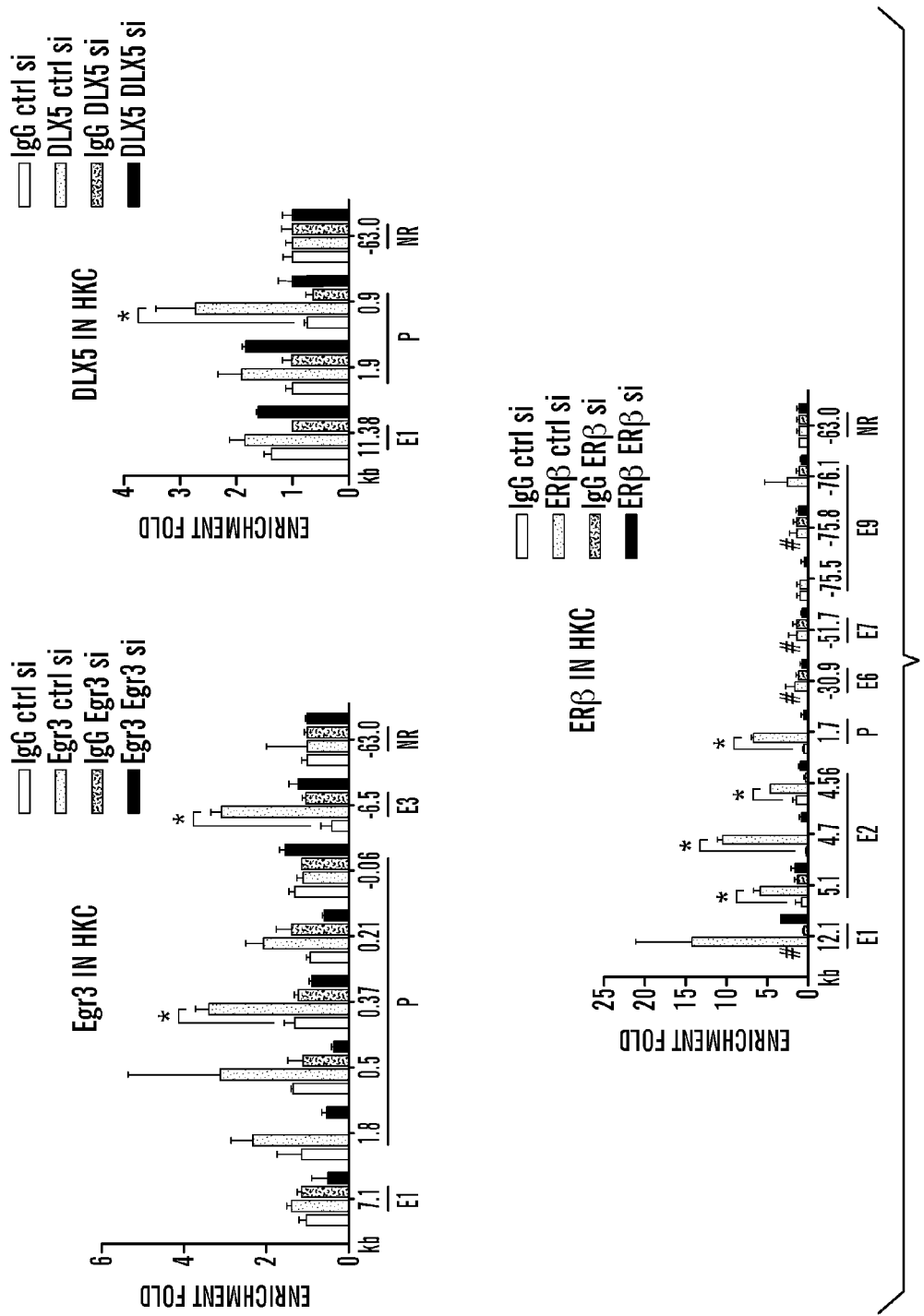

FIGS. 12A-12C demonstrate binding of endogenous Egr3, Dlx5 and ERß to the Notch1 gene locus in human epidermis and HKCs. FIG. 12A depicts graphs of similar ChIP assays as those described for FIG. 2B undertaken utilizing an epidermal sample of different origin. # refers to undetectable signal in some ChIP assays with non immune IgG (*p<0.05). FIGS. 12B and 12C depicts graphs of similar ChIP assays as those described for FIGS. 2C and 2D utilizing HKCs of a different origin under growing versus differentiating conditions (FIG. 12B) or plus/minus knockdown of the Egr3, Dlx5 and ERß genes (FIG. 12C). Data were similarly analyzed and plotted (*p<0.05).

Figure 13A:
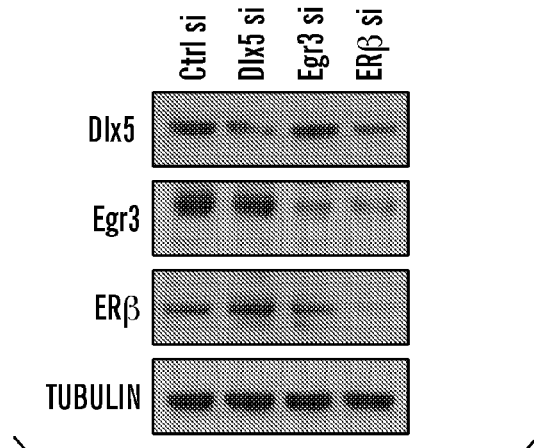
Figure 13B:
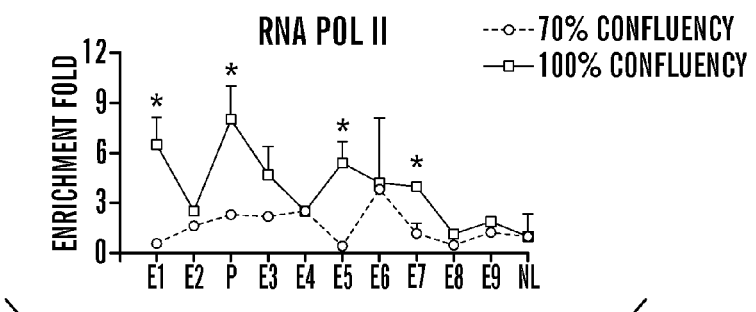
Figure 13C:
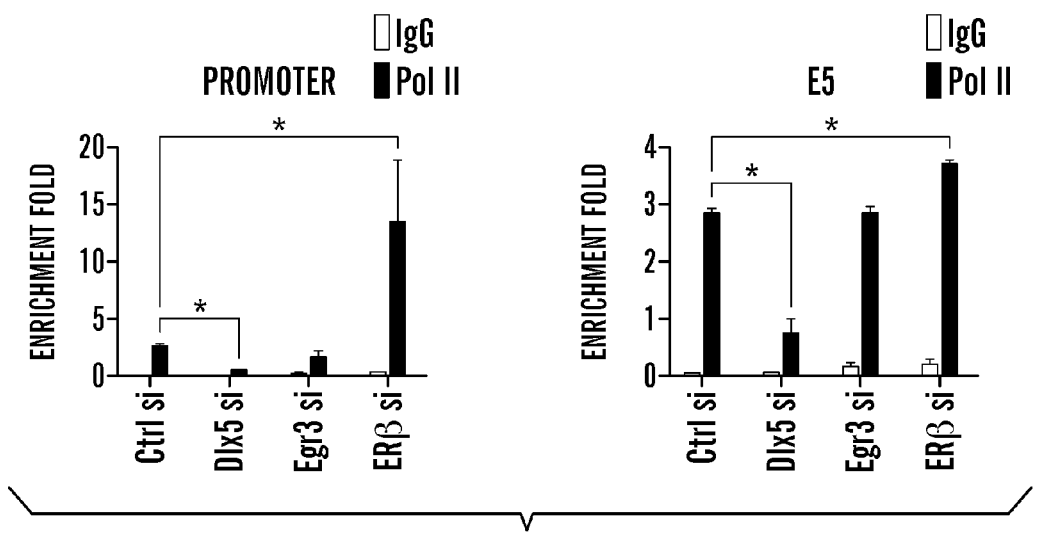
Figure 13D:
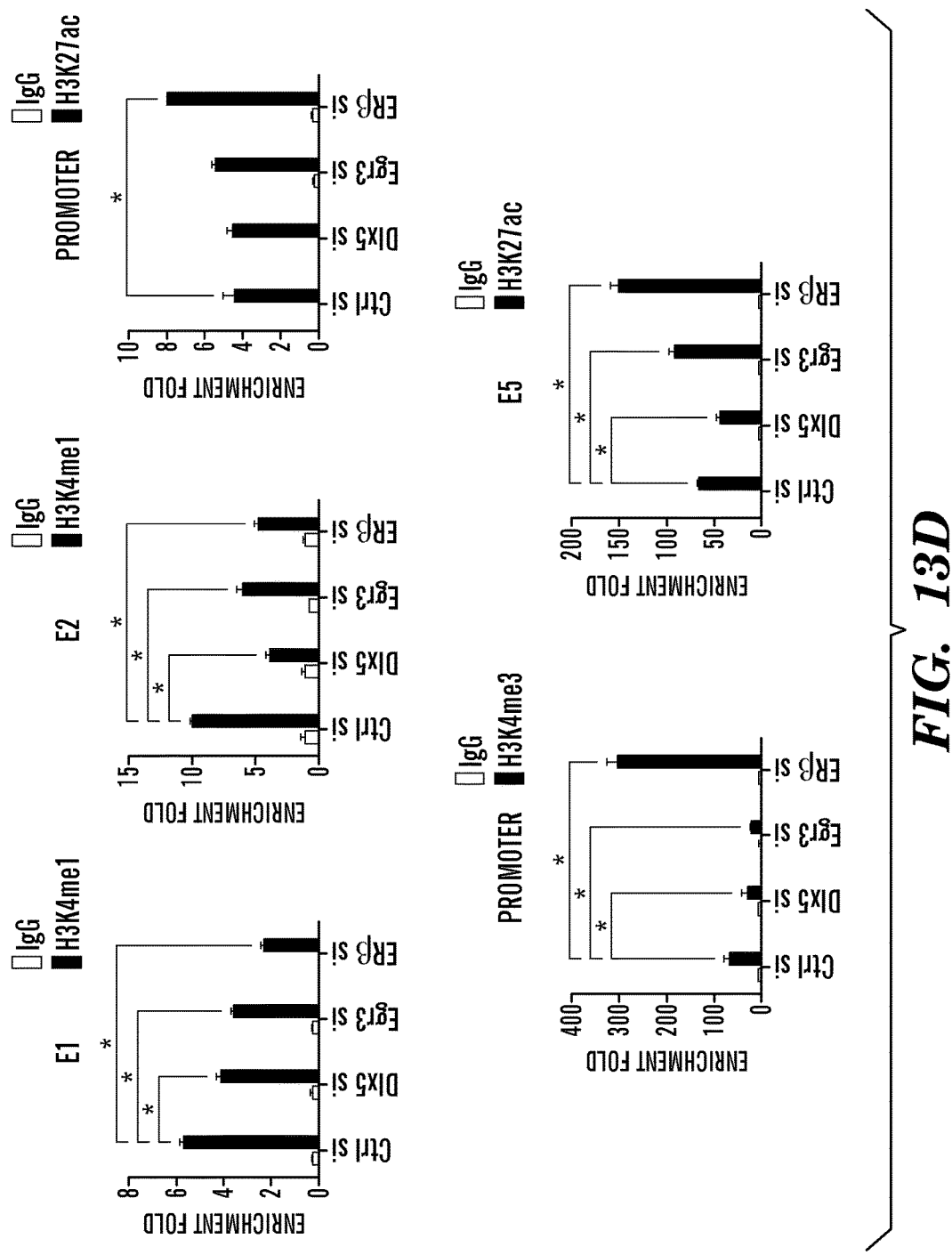

FIGS. 13A-13D demonstrate the essential role of Egr3, Dlx5 and ERß in RNA Pol II recruitment to the Notch1 locus and/or pause release. FIG. 13A depicts HKCs transfected with siRNAs against Dlx5, Egr3, ERß versus scrambled controls utilized for the ChIP assays shown in FIG. 3B analyzed 96 h later by immunoblot of the indicated proteins. FIGS. 13B-13C depict ChIP analysis of HKCs under growing versus differentiating conditions (FIG. 13B) and in differentiating HKCs plus/minus Egr3, Dlx5 and ERß (FIG. 13C) for levels of polymerase II occupancy of the Notch1 locus. Conditions were the same as in FIGS. 3A and 3B, utilizing HKCs of a different origin (*p<0.05). FIG. 13D depicts ChIP analysis of activated histone marks at the indicated regions of the Notch1 locus in HKCs of different origin from those in FIG. 3C, plus/minus Egr3, Dlx5 and ERß knock-down. Data were similarly analyzed and plotted (*p<0.05).

Figure 14A:
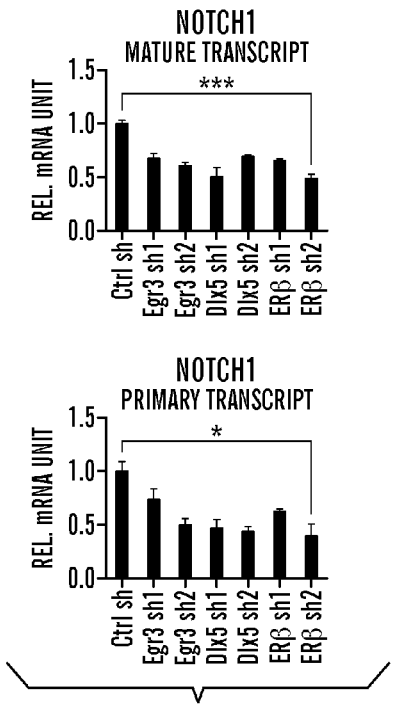
Figure 14B:
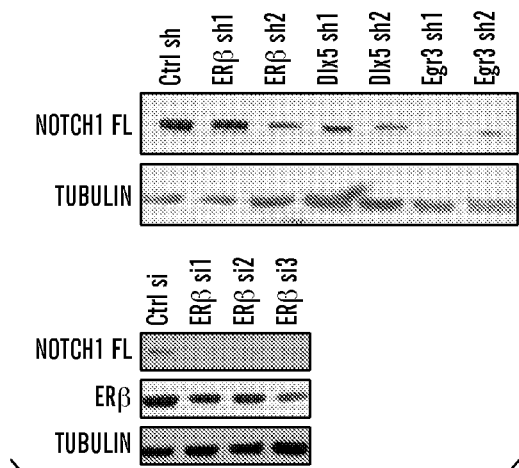
Figure 14C:
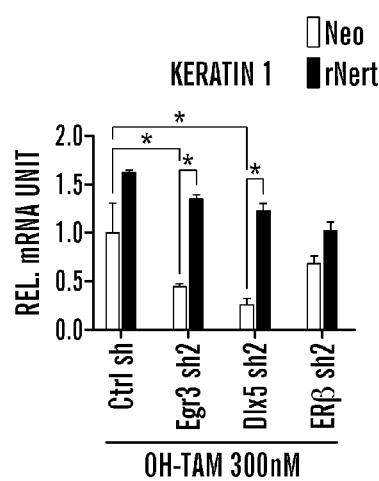
Figure 14C:
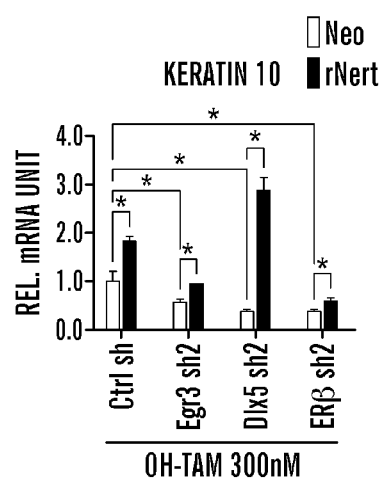

FIGS. 14A-14C demonstrate that Egr3, Dlx5 and ERß as regulators of Notch1 gene expression and function. FIG. 14A depicts parallel HKC cultures plus/minus shRNA-mediated knock down of the indicated genes as in FIG. 4A were analyzed by RT-qPCR for expression of the primary and mature Notch1 transcripts (*p<0.001). FIGS. 14B-14C depict similar experiments as the ones shown in FIGS. 4A-4B with HKCs of an independent origin. In FIG. 14B, lower panel, a similar immunoblot analysis of Notch 1 expression is shown for HKCs 3 days after transfection with 3 different siRNAs against ERß versus scrambled controls.

Figure 15A:
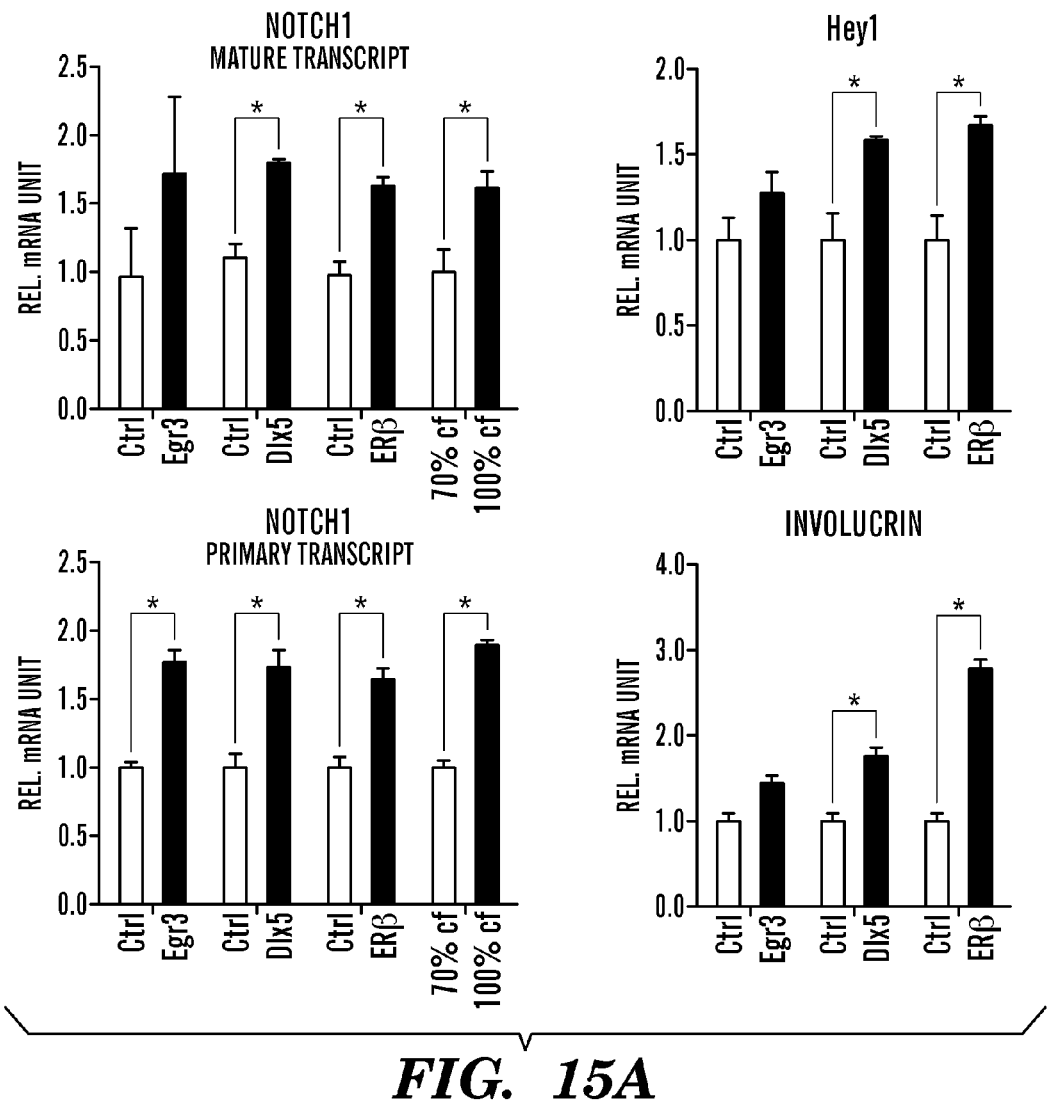
Figure 15B:
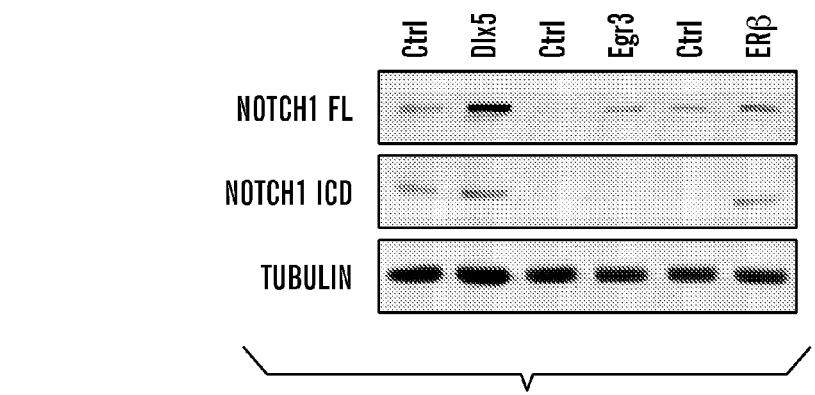

FIGS. 15A-15B demonstrate that Egr3, Dlx5 and ERß as regulators of Notch1 gene expression and function. FIG. 15A depicts parallel HKC cultures plus/minus retroviral-mediated expression of the indicated genes as in FIGS. 5A-5B were analyzed by RT-qPCR for expression of the primary and mature Notch1 transcripts using primers targeting the third intron/exon junction and junction between exon 32 and 33, respectively. The expression levels for canonical Notch target Hey1 and differentiation marker involucrin were also determined mRNA levels were normalized for 36134, and presented as fold-changes over control±S.D. (*p<0.001). FIG. 15B depicts HKCs of an independent origin plus/minus retroviral-mediated expression of genes as in FIG. 5A were similarly analyzed by immunoblotting.

Figure 16A:
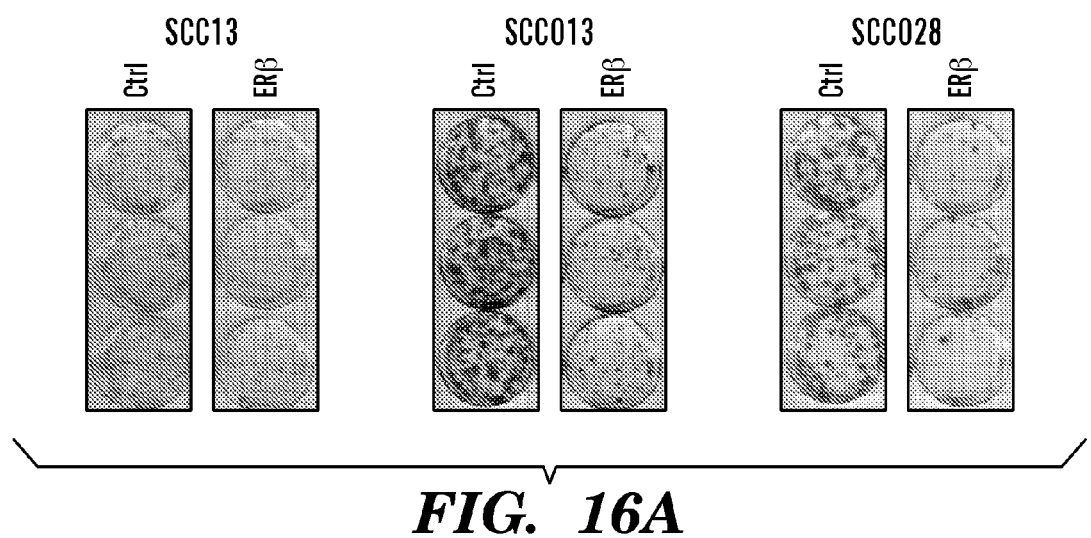
Figure 16B:
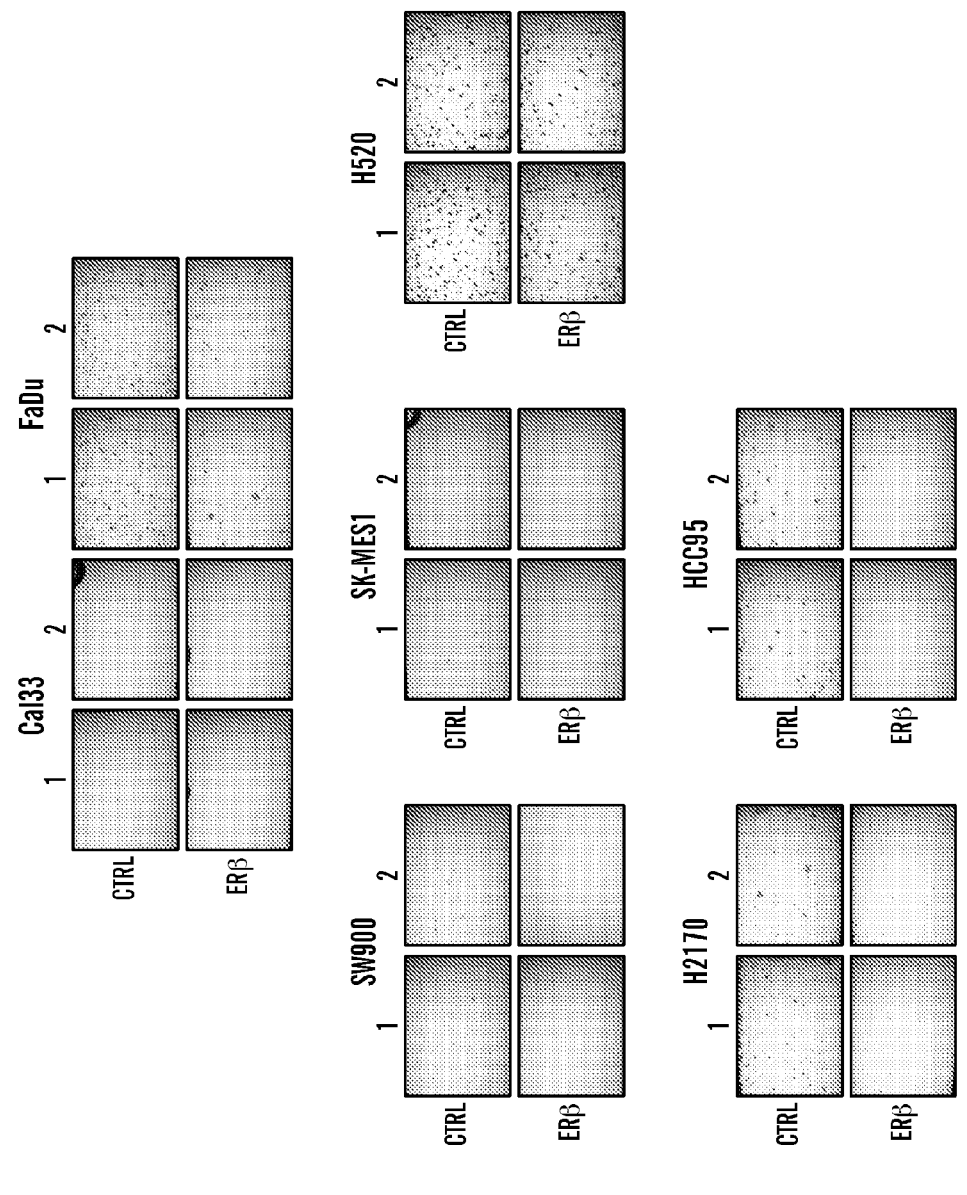

FIGS. 16A-16B demonstrate that increased ERβ level leads to reduced proliferation of SCC cells. FIG. 16A depicts whole dish images of colonies formed by the indicated SCC cells infected with an ERβ expressing lentivirus versus empty vector control. SCC13, SCCO13 and SCCO28 cells were plated at limited density on triplicate dishes (103 cells/60 mm dish) 96 hours after infection of lentiviruses and stained for colonies 10 days later. Images correspond to the experiment and colony quantification data shown in FIG. 8B. FIG. 16B depicts whole well images of spheroids formed by the indicated SCC cells infected with ERβ expressing versus control viruses. Stably infected cells were trypsinized and plated in 8-well chambers coated with matrigel at a density of 2000 cells/well in duplicates. Images correspond to the experiment and sphere quantification data shown in FIGS. 8C and 8D. Some SCC cell lines formed small size spheres that can be seen after magnification of the digital images.

FIGS. 17A-17B demonstrate that ERβ agonist treatment suppresses proliferation of SCC cells. FIG. 17A depicts whole well images of spheroids formed by the indicated SCCs treated with DPN versus DMSO control in FIG. 10A-10E. FIG. 17B depicts whole well images and quantification of spheroids formed by the indicated SCC cells treated with DPN versus DMSO control. SCC cells were trypsinized and plated in 8-well chambers coated with matrigel at a density of 2000 cells/well in duplicates. Data quantification is presented as mean of duplicates±S.D. n.s. stands for not significant.

Figure 18A:
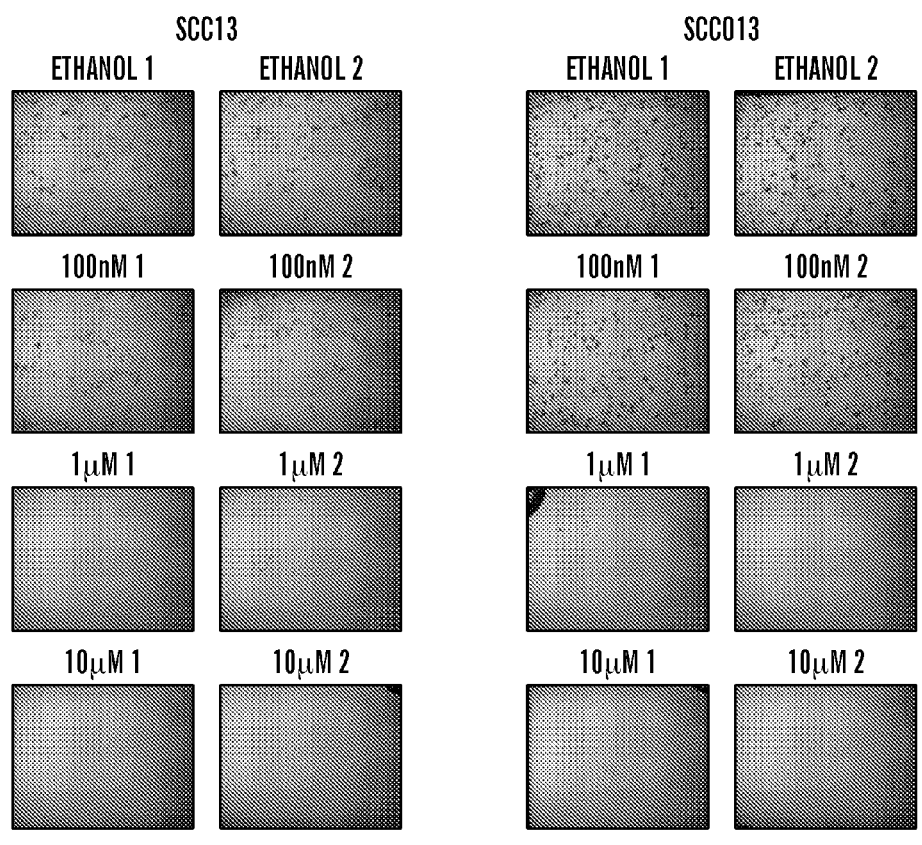
Figure 18A:
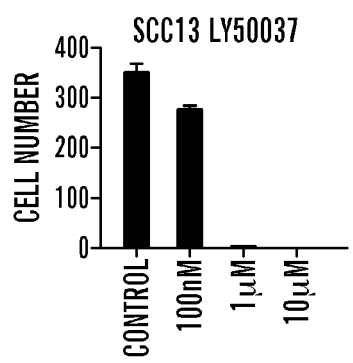
Figure 18A:
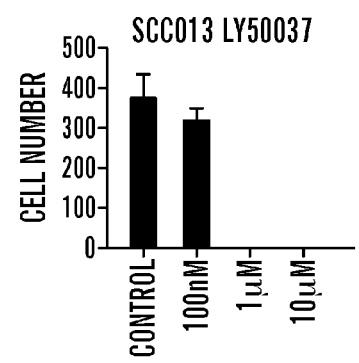
Figure 18B:
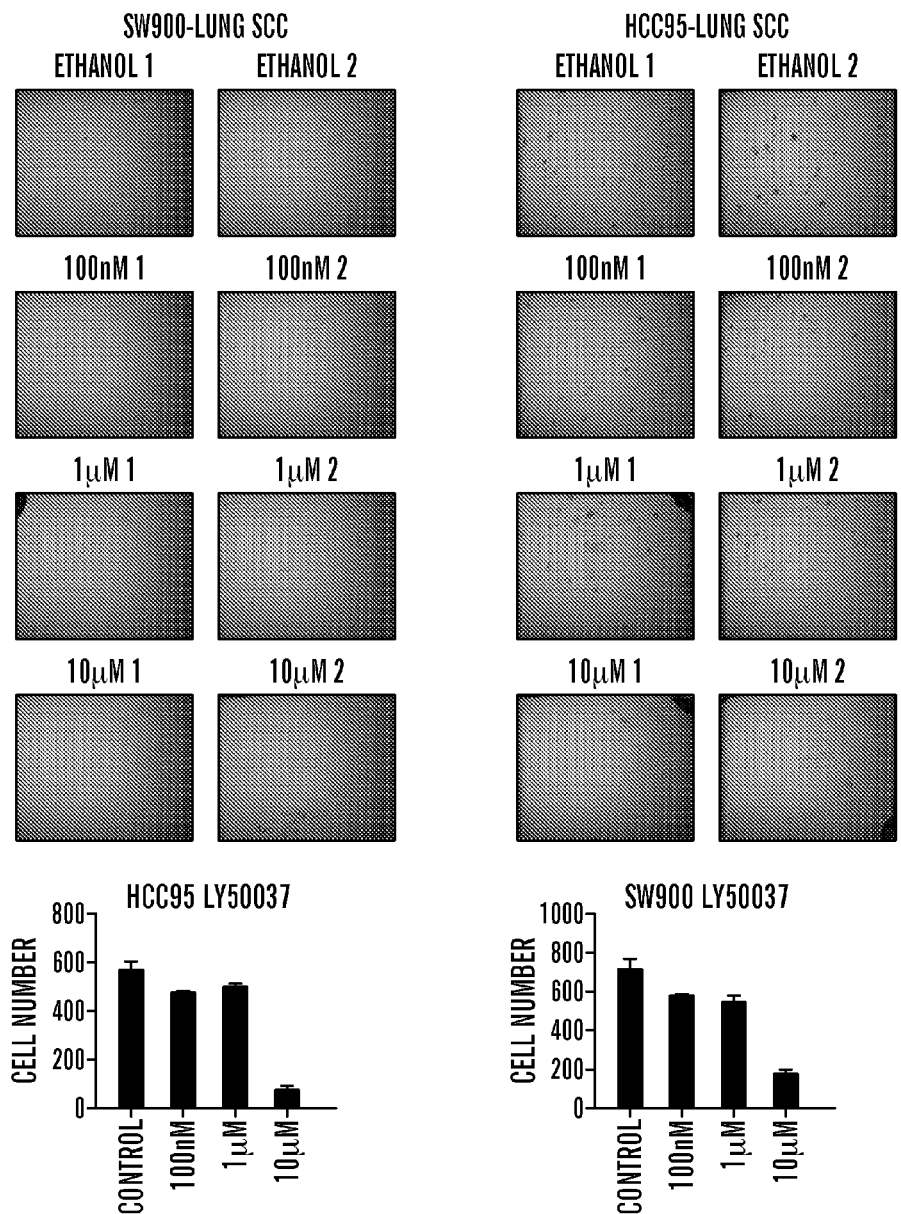
Figure 18C:
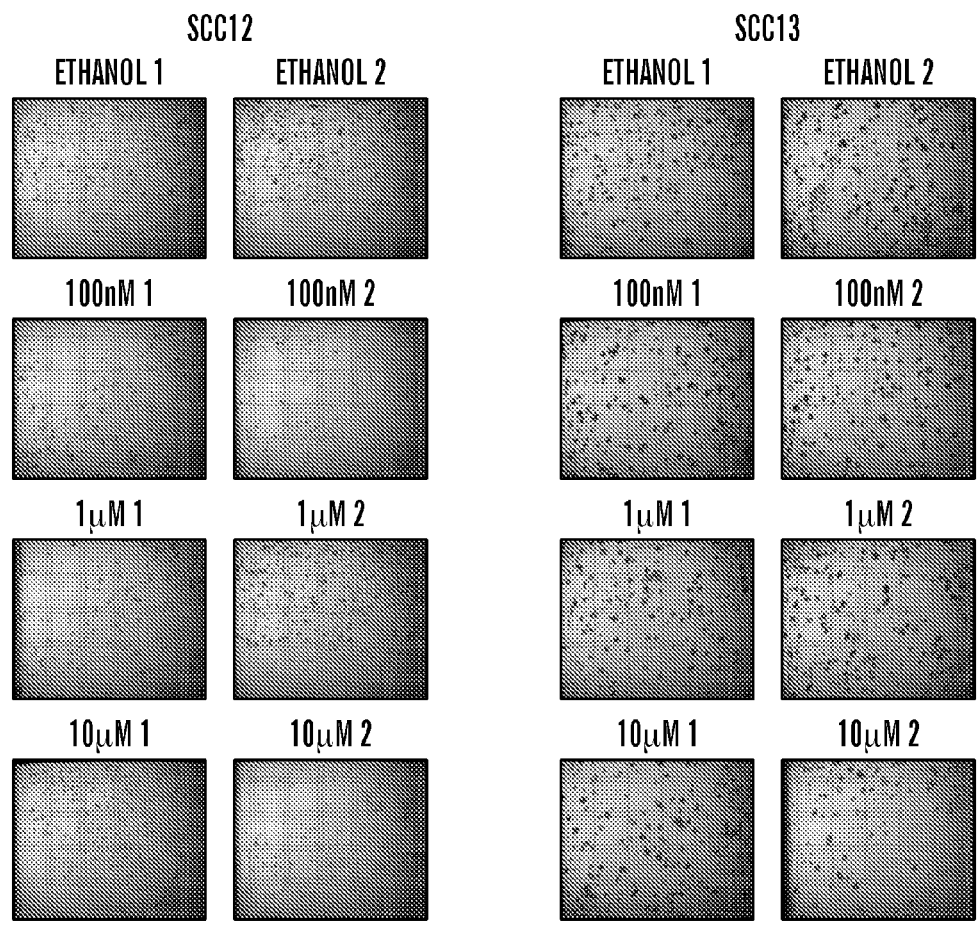
Figure 18C:
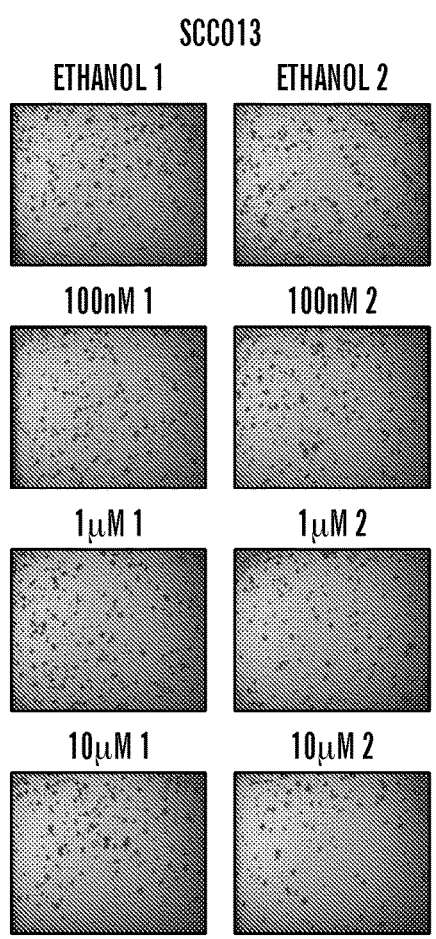
Figure 18C:
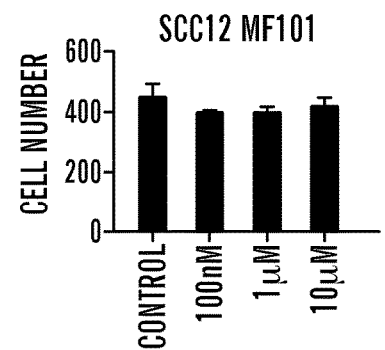
Figure 18C:
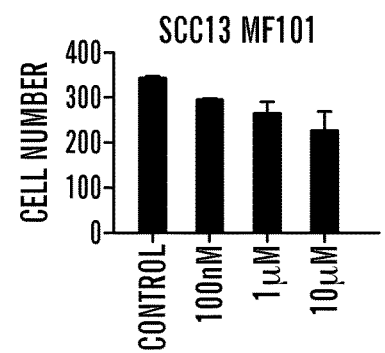
Figure 18C:
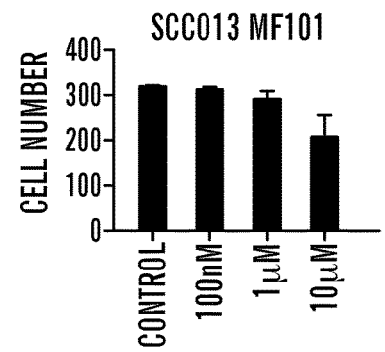

FIGS. 18A-18C demonstrate that ERβ agonist treatment suppresses proliferation of SCC cells in spheroid assays. FIG. 18A depicts suppression of skin and oral SCC cell line growth by LY50037. FIG. 18B depicts suppression of lung SCC cell line growth by LY50037. FIG. 18C depicts suppression of skin and oral SCC cell line growth by MF101.

DETAILED DESCRIPTION

Described herein is the inventors' discovery that NOTCH1 (NCBI Gene ID No: 4851) is activated by a number of genes disclosed in Table 1 and that agonists of those genes can increase the level and/or activity of NOTCH1. This upregulation of NOTCH1 inhibits the growth and proliferation of cancer cells, e.g. squamous cell carcinoma cells.

Accordingly, in one aspect, described herein is a method of inhibiting the growth and/or proliferation of a cancer cell, the method comprising contacting the cell with an agonist of a gene selected from Table 1. In some embodiments, contacting the cell with an agonist of a gene selected from Table 1 increases the level and/or activity of NOTCH1. In some embodiments, described herein is a method of inhibiting the growth and/or proliferation of a cancer cell, the method comprising contacting the cell with an agonist of Esr2 (e.g., ERβ).

TABLE 1

List of genes included in the siRNA library and the location of their putative binding sites in the regulatory regions of the Notch1 gene locus.

| RefSeq Accession Number | Gene Symbol | Full Gene Name | Gene ID | Predicted binding sites in the regulatory regions |
|---|---|---|---|---|
| NM_002585 | PBX1 | pre-B-cell leukemia homeobox 1 | 5087 | E1, E2, E4, E5, |
| NM_001042539 | MAZ | MYC-associated zinc finger protein (purinebinding transcription factor) | 4150 | E1, E2, P, E3, E5, E6, E7, E8, E9 |
| NM_003998 | NFKB1 | nuclear factor of kappa light polypeptide gene enhancer in B-cells 1 | 4790 | E2, P, E3, E4, E5, E6, E7, E8, E9 |
| NM_005269 | GLI1 | glioma-associated oncogene homolog 1 (zinc finger protein) | 2735 | E1, E2, P, E3, E6, E8, E9 |
| NM_002908 | REL | v-rel reticuloendotheliosis viral oncogene homolog (avian) | 5966 | E2, P, E3, E4, E5, E6, E7, E8, E9 |
| NM_001530 | HIF1A | hypoxia-inducible factor 1, alpha subunit (basic helix-loop-helix transcription factor) | 3091 | E1, E2, P, E5, E7, E8, E9 |
| NM_003593 | FOXN1 | forkhead box N1 | 8456 | E1, E2, P, E3, E7, E9 |
| NM_024865 | NANOG | Nanog homeobox | 79923 | E2, P, E3, E4, E5, E6, E7, E8, E9 |
| NM_000926 | PGR | progesterone receptor | 5241 | E1, P, E3, E4, E5 |
| NM_005859 | PURA | purine-rich element binding protein A | 5813 | P, E3, E4, E5, E7, E9 |
| NM_006599 | NFAT5 | nuclear factor of activated T-cells 5, tonicityresponsive | 10725 | E1, E2, P, E3, E4, E6, E7, E9 |
| NM_005270 | GLI2 | GLI-Kruppel family member GLI2 | 2736 | E1, E2, P, E3, E6, E8, E9 |
| NM_006286 | TFDP2 | transcription factor Dp-2 (E2F dimerization partner 2) | 7029 | E1, P, E6, E7 |
| NM_021813 | BACH2 | BTB and CNC homology 1, basic leucine zipper transcription factor 2 | 60468 | E1, E2, E3, E4, E5, E6, E7, E9 |
| NM_021632 | ZNF350 | zinc finger protein 350 | 59348 | E1, P, E3, E5, E6, E7, E8, E9 |
| NM_004430 | EGR3 | early growth response 3 | 1960 | P, E3 |
| NM_182907 | PRDM1 | PR domain containing 1, with ZNF domain | 639 | E1, E2, E3, E4, E5, E7, E9 |
| NM_003131 | SRF | serum response factor (c-fos serum response element-binding transcription factor) | 6722 | E1, E2, P, E3, E4, E5, E7, E8, E9 |
| NM_001621 | AHR | aryl hydrocarbon receptor | 196 | E2, E3, E4, E5, |

TABLE 1-continued

List of genes included in the siRNA library and the location of their
putative binding sites in the regulatory regions of the Notch1 gene locus.

| RefSeq Accession Number | Gene Symbol | Full Gene Name | Gene ID | Predicted binding sites in the regulatory regions |
|---|---|---|---|---|
| NM_002943 | RORA | RAR-related orphan receptor A | 6095 | E2, E7, E9 |
| NM_003200 | TCF3 | transcription factor 3 (E2A immunoglobulin enhancer binding factors E12/E47) | 6929 | E1, E2, E3, E4, E5, E7, E8, E9 |
| NM_014323 | PATZ1 | POZ (BTB) and AT hook containing zinc finger 1 | 23598 | E1, E2, P, E3, E4, E5, E6, E7, E8, E9 |
| NM_000125 | ESR1 | estrogen receptor 1 | 2099 | E1, E2, P E6, E7, E9 |
| NM_003153 | STAT6 | signal transducer and activator of transcription 6, interleukin-4 induced | 6778 | E1, E2, P, E3, E4, E5, E8, E9 |
| NM_021964 | ZNF148 | zinc finger protein 148 | 7707 | E1, E2, P, E3, E4, E5, E6, E7, E8, E9 |
| NM_014352 | POU2F3 | POU class 2 homeobox 3 | 25833 | P, E5, E7 |
| NM_016269 | LEF1 | lymphoid enhancer-binding factor 1 | 51176 | E2, P, E3, E4, E5, E6, E7, E8, E9 |
| NM_001040110 | NRF1 | nuclear respiratory factor 1 | 4899 | E2, P, E9 |
| NM_001040275 | ESR2 | estrogen receptor 2 (ER beta) | 2100 | E1, E2, P E6, E7, E9 |
| NM_000964 | RARA | retinoic acid receptor, alpha | 5914 | E1, E2, P, E3, E4, E5, E6, E7, E8, E9 |
| NM_152739 | HOXA9 | homeobox A9 | 3205 | E4, E5 |
| NM_004559 | YBX1 | Y box binding protein 1 | 4904 | E1, E2, P, E3, E4, E5, E7, E9 |
| NM_002653 | PITX1 | paired-like homeodomain 1 | 5307 | P, E9 |
| NM_005526 | HSF1 | heat shock transcription factor 1 | 3297 | E1, E2, P, E3, E4, E5, E6, E7, E8, E9 |
| NM_002460 | IRF4 | interferon regulatory factor 4 | 3662 | E2, P, E3, E4, E5, E7, E8, E9 |
| NM_001032280 | TFAP2A | transcription factor AP-2 alpha (activating enhancer binding protein 2 alpha) | 7020 | E2, P, E3, E4, E5, E7, E8, E9 |
| NM_002655 | PLAG1 | pleiomorphic adenoma gene 1 | 5324 | E1, E2, P, E3, E4, E5, E6, E7, E8, E9 |
| NM_030751 | ZEB1 | zinc finger E-box binding homeobox 1 | 6935 | E1, E2, P, E3, E4, E5, E6, E7, E9 |
| NM_001003688 | SMAD1 | SMAD family member 1 | 4086 | E2, P, E5, E7, E9 |
| NM_003422 | MZF1 | myeloid zinc finger 1 | 7593 | E1, E2, P, E3, E4, E5, E6, E7, E8, E9 |
| NM_005221 | DLX5 | distal-less homeobox 5 | 1749 | E1, P |
| NM_005524 | HES1 | hairy and enhancer of split 1, (Drosophila) | 3280 | E1, P, E3, E5, E7, E8, E9 |
| NM_000966 | RARG | retinoic acid receptor, gamma | 5916 | E1, E2, P, E3, E4, E5, E6, E7, E8, E9 |
| NM_002198 | IRF1 | interferon regulatory factor 1 | 3659 | E2, P, E3, E4, E5, E6, E7, E8, E9 |
| NM_001964 | EGR1 | early growth response 1 | 1958 | E1, E2, P, E3, E5, E7, E8, E9 |
| NM_002196 | INSM1 | insulinoma-associated 1 | 3642 | E1, E2, P, E3, E4, E5, E6, E7, E8, E9 |
| NM_006186 | NR4A2 | nuclear receptor subfamily 4, group A, member 2 | 4929 | E1, P, E7, E9 |
| NM_005225 | E2F1 | E2F transcription factor 1 | 1869 | E1, E2, P, E3, E4, E5, E6, E8, E9 |
| NM_000346 | SOX9 | SRY (sex determining region Y)-box 9 (campomelic dysplasia, autosomal sexreversal) | 6662 | E1, E2, P, E3, E5, E7, |
| NM_001668 | ARNT | aryl hydrocarbon receptor nuclear translocator | 405 | E3, E4, E5, E8 |
| NM_000044 | AR | androgen receptor | 367 | E1, E2, P, E3, E4, E5, E6, E7, E8, E9 |
| NM_002382 | MAX | MYC associated factor X | 4149 | E6, E9 |
| NM_001913 | CUX1 | cut-like homeobox 1 | 1523 | E1, E2, P, E4, E5, E7, E9 |
| NM_030762 | BHLHB3 | basic helix-loop-helix domain containing, class B, 3 | 79365 | E1, E2, P, E3, E4, E5, E6, E7, E9 |
| NM_000168 | GLI3 | GLI-Kruppel family member GLI3 (Greig cephalopolysyndactyly syndrome) | 2737 | E1, E2, P, E3, E5, E6, E7, E8, E9 |
| NM_015069 | ZNF423 | zinc finger protein 423 | 23090 | E1, E2, P, E3, E5, E6, E7, E9 |
| NM_003150 | STAT3 | signal transducer and activator of transcription 3 (acute-phase response factor) | 6774 | E1, E2, P, E3, E4, E5, E6, E7, E9 |

TABLE 1-continued

List of genes included in the siRNA library and the location of their putative binding sites in the regulatory regions of the Notch1 gene locus.

| RefSeq Accession Number | Gene Symbol | Full Gene Name | Gene ID | Predicted binding sites in the regulatory regions |
|---|---|---|---|---|
| NM_002701 | POU5F1 | POU class 5 homeobox 1 | 5460 | E1, E2, P, E3, E5, E7, E9 |
| NM_021953 | FOXM1 | forkhead box M1 | 2305 | P, E3, E4, E5, E6, E9 |
| NM_000376 | VDR | vitamin D (1,25-dihydroxyvitamin D3) receptor | 7421 | E1, E2, P, E3, E4, E5, E6, E7, E8, E9 |

As used herein, the term "agonist" refers to any agent that increases the level and/or activity of the target, e.g, of Esr2, Dlx5, or Egr3. As used herein, the term "agonist" refers to an agent which increases the expression and/or activity of the target by at least 10% or more, e.g. by 10% or more, 50% or more, 100% or more, 200% or more, 500% or more, or 1000% or more. Non-limiting examples of agonists of a given target can include target polypeptides or fragments thereof and nucleic acids encoding a target polypeptide. In some embodiments, the agonist can be a nucleic acid encoding the gene or a vector comprising such a nucleic acid. In some embodiments, the agonist can be a small molecule.

The level and/or activity of any of the targets of Table 1 can be determined, e.g. by measuring the level of a gene product, the level of a Notch1 gene product, Notch1 activity levels, and tumor suppression activity. Suitable, non-limiting antibodies, primers, and protocols for such assays are provided in the Examples herein.

The nucleic acid and polypeptide sequences of the genes of Table 1 are readily obtained from the NCBI database using the provided Gene ID numbers.

In some embodiments, the gene is selected from the group consisting of Esr2; Dlx5; and Egr3.

In some embodiments, the agonist of Esr2 (e.g. an agonist of ERbeta, encoded by the Esr2 gene) can be 17β-estradiol (E2); 2,3-bis(4-Hydroxyphenyl)-propionitrile (DPN); LY50037; liquiritigenin; MF101; 17β-estradiol (E2); 2,3-bis(4-Hydroxyphenyl)-propionitrile (DPN); LY50037; liquiritigenin; MF101 (MENERBA); WAY20070; YA-202196; WAY-214156; ERB041; FERb033; (S)-Equol; diarylpropionitrile; AC74131; silybinin; genistein; AC-186; KB9520; ERB-79; GTx-822; silymarin; EVIENDEP™; and epigallocatechin gallate (EGCG). Esr2 agonists and methods of making the same are described, e.g., in International Patent Publications WO 00/47603; WO 01/32680; WO 01/77139; WO 00/63228; WO 97/08188; WO 99/63973; WO 12/037261; WO 06/044176; WO 00/001716; WO 10/003700; WO 07/014273; WO 10/050916; WO 04/094400; WO 05/082880; and WO 02/051821; and Japanese Patent Publication 11292872; each of which is incorporated by reference herein in its entirety. In some embodiments, the agonist of Esr2 can be an Esr2-specific agonist. In some embodiments, the agonist of Esr2 can be a pan-Esr agonist, e.g. an agonist of Esr2 and Esr1.

In one aspect, described herein is a method of treating cancer, the method comprising administering an agonist of a gene selected from Table 1. In some embodiments, described herein is a method of treating cancer, the method comprising administering an agonist of Dlx5, Egr3 and/or Esr2. In some embodiments, described herein is a method of treating cancer, the method comprising administering an agonist of Esr2 (e.g. ERβ). In some embodiments, the cancer is a carcinoma. In some embodiments, the cancer is squamous cell carcinoma. As used herein, the term "carcinoma" refers to a cancer arising from epithelial cells. As used herein, "squamous cell carcinoma" or "SCC" refers to a cancer arising from squamous epithelial cells. In some embodiments, the squamous cell carcinoma is located in the skin, head, neck, or lung.

In some embodiments, the methods described herein relate to treating a subject having or diagnosed as having squamous cell carcinoma with an agonist as described herein. Subjects having squamous cell carcinoma can be identified by a physician using current methods of diagnosing SCC. Symptoms and/or complications of SCC which characterize these conditions and aid in diagnosis are well known in the art and include but are not limited to, scaly or patches of skin and sores. Tests that may aid in a diagnosis of, e.g. SCC include, but are not limited to, biopsy. A family history of SCC, or exposure to risk factors for SCC (e.g. skin infection, injuries, or sun exposure) can also aid in determining if a subject is likely to have SCC or in making a diagnosis of SCC.

The compositions and methods described herein can be administered to a subject having or diagnosed as having, e.g. squamous cell carcinoma (SCC). In some embodiments, the methods described herein comprise administering an effective amount of compositions described herein, e.g. an agonist as described herein to a subject in order to alleviate a symptom of a SCC. As used herein, "alleviating a symptom of a SCC" is ameliorating any condition or symptom associated with the SCC. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

In some embodiments, the agonist as described herein is administered topically. In some embodiments, the agonist as described herein is administered orally.

The term "effective amount" as used herein refers to the amount of an agonist as described herein needed to alleviate at least one or more symptom of the disease or disorder, and relates to a sufficient amount of pharmacological composition to provide the desired effect. The term "therapeutically effective amount" therefore refers to an amount of the agonist that is sufficient to provide a particular anti-cancer effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for cell growth and/or proliferation among others. The dosage can be determined by a physician and adjusted, as necessary, to suit observed effects of the treatment.

In some embodiments, the technology described herein relates to a pharmaceutical composition comprising an agonist as described herein as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. an agonist as described herein.

In some embodiments, the pharmaceutical composition comprising an agonist as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of an agonist as described herein are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of the agonist as disclosed herein can also be incorporated into the parenteral dosage forms of the disclosure, including conventional and controlled-release parenteral dosage forms.

Pharmaceutical compositions comprising an agonist as described herein can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the an agonist as described herein can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. Non-limiting examples of a second agent and/or treatment can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

In certain embodiments, an effective dose of a composition comprising an agonist as described herein as described herein can be administered to a patient once. In certain embodiments, an effective dose of a composition comprising an agonist as described herein can be administered to a patient repeatedly. For systemic administration, subjects can be administered a therapeutic amount of a composition comprising an agonist as described herein, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. cell growth and/or tumor size by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an agonist as described herein can be administered over a period of time, such as over a 5 minute, 10 minute, 15 minute, 20 minute, or 25 minute period.

The dosage ranges for the administration of an agonist as described herein, according to the methods described herein depend upon, for example, the form of an agonist as described herein, its potency, and the extent to which symptoms, markers, or indicators of a condition described herein are desired to be reduced, for example the percentage reduction desired for tumor size. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of an agonist as described herein in, e.g. the treatment of a condition described herein, or to induce a response as described herein (e.g. inhibition of cell growth and/or proliferation) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. tumor size. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. tumor size or cell growth). It is well within the ability of one skilled in the art to monitor efficacy of administration and/or treatment by measuring any one of such parameters, or any combination of parameters. Efficacy can be assessed in animal models of a condition described herein, for example treatment of murine models of cancer. When using an experimental animal model, efficacy of treatment is evidenced when a statistically significant change in a marker is observed, e.g. a change in the rate of tumor growth or size.

In vitro and animal model assays are provided herein which allow the assessment of a given dose of an agonist as described herein. By way of non-limiting example, the effects of a dose of an agonist can be assessed by spheroid assay. A non-limiting example of a protocol for such an assay is as follows: 8-well chamber slides are coated with matrigel (BDbiosciences, CA; 50 µl per well) and incubated at 37° C. for 20 minutes to allow matrigel to polymerize. SCC cells are brought into suspension in normal culture medium plus 1% matrigel (7000 cells/ml) and added in triplicates to the pre-coated chamber slides (300 µl of cell mixture per well). Medium is refreshed every other day. An agonist is added to the medium and cell growth and proliferation measured over time, e.g. by microscopy.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cancer, e.g. squamous cell carcinoma. A subject can be male or female.

A subject can be one who has been previously diagnosed with or identified as suffering from or having a condition in need of treatment (e.g. SCC) or one or more complications related to such a condition, and optionally, have already undergone treatment for SCC or the one or more complications related to SCC. Alternatively, a subject can also be one who has not been previously diagnosed as having SCC or one or more complications related to SCC. For example, a subject can be one who exhibits one or more risk factors for SCC or one or more complications related to SCC or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

In some embodiments, a nucleic acid encoding an agonist as described herein is comprised by a vector. In some of the aspects described herein, a nucleic acid sequence encoding an agonist as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence that is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding an agonist as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, the terms "treat" "treatment" "treating," or "amelioration" refer to therapeutic treatments, wherein the object is to reverse, alleviate, ameliorate, inhibit, slow down or stop the progression or severity of a condition associated with a disease or disorder, e.g. SCC. The term "treating" includes reducing or alleviating at least one adverse effect or symptom of a condition, disease or disorder associated with SCC. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of inhibiting the growth and/or proliferation of a cancer cell, the method comprising contacting the cell with an agonist of a gene selected from Table 1.
2. The method of paragraph 1, wherein the level and/or activity of NOTCH1 is increased.
3. A method of treating cancer, the method comprising administering an agonist of a gene selected from Table 1.
4. The method of any of paragraphs 1-3, wherein the agonist is a nucleic acid encoding the gene.
5. The method of any of paragraphs 1-4, wherein the gene is selected from the group consisting of:
   Esr2; Dlx5; and Egr3.
6. The method of any of paragraphs 1-5, wherein the agonist of Esr2 is selected from the group consisting of: 17β-estradiol (E2); 2,3-bis(4-Hydroxyphenyl)-propionitrile (DPN); LY50037; liquiritigenin; MF101 (MENERBA); WAY20070; YA-202196; WAY-214156; ERB041; FERb033; (S)-Equol; diarylpropionitrile; AC74131; silybinin; genistein; AC-186; KB9520; ERB-79; GTx-822; silymarin; EVI-ENDEP™; and epigallocatechin gallate (EGCG).
7. The method of paragraph 1-6, wherein the cancer is a carcinoma.
8. The method of paragraph 7, wherein the cancer is squamous cell carcinoma.
9. The method of paragraph 8, wherein the squamous cell carcinoma is located in the skin, head, neck, or lung.
10. The method of any of paragraphs 1-9, wherein the agonist is administered topically.
11. The method of any of paragraphs 1-10, wherein the agonist is administered orally.

EXAMPLES

Example 1: ERß in Multifactorial Control of Notch1 Gene Transcription, Squamous Cell Differentiation and Cancer A squamous cell differentiation network centered on the Notch1 gene has emerged as key in suppression of squamous cell carcinoma (SCC) in skin and internal organs. Notch control is best understood at level of receptor activation. Regulation of Notch1 gene transcription, a still neglected area is examined herein. By bioinformatic and functional screening approaches several novel regulators of this gene were identified, with three playing a direct positive role in differentiating keratinocytes. The Dlx5 and Egr3 transcription factors are required for RNA PolII recruitment to the Notch1 locus, while estrogen receptor ß (ERβ), whose biological and biochemical functions are much less established than ERα, controls Notch1 transcription through RNA PolII pause release. Expression of several Notch1 regulators that are identified herein, including ERß, is frequently compromised in skin, head/neck and lung SCCs and SCC-derived cell lines. The ERß involvement is of likely clinical significance, as a keratinocyte ERß-dependent program of gene expression is subverted in SCCs from various body sites and significant differences exist in the mutational and gene expression signatures of head/neck and lung SCCs of female versus male patients. Directly increased ERß expression or pharmacological treatments with ERß agonists inhibit proliferation potential of several SCC cell lines, promoting Notch1 expression and squamous differentiation both in vitro and in vivo. Thus, transcriptional control of Notch1 expression and estrogen response are linked in keratinocytes, with possibly important implications for differentiation therapy of squamous cancer.

Squamous cell carcinomas (SCCs) are the most common form of human solid tumors and major cause of cancer lethality. These highly heterogeneous tumors arise from closely interconnected epithelial cell populations with substantially different self-renewal potential and a highly synchronized program of stratified differentiation. Notch signaling plays a pivotal role in diverse developmental, physiological and pathological processes (1). Among the four known Notch receptors, Notch1 plays the most significant role in squamous cell differentiation (2). Recent whole genome sequencing studies identified recurrent loss-of-function mutations of the Notch1 gene in head and neck, cutaneous and lung SCCs (3-5), consistent with the tumor suppressing function that Notch1 activation can play in this tumor type (6). Most attention has been given to its opposite tumor promoting function in other malignancies, like T cell leukemia (T-ALL) (7) and breast cancer (8). While current drug development attempts are focused on inhibiting Notch signaling, it would also be desirable to identify approaches for activation of this pathway for possible differentiation-based therapy of squamous cancer.

Control of Notch1 activity has been highly studied at the level of receptor processing and activation, while surprisingly little is known on direct transcription control of the Notch1 gene (1). Notch1 is a direct p53 target in keratinocytes and its down-modulation in keratinocyte-derived tumors can be explained, in part, by mutation or down-modulation of p53 expression (9, 10). In most cells, with the notable exception of T cells (11), transcription of the human Notch1 gene is driven by a single TATA-less "sharp peak" promoter that, in human keratinocytes, is under synergistic negative control of KLF4 and Sp3 (12). A related but more complex mode of regulation has been reported in human esophageal cancer cells, in which Notch1 transcription appears to be under positive KLF5 control as a compensatory mechanism to compromised p53 function (13). A few other transcription factors have been reported to control Notch1 transcription in different cell types, including Ovol2 (14), FOXN1 (15), STAT3 (16), E2A (17), NF-κB (18) and HIF1α (18). While these studies were focused on involvement of individual transcription factors, to the best of our knowledge, no studies have been undertaken to probe into transcription control of the Notch1 locus in a more systematic manner.

By a combined bioinformatic and functional screening approach, described herein is the identification of three novel direct regulators of the Notch1 gene, Dlx5, a homeobox protein best known for its role in proximal-distal limb development (19), Egr3, an immediate early response gene involved in neuronal plasticity (20), and estrogen receptor β (ERβ), whose biological and biochemical functions are much less established than its cousin ERα (21). Altered estrogen signaling is involved in development of a number of cancers, including breast, ovarian, colorectal, prostate and endometrial cancers, and this pathway has been intensively investigated for pharmacological targeting (22). In breast cancer, there have been various reports on interplay between the Notch1 and estrogen/ERα signaling pathways at multiple levels ((23, 24) and refs. therein), but none on Notch1 as an ERα transcriptional target. Global gene expression analysis combined with ChIP-seq studies has revealed that ERα and ERβ have both common and distinct target genes (25). However, since most ERβ studies were generated using ectopically expressed protein, characterization of endogenous ERβ transcriptional function is still missing. Together with Egr3 and Dlx5, these findings establish ERβ as a direct positive regulator of Notch1 expression in keratinocytes and keratinocyte-derived SCC cells and point to this molecule as a therapeutic target for differentiation therapy treatment of SCC. In fact, ERβ expression and function, linked with Notch1-dependent differentiation, is frequently compromised in skin, head/neck and lung SCCs and increased ERβ expression or pharmacological treatments with ERβ agonists can suppress proliferation of SCC cells both in vitro and in vivo, while promoting Notch1 expression and differentiation.

Results

A transcription factor network involved in control of Notch1 gene expression in keratinocytes. To probe into transcription control of the Notch1 gene, the chromatin configuration of the human Notch1 locus in human primary keratinocytes (HKCs) was examined by utilizing whole genome information provided by the ENCODE consortium (available on the world wide web at genome.ucsc.edu/ENCODE/). Since insulator elements segregate genomic regulatory units, the Notch1 region delimited by peaks of ChIP-seq (Chromatin Immunoprecipitation Sequencing) was focused on for the insulator protein CTCF. Chromatin regions of likely regulatory function were focused on the basis of ChIP-seq peaks for modified histones present in enhancers and promoters. 60 transcription factors with putative binding sites within these regions were selected for functional screening on the basis of their conservation between rat, mouse and human and/or their epithelial pattern of expression in normal versus pathological conditions (as indicated by EST and cDNA microarray databases) (Table 1).

Figure 1A:
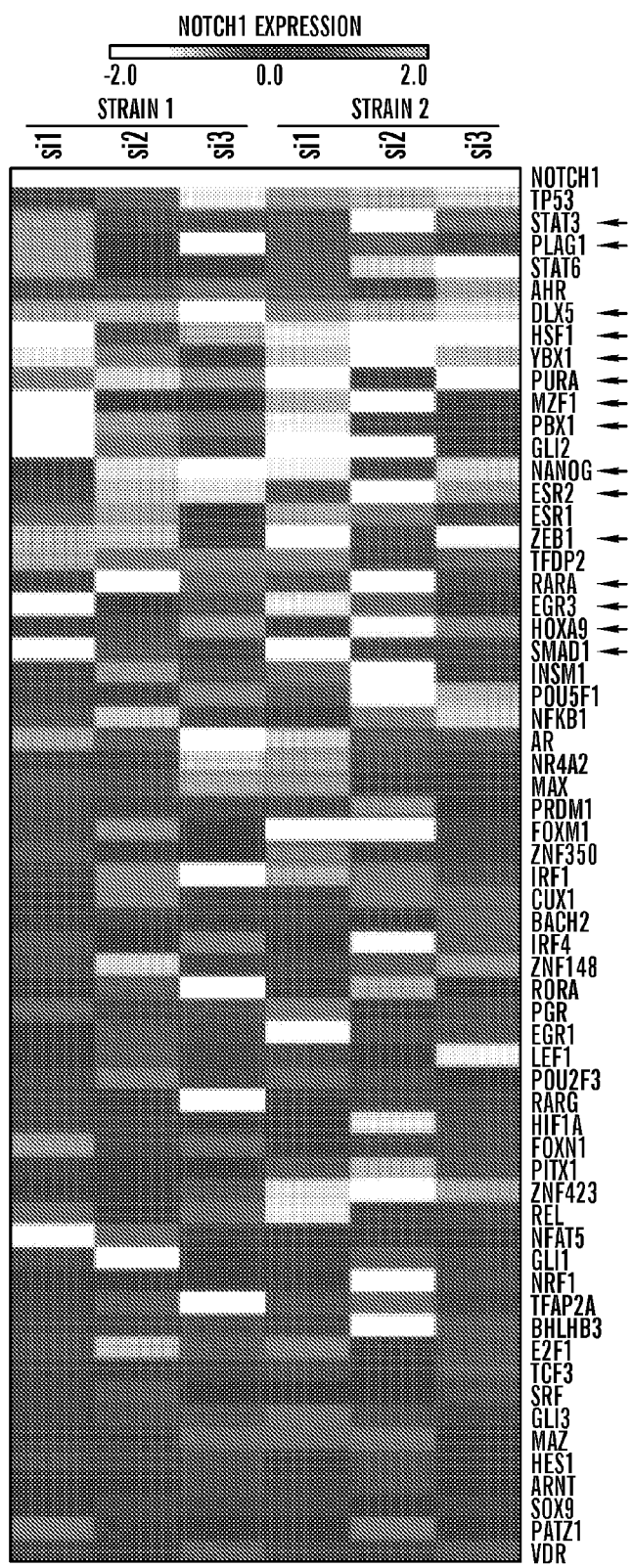
FIGS. 1A-1E demonstrate identification of transcription factors that control NOTCH1 expression in HKCs.
Figure 1B:
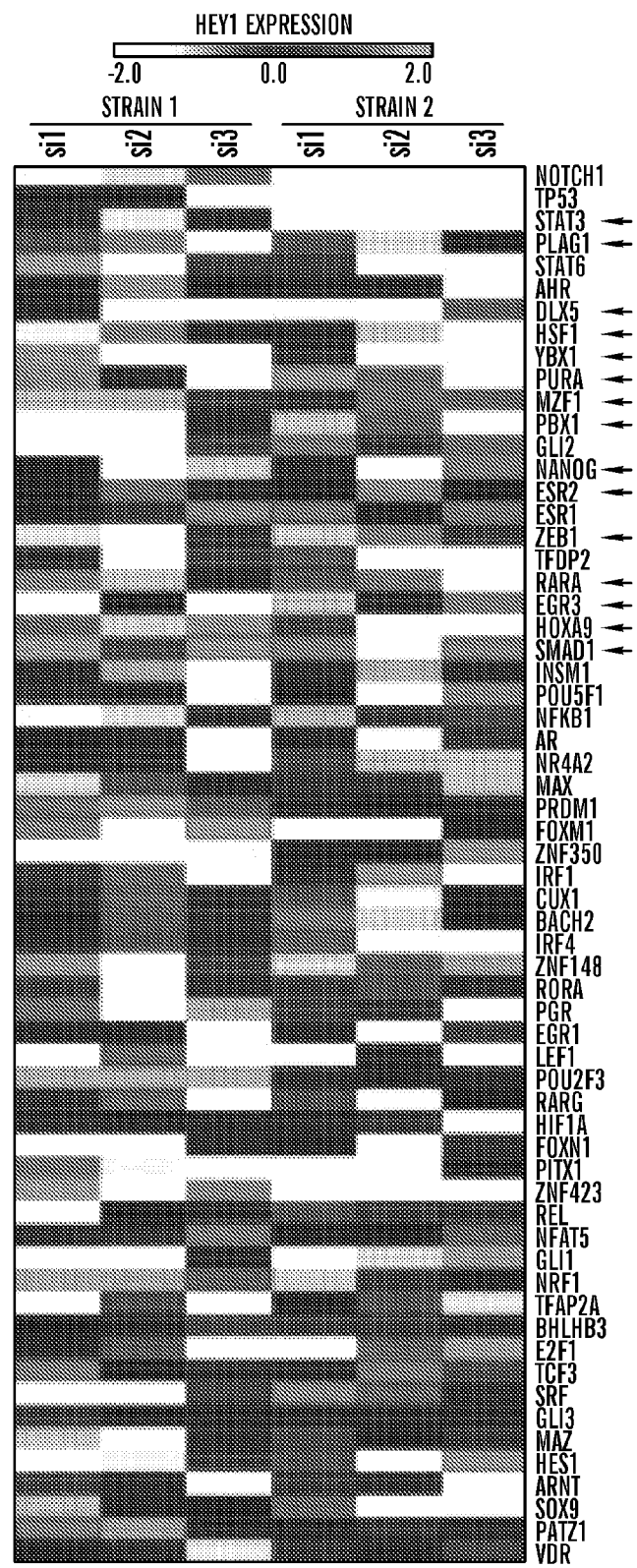
Figure 1C:
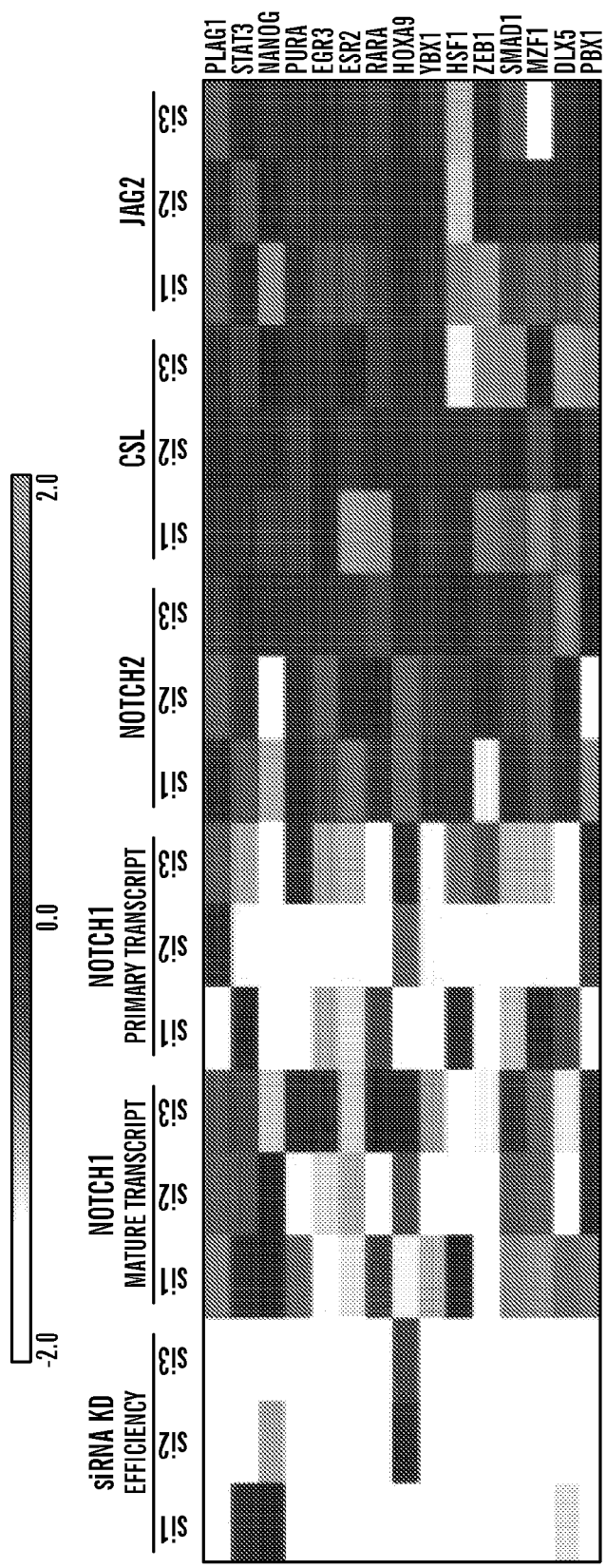

A custom-made siRNA library was utilized to knockdown expression of these genes in HKCs by reverse-transfection. The primary screen was performed twice, with 3 siRNAs per gene, utilizing two HKC strains of independent origin. For both screens, cells were collected one week post-transfection, i.e. under high density differentiating conditions associated with elevated Notch1 expression (9) to capture factors involved in Notch1 transcription activation. Successful assay conditions were verified by assessing the impact on Notch1 mRNA levels of siRNA-mediated knockdown of the Notch1 gene itself as well p53, as a known positive regulator of Notch1 expression (9) (FIGS. 1A-1B). In parallel with Notch1, expression of the "canonical target gene" Hey1 was assessed as an indicator of endogenous Notch activity (9). 15 genes with consistent knock-down mediated effects on Notch1 and Hey1 expression (>1.8 folds up- or down-modulation) in the two primary screens were further validated by siRNA knock-down in a third strain of HKCs (FIG. 1C). In parallel with the mature Notch1 mRNA, levels of the primary transcript (by qRT-PCR of the third exon-intron junction) as well as transcripts of other key components of the Notch pathway were assessed. Knock-down of Stat3, a tumor promoting gene in keratinocytes (26) ENREF 22, and Plag1, a gene of unknown function in keratinocytes with a versatile role in tumor development (27), caused up-regulation of the mature Notch1 mRNA and down-regulation of the primary transcript, implicating these genes in opposite control mechanisms of Notch1 transcription and mRNA stability (FIG. 1C). Knock-down of all other genes resulted in a similar down-regulation of both mature and primary Notch1 transcripts indicating that they function mostly at the level of transcription. Interestingly, expression of other Notch signaling components was differentially affected by silencing of the various genes, in many cases in an opposite manner to Notch1, indicating that expression of these various components can be genetically dissociated (FIG. 1C).

A common feature of transcription regulatory networks is the presence of positive and negative feedback loops used to amplify and dampen signals (28). To assess whether Notch1 regulators are themselves under Notch signaling control, their expression was evaluated in HKCs upon Notch1 knockdown or activation of the endogenous receptor by co-culture with fibroblasts expressing the Notch ligand Jagged-2. Expression of most genes did not change consistently in the two conditions, with the exception of Nanog and Zeb1 that, although lowly expressed, were found to be under positive Notch control (data not shown). Given its known role in control of Notch1 expression (9, 10), a potential interconnection between p53 and the identified Notch1 regulators was examined. Analysis of HKCs with p53 knock-down or stabilization of the endogenous p53 protein by Nutlin-3a treatment, showed only ZEB1 to be consistently modulated in both conditions (data not shown).

Egr3, Dlx5 and ERβ Activate Notch1 Gene Transcription During Differentiation.

Figure 1D:
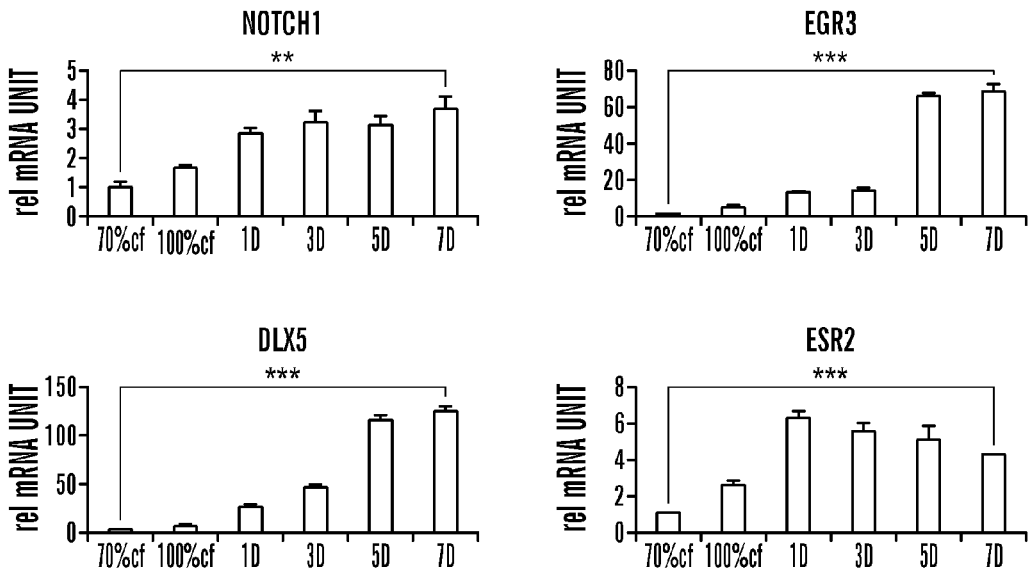
Figure 1E:
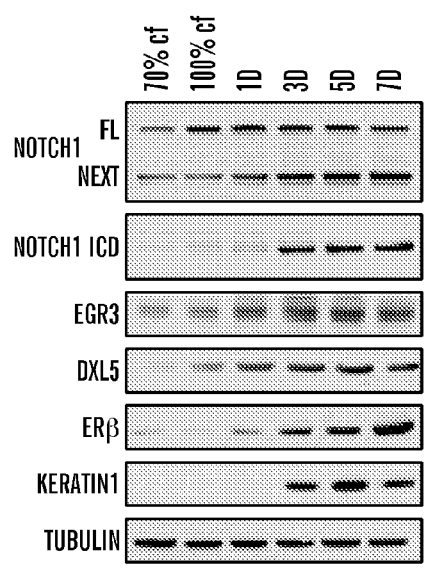

The transcription factors identified in the screen can fulfill two functions, i.e. be required for maintenance of sustained transcription and/or play a more direct positive role in control of the Notch1 gene. It was reasoned that transcription factors involved in positive control of Notch1 expression can be concordantly up-regulated with differentiation. Among the 15 Notch1 regulators, Egr3, Dlx5 and ERβ (encoded by the ESR2 gene) were consistently up-regulated during differentiation (FIGS. 1D, 1E). To assess whether these three factors participated directly in transcription control of the Notch1 gene, chromatin immunoprecipitation (ChIP) assays were performed with extracts of total human epidermis. The results showed binding of all three factors to the Notch1 locus at distinct regulatory regions: Egr3 was detected at a single enhancer region (E3) 6.5 kB upstream of the transcription start site (TSS), Dlx5 was found at the promoter region and a downstream enhancer (E1) and ERβ was detected at the promoter region (P) as well as upstream (E9) and downstream (E1, E2) enhancers, with apparently greater binding to the latter (FIGS. 2B and 12A). Similar ChIP assays were performed on HKCs in culture conditions that allowed study of the transition from proliferation to early steps of differentiation. This time-course analysis showed that the binding of these factors in HKCs underwent dynamic change from growing to differentiating conditions, with enhanced binding of the three factors to the corresponding regions of the Notch1 locus in differentiating HKCs. In these cells, Dlx5 was found to bind to the promoter region of the Notch1 gene but not to the downstream enhancer. Besides the upstream E3 enhancer, Egr3 binding to the Notch1 promoter region was also detected. ERβ was found at multiple regions of the Notch1 locus that overlapped to a large extent with those detected in the epidermis, plus additional upstream enhancers (E6, E7) (FIGS. 2C and 12B). Binding specificity of each factor was confirmed by ChIP analysis performed on high density differentiating HKCs plus/minus knock-down of Egr3, Dlx5, and ERβ expression (FIGS. 2D, 12C, and 13A).

Egr3 and Dlx5 are Required for RNA Pol II Recruitment to the Notch1 Locus, and ERβ for RNA Pol II Pause Release.

Figure 3A:
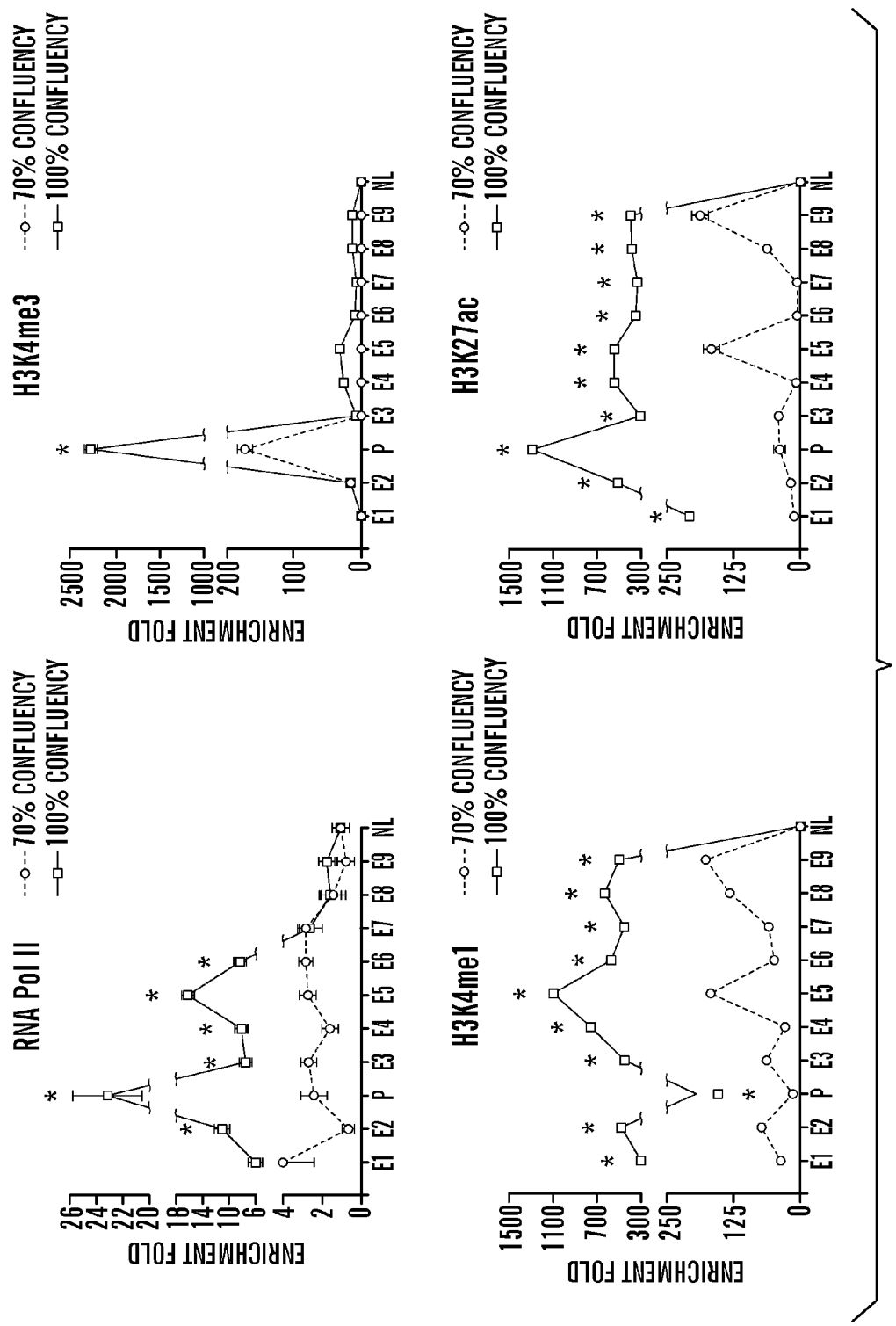

For further functional insights, growing versus differentiating keratinocytes were subjected to ChIP with antibodies against RNA polymerase II (PolII). PolII binding increased with differentiation not only at the promoter and downstream enhancer regions but also at some upstream enhancers (E3-E6), which can be interpreted as an indication of promoter-enhancer interactions and "chromosome looping" (29) (FIGS. 3A and 13B). PolII binding at promoter and enhancer regions was substantially decreased in differentiating HKCs in which Dlx5 and Egr3 genes were knocked-down (FIG. 3B). Knock-down of ERβ had more complex and unexpected consequences. In HKCs with ERβ down-modulation, binding of PolII to the downstream transcribed region of the Notch1 gene was, as expected, decreased, while binding to the promoter and two of the upstream enhancers (E4, E5) was increased rather than decreased (FIG. 3B and FIG. 13C). This indicates that presence of ERβ is required for progression of PolII through the transcribed downstream region and that, in its absence, PolII is still recruited to the gene, but kept in a paused state that is known to have also consequences on "looping" (30).

In genomic regions of active transcription or pausing, elevated PolII is associated with active chromatin configuration, whereas reduction in PolII recruitment leads to nucleosome reassembly and less open configuration (30). The Notch1 gene locus was therefore analyzed for histone marks of open chromatin configuration in HKCs plus/minus knockdown of the three regulators. ChIP assays with antibodies against histone modifications associated with activated promoter (H3K4me3 and H3K27ac) and enhancer (H3K4me1 and H3K27ac) regions showed, in differentiating keratinocytes, increased levels of H3K4me3 at the Notch1 promoter that was paralleled by a widespread increase of H3K4me1 and H3K27ac at enhancers (FIG. 3A). It was next assessed how levels of active histone marks were affected in differentiating keratinocytes by Dlx5, Egr3 or ERβ knockdown. Consistent with the suppression of Notch1 gene transcription, H3K4me1 levels at the downstream enhancers (E1 and E2) were decreased in Dlx5, Egr3, or ERβ knockdown cells (FIGS. 3C and 13C). Interestingly, at the promoter region, levels of H3K4me3 and H3K27ac, as signs of open configuration, were either decreased (H3K4me3) or unaffected (H3K27ac) in HKCs with Dlx5 and Egr3 knockdown, while they were substantially increased in HKCs with ERβ knock-down (FIGS. 3C and 13D). Substantially increased H3K27ac was also found at two upstream enhancer regions (E4 and E5) in HKCs with ERβ knockdown, which paralleled increased PolII binding even at these locations (FIGS. 3C and 13D). Repressive marks, such as H3K9me3 and H3K27me3, were not enriched at any of the regulatory regions (E1-E9) in either control or knockdown conditions, and levels of other modified histone marks (such as H3K4me1 and H3K9ac) were not consistently altered in the two different strains of HKCs that were tested (data not shown).

Dlx5 and ERβ Induce Keratinocyte Differentiation Through a Notch-Dependent Mechanism. Notch signaling plays an important pro-differentiation role in keratinocytes (2). To determine whether Egr3, Dlx5 and ERβ function as positive determinants of differentiation, several complementary approaches were undertaken. In the first, it was found that knockdown of these genes by lentiviral-mediated shRNA delivery caused, in parallel with decreased Notch1 expression, down-modulation of differentiation markers like Keratin 1 and 10, which was rescued to a large extent by exogenous activated Notch1 expression (FIGS. 4A, 4B, and 14A-14C). The impact on differentiation was further evaluated by assessing behavior of HKCs in skin organotypic cultures in which they undergo a vertical differentiation program closely approximating the one occurring in vivo (9). Even under these conditions, Dlx5, ERβ and Egr3 knockdown resulted in a significant reduction of Notch1 expression, as assessed by immunoblot analysis of proteins recovered from the reconstituted epidermis as well as by immunofluorescence analysis (FIG. 4C). Epidermal reconstitution capability of HKCs was not affected by Egr3 silencing, while knock-down of Dlx5 and, to a greater extent, ERβ resulted in a reduced number of stratified layers and defective cornification and terminal differentiation marker expression (data not shown), causing similar effects as those resulting from Notch inhibition in keratinocyte 3D cultures (31).

Figure 5A:
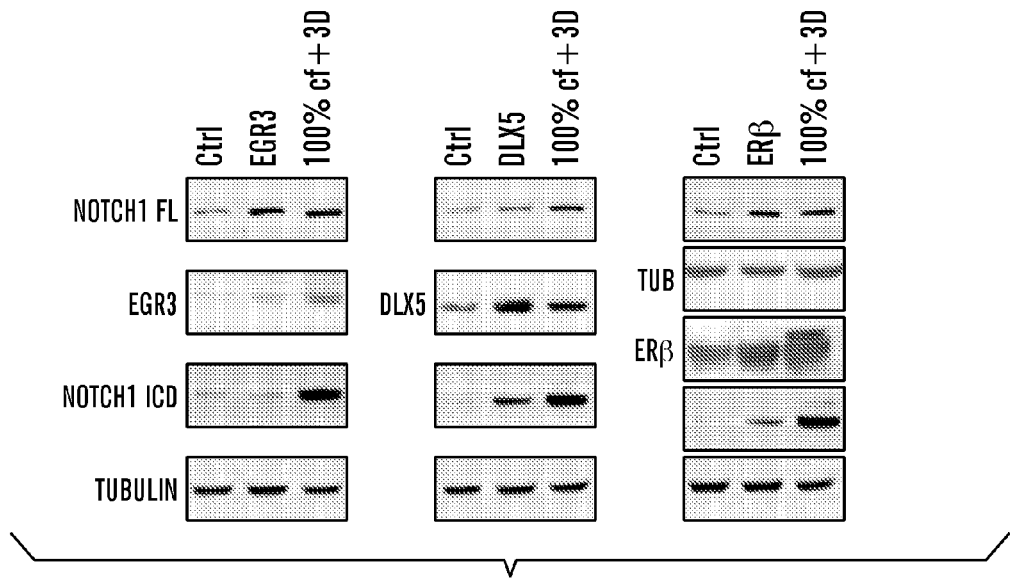
FIGS. 5A-5C demonstrate that EGR3, DLX5, and ERβ are regulators of NOTCH1 expression and function in HKCs.
Figure 5B:
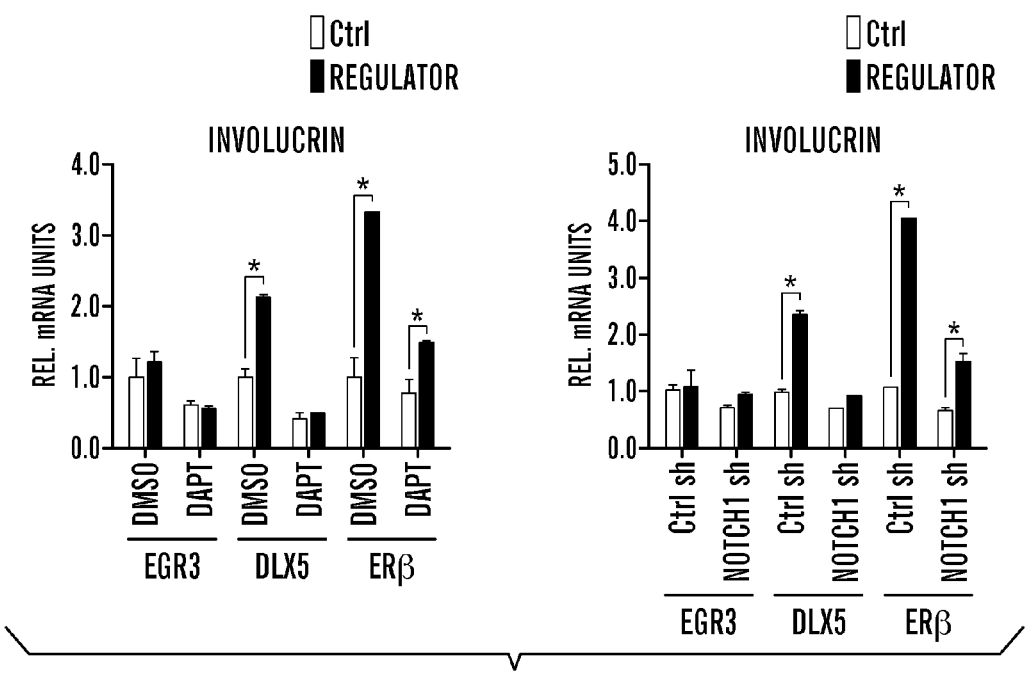
Figure 5C:
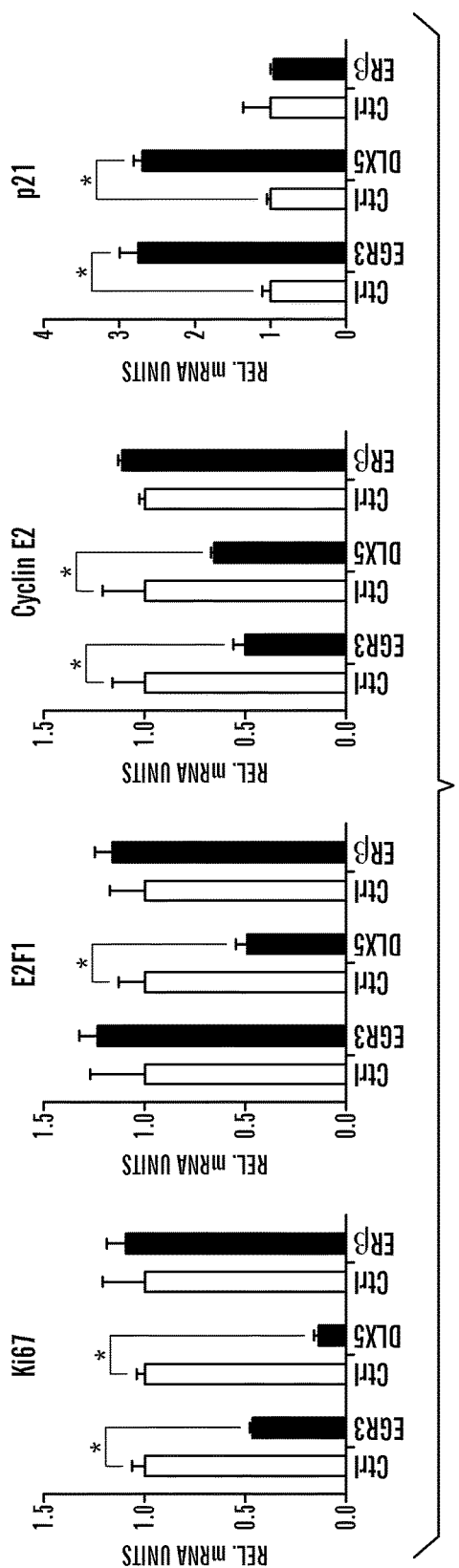

For a complementary gain-of-function approach, it was assessed whether increased expression of the Egr3, Dlx5 and ERβ proteins via retroviral vector transduction, to levels comparable to those found with differentiation, was sufficient to induce Notch1 mRNA and protein expression (FIGS. 5A and 15A). Interestingly, immunoblot analysis with antibody against the intracellular activated form of Notch1 (Notch1 ICD) showed enhanced Notch1 activation only in HKCs with increased Dlx5 and ERβ but not Egr3 expression (FIGS. 5A and 15B), suggesting that additional post-transcriptional events required for Notch1 activation are also induced by the first two regulators but not the third. Consistent with these findings, enhanced expression of Dlx5 and ERβ, but not Egr3, led to induction of the canonical Notch target Hey1 as well as the differentiation marker involucrin, which was prevented to a large extent by concomitant inhibition of Notch activation by treatment with the γ-secretase inhibitor DAPT or Notch1 knock-down (FIG. 5B). Interestingly, increased Egr3, Dlx5, and ERβ levels had different effects on expression of cell cycle and proliferation marker genes. While increased ERβ expression did not elicit any changes, elevated Egr3 and Dlx5 expression down-regulated Ki67 and cyclin E2 levels and induced $p21^{WAF1/CIP1}$, consistent with the fact that keratinocyte differentiation and cell cycle control can be separately controlled (32) (FIG. 5C).

Deregulated Expression of Notch1 Regulators in SCC of Skin, Head and Neck and Lung.

Consistent with its tumor suppressor function, the Notch1 gene is down-regulated or mutated in a significant fraction of skin, head/neck and lung SCC (3, 5, 9, 33). Analysis of gene expression profiles of these tumors from different datasets confirmed the frequent down-modulation of Notch1, along with up-regulation of genes under negative Notch control in keratinocytes, like p63, integrin β6 and β4 (data not shown). Expression of "canonical" Notch targets of the Hes/Hey family was variously modulated, consistent with their capability to cross-regulate each other and their regulation by other input signaling pathways (34-37). In particular, Hes1 expression was commonly decreased in skin and head/neck SCCs, Hey1 was down-modulated in the first set of tumors and up-regulated in the second, and both Hes1 and Hey1 were increased in lung SCCs (data not shown).

Figure 6A:
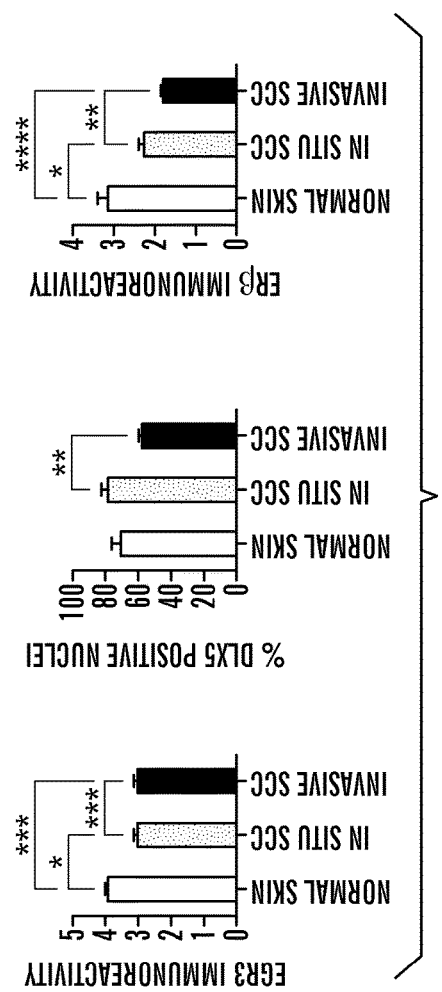
FIGS. 6A-6C demonstrate that deregulated expression of EGR3, DLX5, and ERβ and other NOTCH1 regulators in cutaneous, H/N, and lung SCCs.
Figure 6C:
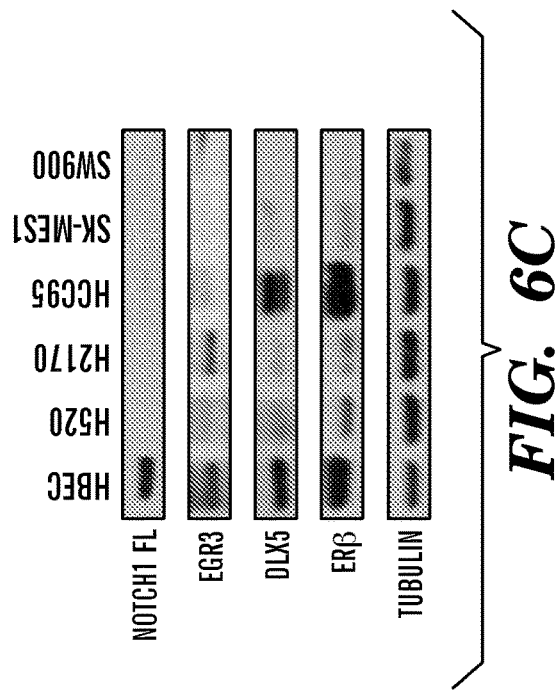
Figure 6B:
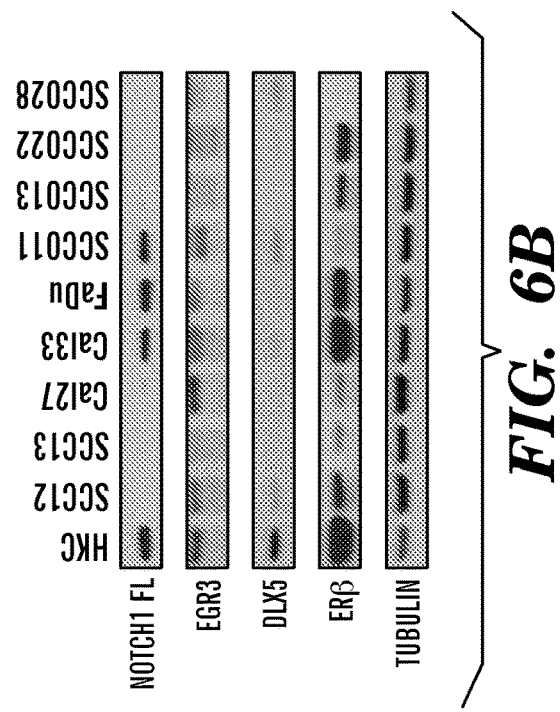

Many transcription factor genes identified in this screen as modulators of Notch1 expression were also deregulated in SCCs, with closer variations in skin and head/neck SCCs than lung SCCs. While Egr3 was commonly down-modulated in tumors from the three body sites, Dlx5 was variably expressed. ESR2 expression was decreased in skin and lung SCC while another Notch1 regulator that is required for ER binding to target DNA, Pbx1 (38), was down-modulated in many skin and head/neck SCCs and, more variably, in the lung SCCs (FIG. 6A). Expression of the Egr3, Dlx5, and ERβ proteins was found decreased by immunohistochemical analysis of a large set of skin SCCs on tissue arrays (FIG. 6A). Decreased expression of these genes was also seen by immunoblot analysis of a number of skin, head/neck and lung SCC cell lines (FIGS. 6B-6C).

ERβ and Gender-Selected Mutational and Gene Expression Signatures of SCC.

Figure 7A:
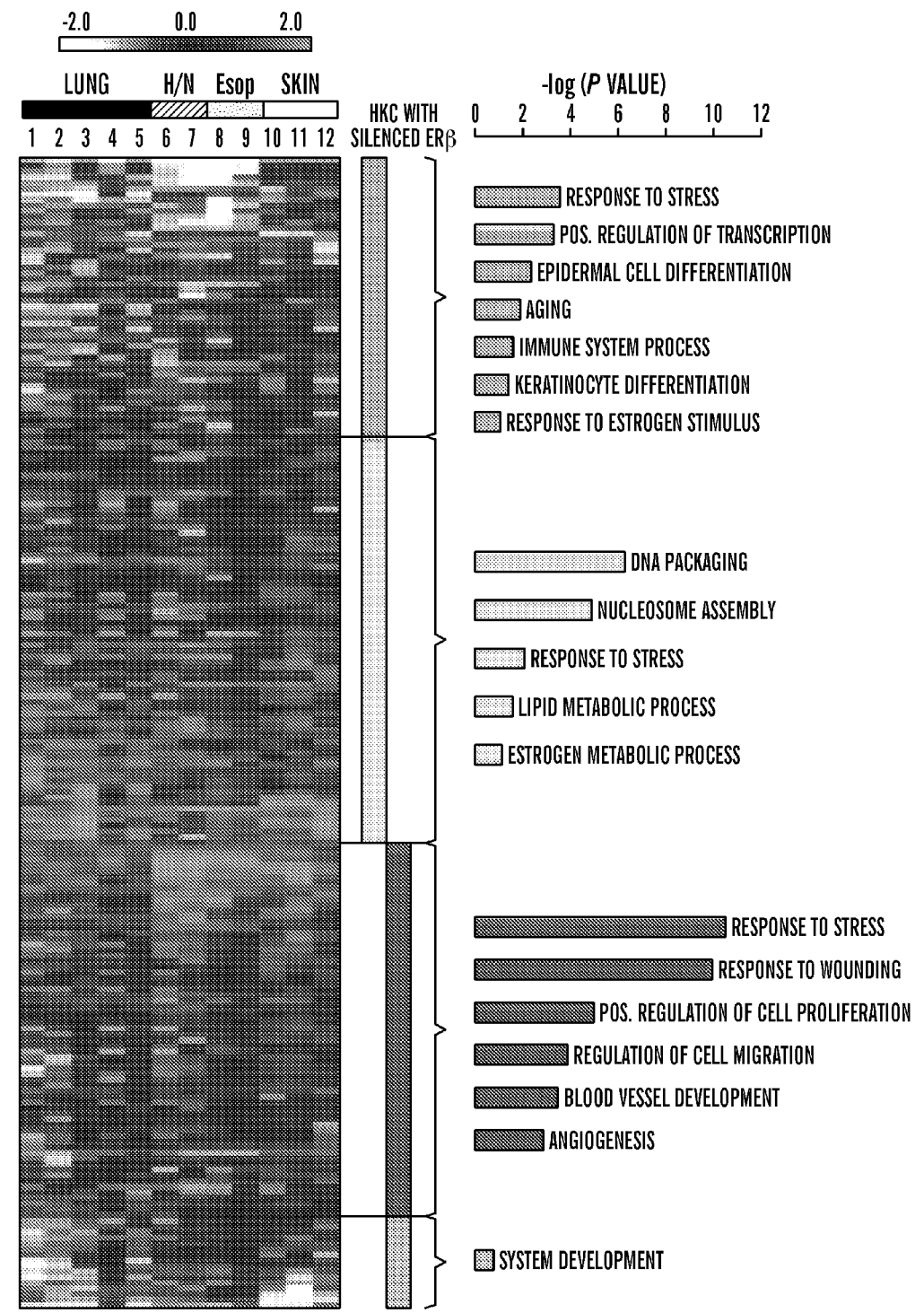
FIGS. 7A-7C demonstrate that comparative gene expression and mutation profiles of skin, H/N, and lung SCCs in relation to ER signaling and/or patients' sex.

Given the translational potential, for further studies ERβ was focused upon. At first the global impact of decreased ERβ signaling on the transcriptional program of primary keratinocytes was assessed, including to what extent these changes in gene expression overlap with those in clinically occurring SCCs. cDNA microarray analysis of HKCs plus/minus ERβ knock-down confirmed that genes related to epidermal differentiation were down-regulated in HKCs with silenced ERβ expression. Besides ER-dependent genes, other gene families significantly down-modulated in these cells included genes involved in stress response and positive regulation of transcription, while other stress response genes, genes involved in proliferation, wounding, cell migration and angiogenesis were up-regulated. A substantial fraction of genes within these families were found to be similarly de-regulated in gene expression profile studies of lung, head/neck, esophageal and skin SCCs (FIG. 7A). Interestingly, genes in other families were oppositely regulated in the ERβ-silenced HKCs versus clinical SCCs. These include a class of genes involved in DNA packaging and nucleosome assembly, lipid and estrogen metabolic processes, and a less defined category of "system development"-related genes.

Figure 7B:
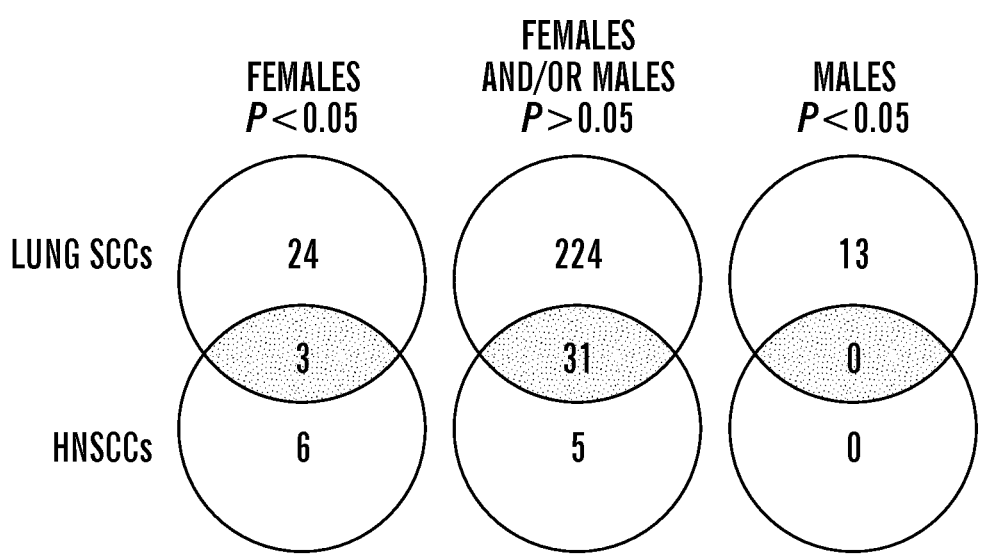

Epidemiologic studies indicate that there is a greater risk of skin, head/neck and lung SCC in the male versus female populations, which may not be simply due to differences in life style (39). For further insights, the results of next-generation sequencing studies of head/neck (available on the world wide web at tcga-data.nci.nih.gov/tcga/; Peter S Hammerman and TCGA Network personal communication) and lung SCCs (4) that could be divided between female versus male patients were examined. Surprisingly, among genes mutated in at least 10% of SCCs, a number exhibited a statistically significant difference in mutation frequency between the two genders (FIG. 7B). Many of these genes have interesting cell signaling functions in the context of gender-differences in SCC susceptibility.

Figure 7C:
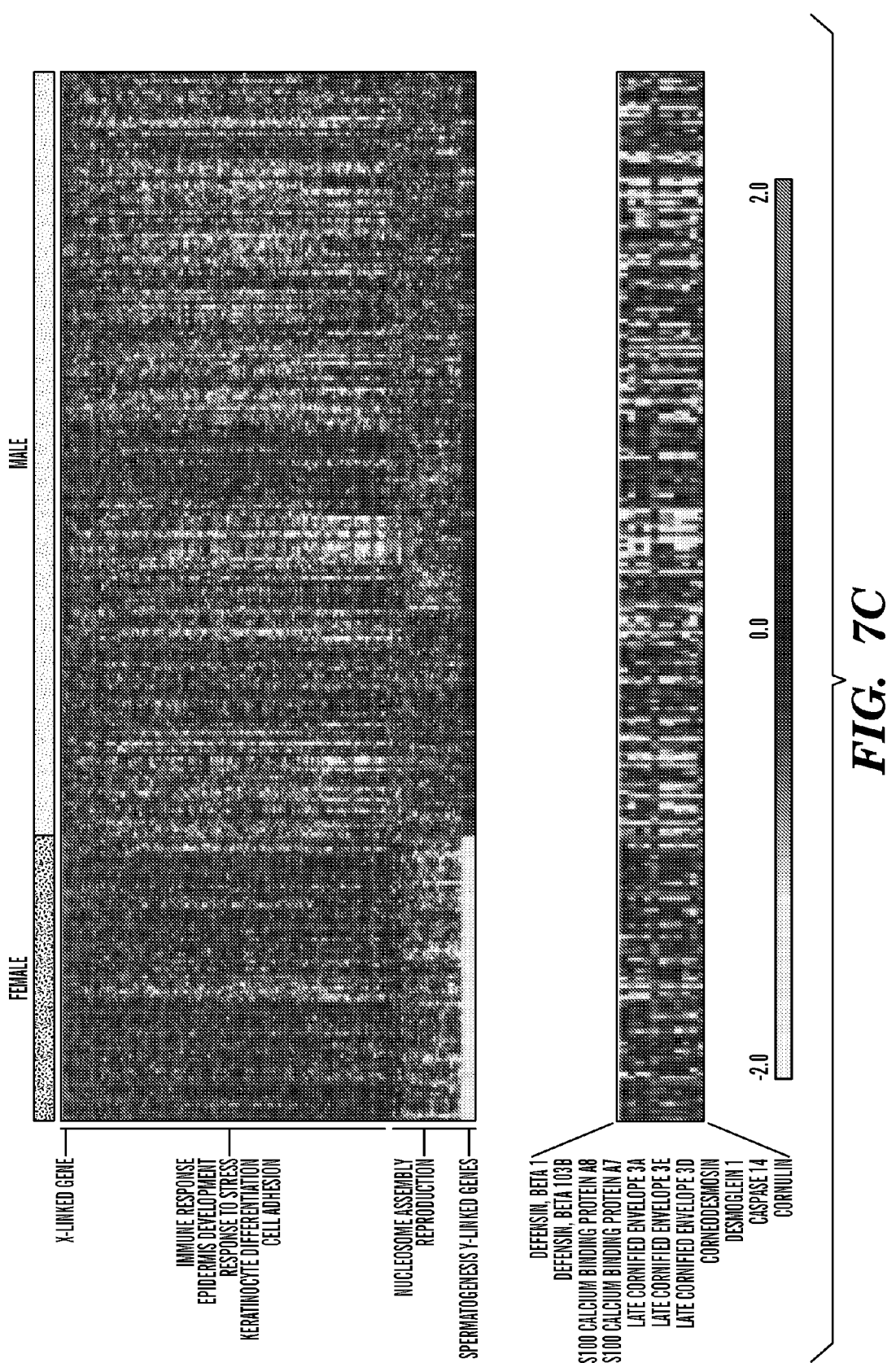

Besides gene mutations, it was examined whether there may also be differences in the global gene expression profiles of head/neck SCCs from the two sexes utilizing a recent gene expression study of tumors versus matched normal tissues (40). Unsupervised clustering of the whole data set of genes was not sufficient to segregate SCCs from female versus male patients (FIG. 7C). When focusing on the estrogen-dependent gene expression signature identified by analysis of keratinocytes plus/minus ERβ silencing discussed above, it was found that, with one exception, SCCs from female patients segregated from those of males for expression of genes related to estrogen metabolic processes, hormone response, wound healing, angiogenesis, cell adhesion and epithelial and keratinocyte differentiation (FIG. 7D). Further parallel analysis of SCCs and control normal tissues showed that tumors had significantly greater gender-related differences in gene expression of families involved in inflammatory response, tissue remodeling and wound repair, nuclear receptor signaling, estrogen signaling and protein degradation (FIG. 7E).

ERβ is a Positive Determinant of Notch1 Gene Expression and Function in SCC Cells.

To directly assess the impact of increased ERβ signaling in SCC outgrowth, a panel of skin, oral and lung SCC cell lines were infected with ERβ expressing versus control viruses. As shown in FIG. 8A, proliferation of most cell lines, as assessed by Alamar Blue cell density assays, was significantly inhibited as a consequence of ERβ overexpression. Cells with elevated proliferative potential, as assessed by colony or sphere formation assays, were also significantly reduced (FIGS. 8B-8E and 16A-16B). Increased ERβ expression in SCC cell lines derived from various body sites was accompanied by up-regulation of Notch1 and differentiation marker expression (FIG. 9A), with induction of the latter being significantly counteracted by DAPT treatment (FIG. 9B). To test the in vivo impact of increased ERβ expression, representative cell lines from skin (SCC13), head/neck (SCCO13) and lung SCCs (H2170) were assessed by intra-dermal tumorigenicity assays in immune compromised mice (42). Cells infected with the ERβ expressing lentivirus formed tumors of similar size as the controls, but enhanced Notch1 expression and differentiation (FIGS. 9C-9D).

Besides estrogen, other agonists have been developed with elevated specificity for either the ERα or ERβ receptors (43). Use of these molecules can be permit induction of squamous cell differentiation and SCC tumor suppression. Treatment of HKCs with either 17β-estradiol (E2) or 2,3-bis(4-Hydroxyphenyl)-propionitrile (DPN), an ERβ selective agonist (43), resulted in induction of Notch1 expression as well as differentiation marker expression (FIG. 10A). Little or no induction was observed after treatment with 1,3,5-Tris(4-hydroxyphenyl)-4-propyl-1H-pyrazole (PPT), an ERα selective agonist, while Notch1 as well as differentiation marker expression was suppressed by treatment with Fulvestrant, a complete ER antagonist (43, 44) (FIG. 10A). Treatment of a panel of SCC cell lines with the ERβ selective agonist DPN resulted also in induction of Notch1 and differentiation marker expression (FIG. 10B). Importantly, proliferation and sphere forming capability of a number of SCC cell lines was also significantly suppressed by the DPN treatment (FIGS. 10C and 10D). As an in vivo test, a cohort of mice were intra-dermally injected with SCCO13 cells, followed by daily administration of DPN or DMSO vehicle alone. Relative to controls, mice treated the ERβ selective agonist exhibited tumors of significantly smaller size and reduced proliferative index (FIG. 11), with increased Notch1 and differentiation marker expression (data not shown).

Discussion

Recent advances in whole genome analysis provide unique opportunities to probe into coordinate control of gene expression and ensuing biological events. Identified herein is a transcriptional regulatory network converging on control of Notch1 gene transcription in squamous cell differentiation and cancer. Most of the transcription factors are themselves de-regulated in skin and oral squamous cell carcinoma, with some undergoing gene mutations and/or rearrangements (3, 5, 33). Functions of these factors, together with interactions of possible relevance, are summarized in Table 2. Further functional and biochemical studies were focused on three of the factors that were found to play a direct and positive role in transcriptional up-regulation of the Notch1 gene during differentiation, with ERβ as a possible target of translational significance.

Egr3 belongs to a family of four highly conserved zinc finger transcription factors, originally identified in the "early response" of cells to growth factor stimulation (45). These proteins bind to the same consensus DNA sequence and can have a significant functional overlap. Little is known on function of these genes in squamous differentiation, with mice with deletion of the Egr3 gene exhibiting little skin abnormalities, possibly due to functional compensation by other Egr family members (20). A connection with Notch signaling, to our knowledge, has not been reported. It is demonstrated herein that Egr3 functions in keratinocytes as a direct positive regulator of Notch1 gene expression, with endogenous Egr3 binding to the Notch1 locus and being required for RNA PolII recruitment with differentiation. Exogenous Egr3 expressed to levels similar to those found in differentiation was sufficient for induction of Notch1 gene transcription. Interestingly, however, the increased levels of Notch1 mRNA and protein resulting from EGR3 up-regulation were not accompanied by a corresponding increase in the proteolytically cleaved activated Notch1 protein. Without wishing to be bound by theory, it is contemplated herein that Egr3 controls expression of Notch1 but not of other determinants of Notch activation, whose concomitant up-regulation may instead account for the Notch1 activation by Dlx5 and ERβ discussed below.

Homeobox genes play a key role in development and cancer (48). Surprisingly, however, a direct connection between this important class of transcriptional regulators and Notch signaling has not been established. Dlx5 belongs to the family of Distal-less (Dlx) homeobox genes, identified for their role in distal limb development (19). There are 6 family members, with different members having the potential of carrying out the same biological function in different species (19). Dlx5 and Dlx6 have been shown to play an important role downstream of p63 in the apical endodermal ridge and limb development (49). IT is described herein that in human keratinocytes, Dlx5 functions as a direct positive regulator of Notch1 expression and exerts a pro-differentiation function that is, in part, Notch dependent. Besides Dlx5, another homeobox gene that was shown by this screen to be required for Notch1 expression is PBX1.

Estrogen receptors play a significant role in human physiology and disease, with a role extending to sex-unrelated organs, like intestinal and cardiovascular systems (21, 22). The two main estrogen receptors, ERα and ERβ, are encoded by separate genes (ESR1 and ESR2) and exhibit distinct tissue-specific patterns of expression. ERβ is the form predominantly expressed in human epidermal cells in vivo (53) as well as in culture (our observations). Relative to ERα, the biochemical function of ERβ is less established as it was mostly studied in cells with over-expression of the exogenous protein (25). Like Egr3 and Dlx5, it is described herein that ERβ is induced and plays a direct positive role in control of Notch1 expression in keratinocyte differentiation. Further biochemical analysis described above herein revealed that, while both Egr3 and Dlx5 are required for recruitment of RNA PolII to the Notch1 locus, ERβ is likely involved in pause release of this enzyme from the transcription start site. Following establishment of a transcription initiation complex, the onset of elongation is emerging as a highly regulated process for transcription of many genes, especially with developmental and/or signal transduction functions (30). Control of Notch1 expression by RNA PolII pause release to our knowledge has not been previously reported.

Squamous cell carcinomas are notoriously resistant to conventional and targeted drug treatments and novel differentiation therapy approaches, alone or in combination, may be of substantial value (56). Besides HKCs, it was found that increased ERβ induces Notch1 expression and differentiation also in keratinocyte-derived skin and head/neck SCC cells, both in vitro and in vivo. Interestingly, ERβ-induced expression of Notch1 and squamous differentiation markers also in lung SCC lines, consistent with the capability of bronchial epithelial cells to undergo squamous cell differentiation as a possibly protective reaction against cancer development (57).

The incidence of clinically occurring SCCs in skin, oral mucosa and lung is significantly higher in males than females for reasons that are not simply amenable to different life styles (39) and can be observed also experimentally (58, 59). Cancer patients' survival is also different between the two genders (available on the world wide web at seer.cancer.gov/). Excitingly, taking advantage of recent next generation sequencing data, a so far unsuspected specificity of gene mutations in head/neck and lung SCCs of female versus male patients was uncovered, pointing to a possible molecular basis for differences of the disease between the two sexes. Such a possibility is further supported by the finding that SCCs of female and male patients can be discriminated on the basis of their total as well as ER-dependent gene expression program, with several functional gene families being differently affected. Without wishing to be bound by theory, it is contemplated herein that estrogen-dependent control of Notch1 expression and differentiation underlies these sex differences and that, by enhancing the squamous differentiation network identified herein, estrogen mimetic compounds, in particular, ERß-specific agonists, can be used in combination with other treatment modalities of pre-malignant and malignant lesions.

Methods

Cells, Tissue Samples and Viruses.

HKCs and SCC (SCCO11, SCCO13, SCCO22 and SCCO28) cell lines were obtained and cultured as previously described (9, 42). Human bronchial epithelial cells (HBEC) were purchased from ATCC. Squamous cell carcinoma samples were obtained at the Department of Dermatology of the Zurich University Hospital Switzerland from clinical biopsies. Parts not needed for histological diagnosis were further processed with institutional review board approval.

Constructs for retro- and lenti-viral production were obtained or made as follows. pMXs-ESR2 was constructed by cloning the Flag-tagged full-length cDNA of ESR2 from pCXN2 vector into the BamHI/NotI sites of the PMx vector using the following primers: forward 5'-GATTCCGGATC-CGCCACCATGGACTACAAGGACGACGAT-GACAAGGATATAAAAAACTCACCA-3' (SEQ ID NO: 1) and reverse 5'-GCTGCTGCGGCCGCCTACTGAGACT-GTGGGTTCTG-3' (SEQ ID NO: 2). Lentiviral vectors of CSII-DLX5, CSII-EGR3 and CSII-ESR2 were constructed by cloning DLX5, EGR3 and ESR2 from retroviral vectors into CSII-EF-RfA-IRES2-Venus vector using Gateway cloning kits (Invitrogen, NY). The following primers were used: DLX5 forward 5'-CACCATGGACTACAAGGAC-GACGATGACAAGACAGGAGTGTTTGACAGA-3' (SEQ ID NO: 3) and reverse 5'-CTAATAGAGTGTCCCG-GAGGC-3' (SEQ ID NO: 4), EGR3 forward 5'-CACC ATGGACTACAAGGACGACGATGACAAGACCG-GCAAACTCGCCGAG-3' (SEQ ID NO: 5) and reverse 5'-TGAGGCGCAGGTGGTGACCAC-3' (SEQ ID NO: 6), ESR2 forward 5'-CACC ACC ATGGACTACAAGGAC-GACGATGACAAGGATATAAAAAACTCACCA-3' (SEQ ID NO: 7) and reverse 5'-CTACTGAGACTGTGGGT-TCTG-3' (SEQ ID NO: 8). The accuracy of cloned vectors was confirmed by DNA sequencing. The lentiviral shRNA for DLX5 (TRCN0000007448 and TRCN0000007449), EGR3 (TRCN0000013843 and TRCN0000013847 and ESR2 (TRCN0000003325 and TRCN0000003328) were purchased from Openbiosystems.

Clonogenicity and Alamar Blue assays were as reported (60). For spheroid assays, 8-well chamber slides were coated with matrigel (BDbiosciences, CA; 50 µl per well) and incubated at 37° C. for 20 minutes to allow matrigel to polymerize. SCC cells were brought into suspension in normal culture medium plus 1% matrigel (7000 cells/ml) and added in triplicates to the pre-coated chamber slides (300 µl of cell mixture per well). Medium was refreshed every other day. For organotypic cultures, HKCs were infected with shRNA expressing lentiviruses followed, 48 hours later, by selection for puromycin (2 mg/ml) resistance. Selected keratinocyte cultures were reseeded onto collagen gels with embedded J2-3T3 fibroblasts and cultured at the air-liquid interface as previously described (61). After 12 days, epithelial sheets were peeled off the collagen lattice, snap frozen and processed for immunoblot analysis, or embedded in tissue freezing medium for immunohistochemical analysis or fixed in 10% neutral buffered formalin and embedded in paraffin for standard histology.

siRNA Screen.

A customized library (from Ambion) with three individual siRNAs for each selected gene was reversely transfected into HKCs in 384-well plates (30 nM of each siRNA, tested in triplicate wells, in 0.8% Hiperfect™ (Qiagen, Calif.). Hiperfect™ was diluted in serum free medium (SFM, Invitrogen) for 5 minutes before mixing with siRNAs diluted in the same medium. The mixture was incubated for 20 min at RT and then added to 384-well plates. Plates were spun down at 1000 rpm for 5 min and 5000 HKCs in medium without antibiotics were added to each well robotically. The plates were spun down at 1000 rpm for 5 min again and then placed in a tissue culture incubator at 37° C. with 5% $CO_2$. Twenty-four hour post-transfection, the transfection medium was removed and fresh HKC culture medium was added. At this time point, cells in each well were about 90-100% confluent. Medium was changed every other day. One week post-transfection, cells were cells were directly lysed in the wells, followed by RNA and cDNA preparation with a FastLane cell cDNA kit (Qiagen, Calif.) following manufacturer's instructions. siRNAs for Dlx5, Egr3 and ERß used for ChIP assays were purchased from Ambion/Invitrogen with the following specific sequences. Egr3: 5'-AGAUC-CACCUCAAGCAAAAtt-3' (SEQ ID NO: 9), Dlx5: 5' CAGAGAAGGUUUCAGAAGAtt (SEQ ID NO: 10) and ERß 5'-CCUUACCUGUAAACAGAGAtt-3' (SEQ ID NO: 11).

RT-qPCR, Immunodetection and ChIP Assays.

Conditions for RT-qPCR, immunoblotting, immunofluorescence and ChIP assays were as previously reported (9, 42). List of gene-specific primers and antibodies is provided in Table 3 and 4. For immunoblotting, unless otherwise indicated, cells were lysed in SDS sample buffer (50 mM Tris-HCl pH 6.8, 2% SDS, 10% glycerol, 0.2 unit nuclease) and protein separation was done in 15-well 4-12% NuPAGE Bis-Tris polyacrylamide gels (Invitrogen). Equal loading controls were done by re-probing the same immunoblots unless otherwise indicated. All assays were done at least twice, with two HKC strains or epidermal samples of independent origin.

Intradermal Tumorigenicity Assays.

Lenti-virally-infected SCC13, SCCO13 cells and retrovirally infected H2170 cells were suspended in matrigel followed by intra-dermal injection ($1.0 \times 10^6$ cells in 150 µl per injection) into the back skin of 6 weeks old NOD/SCID mice (Taconic Farms Inc. Germantown, N.Y.) as described (9, 42). To minimize the individual animal variations, cells infected with control and ERß expressing viruses were injected in parallel in the right and left flank of the same mice. Mice were sacrificed for tissue analysis 3 weeks (SCC13 and SCCO13) or 1 week (H2170) after injection. For ERß agonist studies, SCCO13 cells were injected intradermally into NOD/SCID mice as described above. 48 hours later, mice were randomly divided into two groups, one receiving 2,3-bis(4-Hydroxyphenyl)-propionitrile (20 mg/kg; approx. DMSO stock solution diluted 1:33 in culture medium) and the other DMSO alone (also diluted 1:33 in culture medium), by daily intra-peritoneal injections for 10 days.

Bioinformatic Analysis.

Matinspector™ software (Genomatix), the Match tool from TRANSFAC™ and the UCSC Genome Browser database were used for identification of transcription factors with putative binding sites within the predicted enhancer and promoter sequences of the Notch1 locus as identified by the ENCODE project analysis of human primary keratinocytes. A gene expression microarray database of normal human epidermis and primary skin SCC tumors (GEO # GSE45164) and published gene expression array data from Biogps and Genecards were used to "filter" for keratinocyte-expressed transcription factors. For comparative transcriptomic analysis of selected genes in skin, oral and lung SCCs versus normal epidermis, oral mucosa and lung epithelium, two Affymetrix datasets (our own, GEO GSE45164, for skin SCCs; and ArrayExpress E-GEOD-9844 for oral SCCs) and one single-color Agilent oral SCCs dataset (ArrayExpress E-GEOD-23558) were used. Lung SCCs datasets were retrieved from Oncomine RNA array database (available on the world wide web at oncomine.com). Affymetrix data were processed with the RMA algorithm while Agilent data were background subtracted (normexp method) and normalized with the quantile functions. Values of multiple probes targeting the same gene were pooled and averaged and log 2 ratios of the individual tumors versus mean values of control tissues were calculated, separately for each dataset. For determination of ER-dependent gene expression program, HKCs were transfected with two ERß-specific siRNAs scrambled siRNAs followed, 96 hrs later, by total RNA preparation and cDNA microarray hybridization (Affimetrix U133A.2.0) and bioinformatics analysis as previously described (42). For comparison of the ER-dependent gene expression program in skin, head/neck, esophageal and lung SCCs, corresponding datasets (Bhattachariee, Garber, Hou, Talbot, Wachi, Cromer, Ginos, Hu, Su, Nindl, Riker) were retrieved from Oncomine RNA array database together with GSE45164. For mutation spectrum analysis of head/neck and lung SCCs from male versus female patients, data were obtained from TCGA network through personal communication with Dr. Peter S Hammerman and TCGA network and from previously public datasets (4), respectively. For gene expression profiles of Head/Neck SCCs from male versus female patients, data were retrieved from ArrayExpress (E-GEOD-9844) and analyzed as described above. Unsupervised hierarchical clustering was performed using Spearman Rank Correlation as similarity metrics and complete linkage method on both the whole set of the probe set present on the array and on genes differentially expressed after ERβ silencing. Functional classification was performed using the functional annotation tool available within DAVID website (available on the world wide web at david.abcc.nciferf.gov/). MetaCore™ version 6.16 from Thomson Reuters was used to identify pathway maps differently affected in females vs male HNSCCs with respect to female vs male corresponding matched normal controls.

Statistical Analysis.

To assess statistical significance of the results, Prism™ software 6.0 (GraphPad software Inc.) unpaired student's t test were used. All real-time RT-PCR samples were tested in triplicate and error bars represent s.d. P-values less than 0.05 were considered significant.

Study Approval.

The animal study (protocol #: 2004N000170) was approved by the Subcommittee on Research Animal Care (SRAC), which serves as the Institutional Animal Care and Use Committee (IACUC) in Massachusetts General Hospital. The animal study was carried out in strict accordance with the recommendations in the Guide for the Care and Use of Laboratory Animals of the National Institutes of Health.

REFERENCES

1. Kopan, R., and Ilagan, M. X. 2009. The canonical Notch signaling pathway: unfolding the activation mechanism. *Cell* 137:216-233.
2. Lefort, K., and Dotto, G. P. 2004. Notch signaling in the integrated control of keratinocyte growth/differentiation and tumor suppression. *Semin Cancer Biol* 14:374-386.
3. Agrawal, N., Frederick, M. J., Pickering, C. R., Bettegowda, C., Chang, K., Li, R. J., Fakhry, C., Xie, T. X., Zhang, J., Wang, J., et al. 2011. Exome sequencing of head and neck squamous cell carcinoma reveals inactivating mutations in NOTCH1. *Science* 333:1154-1157.
4. Hammerman, P. S., Hayes, D. N., Wilkerson, M. D., Schultz, N., Bose, R., Chu, A., Collisson, E. A., Cope, L., Creighton, C. J., Getz, G., et al. 2012. Comprehensive genomic characterization of squamous cell lung cancers. *Nature* 489:519-525.
5. Wang, N.J., Sanborn, Z., Arnett, K. L., Bayston, L. J., Liao, W., Proby, C. M., Leigh, I. M., Collisson, E. A., Gordon, P. B., Jakkula, L., et al. 2011. Loss-of-function mutations in Notch receptors in cutaneous and lung squamous cell carcinoma. *Proc Natl Acad Sci USA* 108: 17761-17766.
6. Dotto, G. P. 2008. Notch tumor suppressor function. *Oncogene* 27:5115-5123.
7. Aster, J. C., Blacklow, S. C., and Pear, W. S. 2011. Notch signalling in T-cell lymphoblastic leukaemia/lymphoma and other haematological malignancies. *J Pathol* 223: 262-273.
8. Guo, S., Liu, M., and Gonzalez-Perez, R. R. 2011. Role of Notch and its oncogenic signaling crosstalk in breast cancer. *Biochimica et biophysica acta* 1815:197-213.
9. Lefort, K., Mandinova, A., Ostano, P., Kolev, V., Calpini, V., Kolfschoten, I., Devgan, V., Lieb, J., Raffoul, W., Hohl, D., et al. 2007. Notch1 is a p53 target gene involved in human keratinocyte tumor suppression through negative regulation of ROCK1/2 and MRCKalpha kinases. *Genes Dev* 21:562-577.
10. Yugawa, T., Handa, K., Narisawa-Saito, M., Ohno, S., Fujita, M., and Kiyono, T. 2007. Regulation of Notch1 gene expression by p53 in epithelial cells. *Mol Cell Biol* 27:3732-3742.
11. Gomez-del Arco, P., Kashiwagi, M., Jackson, A. F., Naito, T., Zhang, J., Liu, F., Kee, B., Vooijs, M., Radtke, F., Redondo, J. M., et al. 2010. Alternative promoter usage at the Notch1 locus supports ligand-independent signaling in T cell development and leukemogenesis. *Immunity* 33:685-698.
12. Lambertini, C., Pantano, S., and Dotto, G. P. 2010. Differential control of Notch1 gene transcription by Klf4 and Sp3 transcription factors in normal versus cancer-derived keratinocytes. *PLoS One* 5:e10369.
13. Yang, Y., Nakagawa, H., Tetreault, M. P., Billig, J., Victor, N., Goyal, A., Sepulveda, A. R., and Katz, J. P. 2011. Loss of transcription factor KLF5 in the context of p53 ablation drives invasive progression of human squamous cell cancer. *Cancer research* 71:6475-6484.
14. Wells, J., Lee, B., Cai, A. Q., Karapetyan, A., Lee, W. J., Rugg, E., Sinha, S., Nie, Q., and Dai, X. 2009. Ovol2 suppresses cell cycling and terminal differentiation of keratinocytes by directly repressing c-Myc and Notch1. *The Journal of biological chemistry* 284:29125-29135.
15. Cai, J., Lee, J., Kopan, R., and Ma, L. 2009. Genetic interplays between Msx2 and Foxn1 are required for Notch1 expression and hair shaft differentiation. *Developmental biology* 326:420-430.
16. Cao, F., Hata, R., Zhu, P., Nakashiro, K., and Sakanaka, M. 2010. Conditional deletion of Stat3 promotes neurogenesis and inhibits astrogliogenesis in neural stem cells. *Biochemical and biophysical research communications* 394:843-847.
17. Yashiro-Ohtani, Y., He, Y., Ohtani, T., Jones, M. E., Shestova, O., Xu, L., Fang, T. C., Chiang, M. Y., Intlekofer, A. M., Blacklow, S. C., et al. 2009. Pre-TCR signaling inactivates Notch1 transcription by antagonizing E2A. *Genes Dev* 23:1665-1676.
18. Bedogni, B., Warneke, J. A., Nickoloff, B. J., Giaccia, A. J., and Powell, M. B. 2008. Notch1 is an effector of Akt and hypoxia in melanoma development. *The Journal of clinical investigation* 118:3660-3670.
19. Panganiban, G., and Rubenstein, J. L. 2002. Developmental functions of the Distal-less/Dlx homeobox genes. *Development* 129:4371-4386.
20. Tourtellotte, W. G., and Milbrandt, J. 1998. Sensory ataxia and muscle spindle agenesis in mice lacking the transcription factor Egr3. *Nat Genet* 20:87-91.
21. Heldring, N., Pike, A., Andersson, S., Matthews, J., Cheng, G., Hartman, J., Tujague, M., Strom, A., Treuter, E., Warner, M., et al. 2007. Estrogen receptors: how do they signal and what are their targets. *Physiological reviews* 87:905-931.
22. Nilsson, S., and Gustafsson, J. A. 2011. Estrogen receptors: therapies targeted to receptor subtypes. *Clinical pharmacology and therapeutics* 89:44-55.
23. Magnani, L., Stoeck, A., Zhang, X., Lanczky, A., Mirabella, A. C., Wang, T. L., Gyorffy, B., and Lupien, M. 2013. Genome-wide reprogramming of the chromatin landscape underlies endocrine therapy resistance in breast cancer. *Proceedings of the National Academy of Sciences of the United States of America* 110: E1490-1499.
24. Rizzo, P., Miao, H., D'Souza, G., Osipo, C., Song, L. L., Yun, J., Zhao, H., Mascarenhas, J., Wyatt, D., Antico, G., et al. 2008. Cross-talk between notch and the estrogen receptor in breast cancer suggests novel therapeutic approaches. *Cancer research* 68:5226-5235.
25. Grober, O. M., Mutarelli, M., Giurato, G., Ravo, M., Cicatiello, L., De Filippo, M. R., Ferraro, L., Nassa, G., Papa, M. F., Paris, O., et al. 2011. Global analysis of estrogen receptor beta binding to breast cancer cell genome reveals an extensive interplay with estrogen receptor alpha for target gene regulation. *BMC genomics* 12:36.
26. Chan, K. S., Sano, S., Kiguchi, K., Anders, J., Komazawa, N., Takeda, J., and DiGiovanni, J. 2004. Disruption of Stat3 reveals a critical role in both the initiation and the promotion stages of epithelial carcinogenesis. *The Journal of clinical investigation* 114:720-728.
27. Van Dyck, F., Declercq, J., Braem, C. V., and Van de Ven, W. J. 2007. PLAG1, the prototype of the PLAG gene family: versatility in tumour development (review). *International journal of oncology* 30:765-774.
28. Alon, U. 2007. Network motifs: theory and experimental approaches. *Nat Rev Genet* 8:450-461.
29. Li, G., Ruan, X., Auerbach, R. K., Sandhu, K. S., Zheng, M., Wang, P., Poh, H. M., Goh, Y., Lim, J., Zhang, J., et al. 2012. Extensive promoter-centered chromatin interactions provide a topological basis for transcription regulation. *Cell* 148:84-98.
30. Adelman, K., and Lis, J. T. 2012. Promoter-proximal pausing of RNA polymerase II: emerging roles in metazoans. *Nat Rev Genet* 13:720-731.
31. Nickoloff, B., Qin, J., Chaturvedi, V., Denning, M., Bonish, B., and Miele, L. 2002. Jagged-1 mediated activation of notch signaling induces complete maturation of human keratinocytes through NF-kappaB and PPAR-gamma. *Cell Death Differ* 9:842-855.
32. Lefort, K., Brooks, Y., Ostano, P., Cario-Andre, M., Calpini, V., Guinea-Viniegra, J., Albinger-Hegyi, A., Hoetzenecker, W., Kolfschoten, I., Wagner, E. F., et al. 2013. A miR-34a-SIRT6 axis in the squamous cell differentiation network. *EMBO J.*
33. Stransky, N., Egloff, A. M., Tward, A. D., Kostic, A. D., Cibulskis, K., Sivachenko, A., Kryukov, G. V., Lawrence, M. S., Sougnez, C., McKenna, A., et al. 2011. The mutational landscape of head and neck squamous cell carcinoma. *Science* 333:1157-1160.
34. Iso, T., Kedes, L., and Hamamori, Y. 2003. HES and HERP families: multiple effectors of the Notch signaling pathway. *J Cell Physiol* 194:237-255.
35. Itoh, F., Itoh, S., Goumans, M. J., Valdimarsdottir, G., Iso, T., Dotto, G. P., Hamamori, Y., Kedes, L., Kato, M., and ten Dijke Pt, P. 2004. Synergy and antagonism between Notch and BMP receptor signaling pathways in endothelial cells. *Embo J* 23:541-551.
36. Quillien, A., Blanco-Sanchez, B., Halluin, C., Moore, J. C., Lawson, N. D., Blader, P., and Cau, E. 2011. BMP signaling orchestrates photoreceptor specification in the zebrafish pineal gland in collaboration with Notch. *Development* 138:2293-2302.
37. Revollo, J. R., Oakley, R. H., Lu, N. Z., Kadmiel, M., Gandhavadi, M., and Cidlowski, J. A. 2013. HES1 Is a Master Regulator of Glucocorticoid Receptor-Dependent Gene Expression. *Science signaling* 6:ra103.
38. Magnani, L., Ballantyne, E. B., Zhang, X., and Lupien, M. 2011. PBX1 genomic pioneer function drives ERalpha signaling underlying progression in breast cancer. *PLoS genetics* 7:e1002368.
39. Burns, K. A., and Korach, K. S. 2012. Estrogen receptors and human disease: an update. *Arch Toxicol* 86:1491-1504.
40. Ye, H., Yu, T., Temam, S., Ziober, B. L., Wang, J., Schwartz, J. L., Mao, L., Wong, D. T., and Zhou, X. 2008. Transcriptomic dissection of tongue squamous cell carcinoma. *BMC genomics* 9:69.
41. Hayes, C. L., Spink, D. C., Spink, B. C., Cao, J. Q., Walker, N.J., and Sutter, T. R. 1996. 17 beta-estradiol hydroxylation catalyzed by human cytochrome P450 1B1. *Proceedings of the National Academy of Sciences of the United States of America* 93:9776-9781.
42. Wu, X., Nguyen, B. C., Dziunycz, P., Chang, S., Brooks, Y., Lefort, K., Hofbauer, G. F., and Dotto, G. P. 2010. Opposing roles for calcineurin and ATF3 in squamous skin cancer. *Nature* 465:368-372.
43. Harrington, W. R., Sheng, S., Barnett, D. H., Petz, L. N., Katzenellenbogen, J. A., and Katzenellenbogen, B. S. 2003. Activities of estrogen receptor alpha- and beta-selective ligands at diverse estrogen responsive gene sites mediating transactivation or transrepression. *Molecular and cellular endocrinology* 206:13-22.
44. Dowsett, M., Nicholson, R. I., and Pietras, R. J. 2005. Biological characteristics of the pure antiestrogen fulvestrant: overcoming endocrine resistance. *Breast cancer research and treatment* 93 Suppl 1:S11-18.
45. O'Donovan, K. J., Tourtellotte, W. G., Millbrandt, J., and Baraban, J. M. 1999. The EGR family of transcription-regulatory factors: progress at the interface of molecular and systems neuroscience. *Trends Neurosci* 22:167-173.
46. Gomez-Martin, D., Diaz-Zamudio, M., Galindo-Campos, M., and Alcocer-Varela, J. 2010. Early growth response transcription factors and the modulation of immune response: implications towards autoimmunity. *Autoimmunity reviews* 9:454-458.
47. Guinea-Viniegra, J., Zenz, R., Scheuch, H., Jimenez, M., Bakiri, L., Petzelbauer, P., and Wagner, E. F. 2012.

Differentiation-induced skin cancer suppression by FOS, p53, and TACE/ADAM17. *J Clin Invest.*
48. Abate-Shen, C. 2002. Deregulated homeobox gene expression in cancer: cause or consequence? *Nature reviews. Cancer* 2:777-785.
49. Lo Iacono, N., Mantero, S., Chiarelli, A., Garcia, E., Mills, A. A., Morasso, M. I., Costanzo, A., Levi, G., Guerrini, L., and Merlo, G. R. 2008. Regulation of Dlx5 and Dlx6 gene expression by p63 is involved in EEC and SHFM congenital limb defects. *Development* 135:1377-1388.
50. Morasso, M. I., Markova, N. G., and Sargent, T. D. 1996. Regulation of epidermal differentiation by a Distal-less homeodomain gene. *J Cell Biol* 135:1879-1887.
51. Hwang, J., Mehrani, T., Millar, S. E., and Morasso, M. I. 2008. Dlx3 is a crucial regulator of hair follicle differentiation and cycling. *Development* 135:3149-3159.
52. Jackson, B., Brown, S. J., Avilion, A. A., O'Shaughnessy, R. F., Sully, K., Akinduro, O., Murphy, M., Cleary, M. L., and Byrne, C. 2011. TALE homeodomain proteins regulate site-specific terminal differentiation, LCE genes and epidermal barrier. *Journal of cell science* 124:1681-1690.
53. Thornton, M. J., Taylor, A. H., Mulligan, K., Al-Azzawi, F., Lyon, C. C., O'Driscoll, J., and Messenger, A. G. 2003. Oestrogen receptor beta is the predominant oestrogen receptor in human scalp skin. *Exp Dermatol* 12:181-190.
54. Fullwood, M. J., Liu, M. H., Pan, Y. F., Liu, J., Xu, H., Mohamed, Y. B., Orlov, Y. L., Velkov, S., Ho, A., Mei, P. H., et al. 2009. An oestrogen-receptor-alpha-bound human chromatin interactome. *Nature* 462:58-64.
55. Mitra, P., Pereira, L. A., Drabsch, Y., Ramsay, R. G., and Gonda, T. J. 2012. Estrogen receptor-alpha recruits P-TEFb to overcome transcriptional pausing in intron 1 of the MYB gene. *Nucleic Acids Res* 40:5988-6000.
56. Kolev, V., Mandinova, A., Guinea-Viniegra, J., Hu, B., Lefort, K., Lambertini, C., Neel, V., Dummer, R., Wagner, E. F., and Dotto, G. P. 2008. EGFR signalling as a negative regulator of Notch1 gene transcription and function in proliferating keratinocytes and cancer. *Nat Cell Biol* 10:902-911.
57. Ishizumi, T., McWilliams, A., MacAulay, C., Gazdar, A., and Lam, S. 2010. Natural history of bronchial preinvasive lesions. *Cancer Metastasis Rev* 29:5-14.
58. Cho, J. L., Allanson, M., and Reeve, V. E. 2010. Oestrogen receptor-beta signalling protects against transplanted skin tumour growth in the mouse. *Photochem Photobiol Sci* 9:608-614.
59. Mancuso, M., Gallo, D., Leonardi, S., Pierdomenico, M., Pasquali, E., De Stefano, I., Rebessi, S., Tanori, M., Scambia, G., Di Majo, V., et al. 2009. Modulation of basal and squamous cell carcinoma by endogenous estrogen in mouse models of skin cancer. *Carcinogenesis* 30:340-347.
60. Dai, J., Brooks, Y., Lefort, K., Getsios, S., and Dotto, G. P. 2013. The retinoid-related orphan receptor RORalpha promotes keratinocyte differentiation via FOXN1. *PloS one* 8:e70392.
61. Getsios, S., Simpson, C. L., Kojima, S., Harmon, R., Sheu, L. J., Dusek, R. L., Cornwell, M., and Green, K. J. 2009. Desmoglein 1-dependent suppression of EGFR signaling promotes epidermal differentiation and morphogenesis. *The Journal of cell biology* 185:1243-1258.

TABLE 2

Summary of gene information and protein functions of 15 identified Notch1 regulators.

| Gene Symbol | Gene Name | TF family | General Function | Epidermal Function | Known genetic alteration |
|---|---|---|---|---|---|
| PBX1 | pre B cell leukemia homeobox 1 | PBX homeobox family | 1. At transcription regulation level, PBX1 protein interacts with other homedomaincontaining proteins, including HOX and MEIS to form transcription compdlexes. It also acts as a pioneer factor to facilitate the recruitment of ERalpha in breast cancer. 2. PBX1 regulates the development of spleen, pancreas, kidney, adrenal gland, and skeleton and is involved in tumorigenesis. | 1. PBX1 competes with sp1/3 factors to bind to the promoters of Late cornified envelope protein genes and activates their expression in differentiated keratinocytes. 2. Epidermal-specific Pbx1-null mice are viable and have epidermal barrier abnormalities. | TCF3-PBX1 and E2A-PBX1 translocations in pre-B-cell acute lymphoblastic leukemia (ALL) |
| RARA | retinoic acid receptor alpha | Nuclear hormone receptor family | 1. RARA plays an important role in regulation of development, differentiation, apoptosis, granulopoeisis, and transcription of clock genes. 2. RARA regulates transcription by dimerizing with RXR and in a ligand-dependent manner. 3 RARA is a critical factor in ER transcription complex by maintaining cofactor interaction. | 1. Both RARG and RARA are expressed in epidermal keratinocytes with RARG being the predominant isoform. RAR-beta was induced by RA in dermal fibroblasts, but not in keratinocytes. 2. Terminal differentiation of epidermal keratinocytes is inhibited by retinoic | BCOR-RARA, PML-RARA, NPM-RARA, NuMA-RARA, STAT5b-RARA and PLZF-RARα translocations in acute promyelocytic leukemia (APL) |

TABLE 2-continued

Summary of gene information and protein functions of 15 identified Notch1 regulators.

| Gene Symbol | Gene Name | TF family | General Function | Epidermal Function | Known genetic alteration |
|---|---|---|---|---|---|
| | | | | acid in parallel with the inhibition of the synthesis of suprabasal keratins, filaggrin, and transglutaminase. | |
| PURA | purine-rich element binding protein A | PUR DNAbinding protein family | 1. PURA is a sequencespecific single-stranded DNA-binding protein which binds purine rich elements present at the origins of replication and in gene flanking regions. It is implicated in the control of both DNA replication and transcription. 2. PURA is a component of the transcription repressor complex on the promoter of adrogen receptor gene. The loss of PURA leads to AR overexpression and androgen-independent prostate cancer. | No study has been reported. | Deletion of PURA has been reported in myelodysplastic syndrome and acute myelogenous leukemia. |
| MZF1 | myeloid zinc finger 1 | Krüppel family of zinc finger proteins | 1. MZF1 is critical for blood cell development and its disruption leads to a block of granulopoiesis. 2. Mzf1 can act as a tumor/growth suppressor in the hemopoietic compartment. | In normal human keratinocytes, MZF1 activates the transcription of peptidylarginine deiminase type I gene (PADI1) which is involved in keratinocyte differentiation. | No study has been reported. |
| YBX1 | Y box binding protein 1 | cold-shock protein superfamily | 1. YBX1 binds to both DNA and RNA and can exert its function in cytoplasm, nucleus as well as cell surface. 2. YBX1 participates in various cellular processes, including apoptosis, cell proliferation, development and differentiation. The YB_1 gene knockout in mice results in serious distortions of embryonic development and in early (prenatal) death. 3. YBX1 is involved in tumorigensis by interacting with E2F, PI3K/Akt/mTOR and Ras/Raf/MEK/ERK pathways pathways. | No study has been reported. | No study has been reported. |
| PLAG1 | pleiomorphic adenoma gene 1 | PLAG gene family | 1. The expression of PLAG1 is developmentally regulated. 2. PLAG1 promotes cell proliferation by inducing cell growth pathways, such as IGF-II pathway. 3. PLAG1 transgenic mice develop a variety of tumor types. | No study has been reported. | CTNNB1-PLAG1. LIFRPLAG1, SII/TCEA1-PLAG1, CHCHD7-PLAG1 Pleomorphic adenomas of the salivary gland. (HAS2-PLAG1, COL1A2-PLAG1 in lipoblastomas. Gene amplification in hepatoblastoma |

TABLE 2-continued

Summary of gene information and protein functions of 15 identified Notch1 regulators.

| Gene Symbol | Gene Name | TF family | General Function | Epidermal Function | Known genetic alteration |
|---|---|---|---|---|---|
| HOXA9 | homeobox A9 | HOX gene family | 1. HOXA9 promoters ovarian cancer progression by creating permissive microenvironment for tumor growth through TGFB2 action in fibroblasts. 2. HOXA9 restrains breast cancer progression by BRCA1 upregulation. | Mice with conditional deletion of the HoxA cluster, combined with deletions within the HoxD cluster exhibit a striking skin phenotype: largely edematous skin, without epidermal stratification and differentiation of epithelial appendages. | NUP98-HOXA9 in myeloid leukemogenesis |
| HSF1 | heat shock transcription factor 1 | HSF gene family | 1. HSF1 is an evolutionarily conserved gene which can be activated by various stressors. 2. HSF1 mediates adaptive responses in an array of physiological processes, such as cell cycle control, ribosome biogenesis, protein translation, and glucose metabolism. 4. In mouse models and cell cultures, HSF1 enables oncogenic transformation and maintains malignant phenotype. | It regulates heat shock protein-72 expression in human keratinocytes exposed to ultraviolet B light to protect against UV induced damage. HSF1 is required for normal growth and survival of melanoma cells under heat shock conditions. | No study has been reported. |
| NANOG | Nanog homeobox | NANOG homeobox family | 1. NANOG is involved in the maintenance of stemness (self-renewal, undifferentiated state) and immunomodulation in ESC and adult stem cells. 2. Nanog's expression in cancer cells promotes cancer stem cell characteristics and is positively correlated with tumor maliganancy. | No study has been reported. | No study has been reported. |
| STAT3 | signal transducer and activator of transcription 3 | STAT protein family | 1. STAT3 is activated by IL-6, IL-11, leukemia inhibitory factor (LIF), ciliary neurotrophic factor (CNTF), oncostatin M and cardiotropin. 2. Constitutively activated STAT3 is found in a number of epithelial cancers, including including prostate, breast, lung, head and neck, and pancreas, as well as hematopoietic malignancies, such as, lymphomas, leukemias, mucosis fungoides, and multiple myelomas. 3. Ablation of STAT3 leads to apoptosis and inhibition of cell proliferation. | 1. In mouse skin, activated STAT3 is found at the wounding edge and is involved in re-epithelization process. 2. Transgenic mice with keratinocyte specific-deletion of STAT3 display markedly reduced wound healing capability and enhanced resistance to chemical-induce carcinogenesis. 3. Various skin tumor promoters can activate STAT3 in mouse epidermis trhough EGFR activation. 4. In human psoriatic patients, activated STAT3 is found in the lesional keratinocytes. | No study has been reported |

TABLE 2-continued

Summary of gene information and protein functions of 15 identified Notch1 regulators.

| Gene Symbol | Gene Name | TF family | General Function | Epidermal Function | Known genetic alteration |
|---|---|---|---|---|---|
| ZEB1 | zinc finger Ebox binding homeobox 1 | ZEB family | 1. ZEB1 is crucial for neural crest cell migration and formation of derivative structures during embryonic development. 2. ZEB1 is an inducer of epithelial-mesenchymal transition and its elevated expression is observed in cancerous tissues 3. ZEB1 is involved in the regulatory loop with mir-200 microRNA family to mediate EMT. | 1. Estrogen increases ZEB1 expression in a human foreskin fibroblast cell line in vitro. 2. ZEB1 is significantly over expressed in the penile skin of subjects with severe hypospadias. | No study has been reported |
| SMAD1 | SMAD family member 1 | SMAD family | 1. SMAD1 is a signal transducer of BMP signaling which is involved in cellular processes, such as cell growth, apoptosis, morphogenesis, development and immune responses. | 1. SMAD1 mediated BMP signaling plays pivotal roles in the control of cutaneous development and also possesses a potent antitumor activity in postnatal skin. 2. Overexpression of BMP4/6 in murine epidermis is accompanied by increased resistance to chemically induced carcinogenesis. 3. In chemically induced murine epidermal tumors and in human basal cell carcinoma cells, Smad1/5 are strongly downregulated. 4. Total and phosphorylated Smad1 levels are significantly elevated in systemic sclerosis (SSc) skin biopsy samples and in cultured SSc fibroblasts. | No study has been reported |
| DLX5 | distal-less homeobox 5 | homeobox transcription factor family | 1. Dlx5; Dlx6 doubleknockout mice exhibit Split Hand-Foot Malformation phenotype which is observed in patients with p63 mutation. 2. Dlx5; Dlx6 are under positive transcriptional control of ΔNp63 during embryonic limb development (E10.5 to E12.5). | No study has been reported | 1. DLX5 mutation is associated with splithand/split-foot malformation. 2. The chromosomal region containing DLX5/DLX6 undergoes a recurrent inversion in T-cell lymphoma from Lck-Akt2 transgenic mice. |

TABLE 2-continued

Summary of gene information and protein functions of 15 identified Notch1 regulators.

| Gene Symbol | Gene Name | TF family | General Function | Epidermal Function | Known genetic alteration |
|---|---|---|---|---|---|
| EGR3 | early growth response 3 | EGR family of C2H2-type zinc-finger proteins | 1. EGR3 is an immediate-early growth response gene which is induced by mitogenic stimulation. 2. Egr3 - deficient animals had gait ataxia (lack muscle spindles), increased frequency of perinatal mortality, scoliosis, resting tremors and ptosis. | No study has been reported | No study has been reported |
| ESR2 | estrogen receptor 2 (ER beta) | Nuclear hormone receptor family | Estrogen receptor mediated transcription plays an important role in human physiology and pathology. | 1. ESR2 is the ER subtype in the epidermis. 2. ESR2 is a tumor suppressor in skin and oral epithelium. | No study has been reported |

TABLE 3

DNA Oligonucleotide primers used in the study.

| GENE | Forward | SEQ ID NO | Reverse | SEQ ID NO |
|---|---|---|---|---|
| Primers for cloning | | | | |
| PMx-ERβ | GATTCCGGATCCGCCACCAT GGACTACAAGGACGACGATG ACAAGGAT | 0012 | ATAAAAAACTCACCA GCTGCTGCGGCCGCCTACT GAGACTGTGGGTTCTG | 0073 |
| CSII-Dlx5 | CACCATGGACTACAAGGACG ACGATGACAAGACAGGAGTG TTTGACAGA | 0013 | CTAATAGAGTGTCCCGGAG GC | 0074 |
| CSII-ERβ | CACCACCATGGACTACAAGG ACGAC GATGACAAGGATATAAAAAA CTCAC CA | 0014 | CTACTGAGACTGTGGGTTC TG | 0075 |
| Primers for RT-PCR | | | | |
| NOTCH1 | TTGGGAGGAGCAGATTTTTG | 0015 | CACTGGCATGACACACAAC A | 0076 |
| NOTCH1 PRIMARY | TTGTCTCCAGGGAAATCGTG | 0016 | GGCAGTGGCAGATGTAGGA G | 0077 |
| HEY1 | TCATTTGGAGTGTTGGTGGA | 0017 | CTCGCACACCATGATCACT T T | 0078 |
| NOTCH2 | GTTTCCAGTGCCTGTGTCCT | 0018 | CGATACACTTTGCCCCATTC | 0079 |
| JAG2 | GGAGGTTCTGCGATGAGTGT | 0019 | GCTGCCACAGTAGTTCAGG T | 0080 |
| CSL | CAAAAGTTGCACAGAAGTCA TA | 0020 | TGCTGCATTTCTTGGTCAC | 0081 |
| STAT3 | AGTTTCTGGCCCCTTGGA | 0021 | CTTCGTAGATTGTGCTGAT AGAGA | 0082 |
| HOXA9 | AGAACCGCAGGATGAAAATG | 0022 | GGGTGAGAGAAGGGAGAA GG | 0083 |
| PBX1 | GAAGCAGGACATTGGAGACA | 0023 | GGCTCCTCGGATACTCAAA AC | 0084 |
| RARA | GAAGAAGGAGGTGCCCAAG | 0024 | TCTGAGCTGTTGTTCGTAGT GT | 0085 |
| EGR3 | GATGGCTACAGAGAATGTAA TGGA | 0025 | AGTTGGAAGGGGAGTCGAA G | 0086 |
| HSF1 | GCAACAGAAAGTCGTCAACA AG | 0026 | GGCTATACTTGGGCATGGA A | 0087 |
| PLAG1 | CATCCCTCTCACCACCTTTC | 0027 | CGCCACCTTGTAACTCCAT C | 0088 |
| SMAD1 | TGCCCTCAGAAATCAACAGA | 0028 | TGAAACCATCCACCAACAC A | 0089 |
| NFKB1 | ACCAGCCTCTGTGTTTGTCC | 0029 | TGACGTTTCCTCTGCACTTC T | 0090 |

TABLE 3-continued

DNA Oligonucleotide primers used in the study.

| GENE | Forward | SEQ ID NO | Reverse | SEQ ID NO |
|---|---|---|---|---|
| DLX5 | TGAGCGATGACAGGAGTGTT | 0030 | CTGAGACGGATGGTGCATAG | 0091 |
| PURA | CCTATCGCAACTCCATCACC | 0031 | CCTCTGCTTCTCTTGAATCTTCTT | 0092 |
| MZF1 | GTGTAAGCCCTCACCTCCAC | 0032 | TGGGGTCCTGTTCACTCCT | 0093 |
| NANOG | GCAAGAACTCTCCAACATCCT | 0033 | GCGTCACACCATTGCTATTC | 0094 |
| ZEB1 | TGCACAAGAAGAGCCACAAG | 0034 | GCGCAAGACAAGTTCAAGG | 0095 |
| ESR2 | CAGCTAGTGCTCACCCTCCT | 0035 | ACACCTCCATCCAACAGCTC | 0096 |
| YBX1 | AAGGAACGGATATGGTTTCA | 0036 | CCACAGTCTCTCCATCTCCT | 0097 |
| IVL | GGCCCTCAGATCGTCTCATA | 0037 | CACCCTCACCCCATTAAAGA | 0098 |
| KRT1 | GTTCCAGCGTGAGGTTTGTT | 0038 | TAAGGCTGGGACAAATCGAC | 0099 |
| KRT10 | GAAAAGCATGGGCAACTCACA | 0039 | TGTCGATCTGAAGCAGGATG | 00100 |
| 36B4 | GCAATGTTGCCAGTGTCTGT | 0040 | GCCTTGACCTTTTCAGCAAG | 00101 |

Figure 4A:
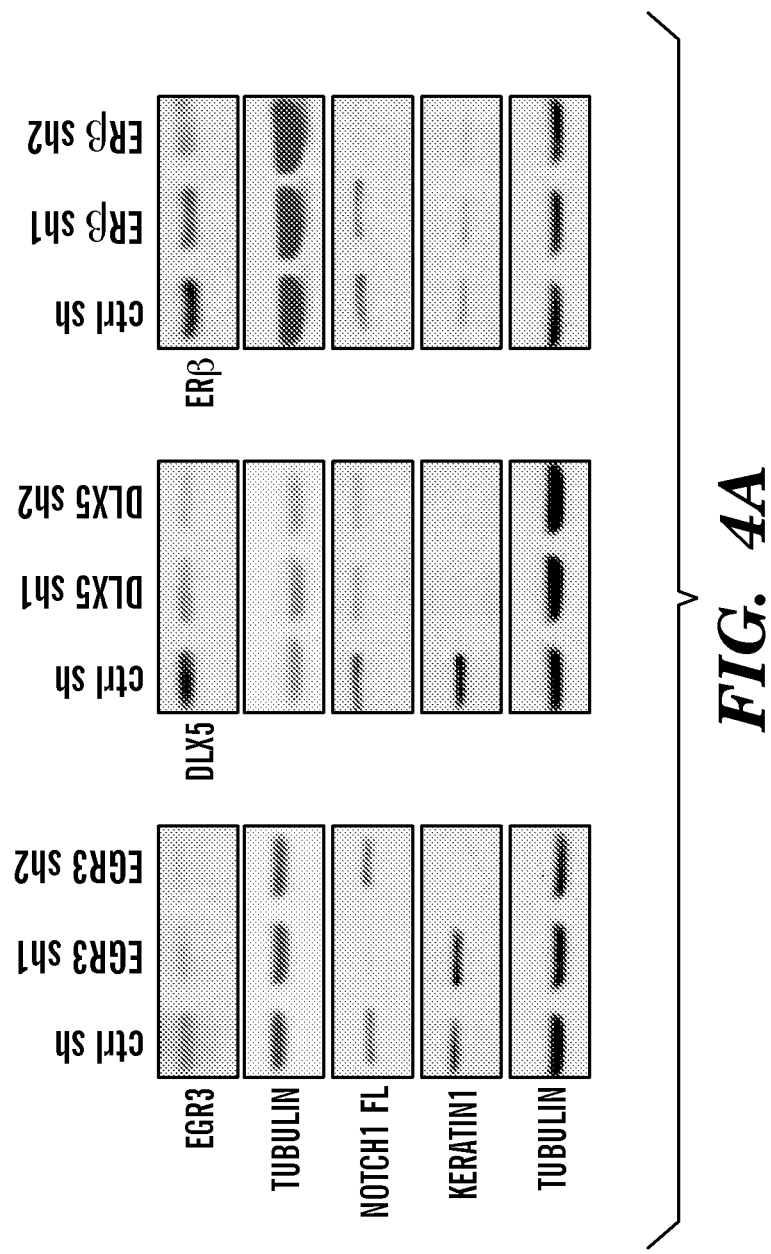
FIGS. 4A-4C demonstrate that silencing of EGR3, DLX5, and ERβ leads to attenuation of NOTCH1 expression and differentiation.
Figure 4B:
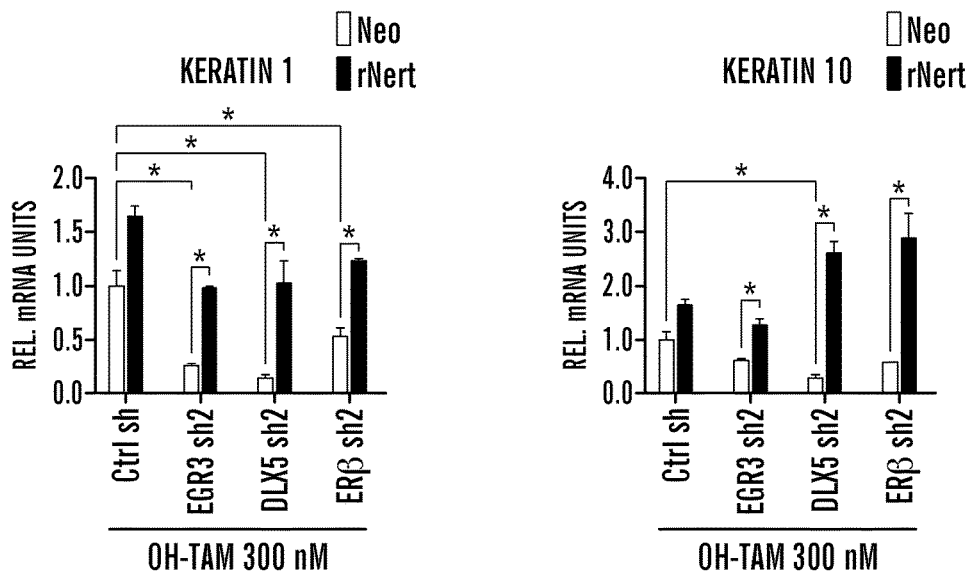
Figure 4C:
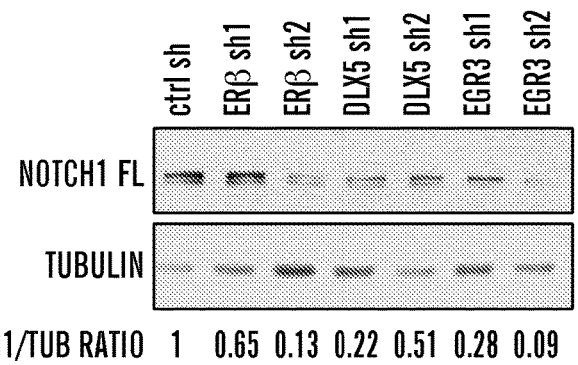

Primers for ChIP in FIG. 4A-4C

| DLX5 11.38 kb | GGGGCATTTACCCAGCTTT | 0041 | TCGTGTTGTTCCTTCTGCTC | 00102 |
|---|---|---|---|---|
| DLX5 0.9 KB | GCCGACACCCAATACCTG | 0042 | TCTCAGCCCCGGTAAGATG | 00103 |
| DLX5 1.9 KB | AGCTCCACACGCAGCATAA | 0043 | CGCAGGGGACAGAACACT | 00104 |
| EGR3 7.1 KB | GCTGCTGGTATTTCCTCCTC | 0044 | GTGCCAGTGCAGTTTTCATC | 00105 |
| EGR3 1.8 KB | CTGCCCTCGCAAAGCAAC | 0045 | CGGTGAGACCTGCCTGAA | 00106 |
| EGR3 0.5 KB | CCGCAGAGCCCACACTCC | 0046 | TTTGGTTTCCTGTTGCTTCTC | 00107 |
| EGR3 0.37 KB | AGATAAATGGCCCGGAGAAG | 0047 | GAGTTAGGAGGCCGGTGTG | 00108 |
| EGR3 0.21 KB | CACACCGGCCTCCTAACTC | 0048 | CCAGCATGGAGAGGGAAAA | 00109 |
| EGR3-0.06 KB | CGCCAAAGTTTCCAAAGG | 0049 | CCAGCCGGGAAGAGAGG | 00110 |
| EGR3-6.5 KB | AGAGGCGCTGCTGAGTGT | 0050 | AGGCCAAGAGAAAAGGCAAG | 00111 |
| ESR2 12.1 KB | GTCGAGGGCAGGACACTT | 0051 | GTAGGAGGCTGGAGCTTTTG | 00112 |
| ESR2 5.1 KB | CCTCACACACCACCAAGAGA | 0052 | CGCTTTAGCTTTGGACAACC | 00113 |
| ESR2 4.7 KB | GCCCTCTTCAGTACCCCTTG | 0053 | CGGAGGATGGTTGGTCTCT | 00114 |
| ESR2 4.56 KB | CCCAGAGACCAACCATCCT | 0054 | TGGTGCAAAATGCCTTCC | 00115 |
| ESR2 1.7 KB | TCACACTTCCCGCCATTC | 0055 | CCCCAGCAACCCATGATAC | 00116 |
| ESR2-30.9 KB | TGAGGTGAGGGCAGGAGTAG | 0056 | TGAGGAGTGGATGAGGGTGT | 00117 |
| ESR2-51.7 KB | CACTAGGAGCAGGGCGAGT | 0057 | AGATGCAGATGGCCTCAGTT | 00118 |
| ESR2-75.5 KB | ACCCCGTGGAGACCTGCT | 0058 | CTGTTCAGAGGCGGGAAA | 00119 |
| ESR2-75.8 KB | GCTGTGAACAACCACGTCTC | 0059 | TGAGGGCAAGACTCCACAC | 00120 |
| ESR2-76.1 KB | GCAGCAGATGGTGAAGGAG | 0060 | TCCTGGGGTAGAGAGGAGGT | 00121 |
| Negative Region | TCCTGACTGGGTCTCTCTCC | 0061 | TTGGCATTTGTCCCTCAAC | 00122 |

Primers for ChIP in FIG. 5A-5C

| E1 | GCCTCCTGTGCTACCTGTG | 0062 | CTCTGAAGGGCTTGAATTGG | 00123 |
|---|---|---|---|---|
| E2 | TGAAAACTGCACTGGCACAC | 0063 | GCGTCTAGCTTGCCTTCCT | 00124 |
| P | ATCTTACCGGGGCTGAGAAA | 0064 | GTCTCTGGGAATCGAGTGA | 00125 |
| E3 | GCTGCACTCTCTCTTCCCTTT | 0065 | AACGCTCAGACTTTTCTTGCT | 00126 |

TABLE 3-continued

DNA Oligonucleotide primers used in the study.

| GENE | Forward | SEQ ID NO | Reverse | SEQ ID NO |
|---|---|---|---|---|
| E4 | ACTTTCCCCTTCGCTGTCTC | 0066 | AATCAGCTCACAGTCCCACA | 00127 |
| E5 | GCGCCTCAGTCTTCTCTCCT | 0067 | GTTCCTGGTCGTTCCCATTC | 00128 |
| E6 | AGGGCAGGAGTAGCGAGAAG | 0068 | GAGGAGTGGATGAGGGTGTG | 00129 |
| E7 | CAGGGGATGTCGGTGTGT | 0069 | ACAGTGAAGACTGAAACCAGGAG | 00130 |
| E8 | TTGACAGCATCTTGGCATC | 0070 | TCCAGACATGACCTGCATC | 00131 |
| E9 | GCTGTGAACAACCACGTCTC | 0071 | GAGGGCAAGACTCCACACC | 00132 |
| Negative Region | TCCCACCAGCGTACACTAAA | 0072 | TCCCTGGTGTCTGAGTGTGA | 00133 |

TABLE 4

Information on antibodies used in the study.

| Name | Manufacturer | Cat. No. | Application and Dilution |
|---|---|---|---|
| Notch1 | Santa Cruz | sc-6014R | WB: 1/1000, IF: 1/200 |
| Notch1 ICD | Cell Signaling | 2421 | WB: 1/1000 |
| Egr3 | Santa Cruz | sc-191x | WB: 1/1000, IF: 1/100, ChIP: 5 ug per million cells |
| Dlx5 | Santa Cruz | sc-18152x | WB: 1/1000, IF: 1/100, ChIP: 2 ug per million cells |
| ERβ | Santa Cruz | sc-8974x | WB: 1/1000, IF: 1/100, ChIP: 5 ug per million cells |
| Keratin 1 | Covance | PRB-149P | WB: 1/2000 |
| Keratin 10 | Covance | PRB-159P | WB: 1/500 |
| Involucrin | Sigma | Mob270 | WB: 1/2000, IF: 1/500 |
| Loricrin | Covance | PRB-145P | IF: 1/500 |
| γ-Tubulin | Sigma | GTU-88 | WB: 1/2000 |
| RNA Polymerase II | Santa Cruz | sc-899x | ChIP: 5 ug per million cells |
| H3K4me1 | Abcam | ab8895 | ChIP: 2 ug per million cells |
| H3K4me3 | Abcam | ab8580 | ChIP: 2 ug per million cells |
| H3K27ac | Abcam | ab4729 | ChIP: 2 ug per million cells |
| H3K9ac | Abcam | Ab4441 | ChIP: 2 ug per million cells |
| H3K9me3 | Abcam | ab6001 | ChIP: 2 ug per million cells |
| H3K27me3 | Upstate | 07-449 | ChIP: 2 ug per million cells |

Example 2

Spheroid formation assays, as described above herein, were conducted with additional ERβ agonists; LY50037 (Eli Lily) and liquiritigenin obtained from Menerba (MF101; Bionovo). Assays were performed using skin, oral, and lung SCC cells. LY50037 showed striking efficacy in all cell lines tested (e.g., completely suppressed spheroid formation at 1 uM concentration) and the effects started to show as early as 5 days in the spheroid formation (FIGS. 18A-18C). Liquiritigenin is a much weaker ERbeta agonist, EC50=36.5 whereas DPN and LY50037 are in the 1-10 nM range.

What is claimed herein is:

1. A method of treating squamous cell carcinoma in a subject in need of treatment thereof, the method comprising administering to the subject an agonist of a gene selected from the group consisting of:

Esr2; Dlx5; and Egr3.

2. The method of claim 1, wherein the agonist of Esr2 is selected from the group consisting of: 17β-estradiol (E2); 2,3-bis(4-Hydroxyphenyl)-propionitrile (DPN); LY50037; liquiritigenin; MF101; WAY20070; YA-202196; WAY-214156; ERB041; FERb033; (S)-Equol; diarylpropionitrile; AC74131; silybinin; genistein; AC-186; KB9520; ERB-79; GTx-822; silymarin; ERβ-targeted phytoestrogen in combination with a lignan; and epigallocatechin gallate (EGCG).

* * * * *